(12) United States Patent  
Shaver et al.

(10) Patent No.: US 12,312,578 B2  
(45) Date of Patent: May 27, 2025

(54) FACILITIES AND PROCESSES TO PRODUCE BIOTHERAPEUTICS

(71) Applicant: Just-Evotec Biologics, Inc., Seattle, WA (US)

(72) Inventors: Jeremy Martin Shaver, Lake Forest Park, WA (US); Tileli Amimeur, Seattle, WA (US); Randal Robert Ketchem, Shalimar, FL (US); Michael W. Vandiver, Chesterfield, MO (US); Brian W. Horman, Bellevue, WA (US); Fernando Garcia Morales, Seattle, WA (US)

(73) Assignee: Just-Evotec Biologics, Inc., Seattle, WA (US)

( * ) Notice: Subject to any disclaimer, the term of this patent is extended or adjusted under 35 U.S.C. 154(b) by 836 days.

(21) Appl. No.: 17/431,085

(22) PCT Filed: Feb. 14, 2020

(86) PCT No.: PCT/US2020/018336  
§ 371 (c)(1),  
(2) Date: Aug. 13, 2021

(87) PCT Pub. No.: WO2020/168225  
PCT Pub. Date: Aug. 20, 2020

(65) Prior Publication Data  
US 2022/0251498 A1  Aug. 11, 2022

Related U.S. Application Data

(60) Provisional application No. 62/806,710, filed on Feb. 15, 2019.

(51) Int. Cl.  
*C12M 1/00* (2006.01)  
*C07K 1/16* (2006.01)  
(Continued)

(52) U.S. Cl.  
CPC ............... *C12M 47/10* (2013.01); *C07K 1/16* (2013.01); *C12M 29/04* (2013.01); *C12M 29/10* (2013.01);  
(Continued)

(58) Field of Classification Search  
CPC ...... C12M 47/10; C12M 47/12; C12M 29/04; C12M 29/10; C12M 37/00; C07K 1/16; C12P 21/00  
See application file for complete search history.

(56) References Cited

U.S. PATENT DOCUMENTS 5,656,491 A    8/1997  Cassani et al.  
9,908,064 B2   3/2018  Dresios et al.  
(Continued)

FOREIGN PATENT DOCUMENTS

CN   101395327    3/2009  
CN   101903512   12/2010  
(Continued)

OTHER PUBLICATIONS

"Chinese Application Serial No. 202080014808.9, Office Action mailed Aug. 28, 2024", w/o English translation, 10 pgs, with English claims.

(Continued)

*Primary Examiner* — Michael L Hobbs  
(74) *Attorney, Agent, or Firm* — Schwegman Lundberg & Woessner, P.A.

(57) ABSTRACT

The concepts described herein are directed to implementations of production facilities that can produce molecules used to treat biological conditions, such as biotherapeutics. The biotherapeutics can include various molecules, such as proteins, enzymes, and antibodies. The production facilities can include a number of separate modular cleanrooms that comprise particular pieces of equipment to perform one or  
(Continued)

more aspects of the processes used to manufacture biotherapeutics. The modular cleanrooms are arranged such that material that is produced by the equipment of one modular cleanroom can be transferred to another modular cleanroom for additional processing. Additionally, systems and processes are described to generate models using machine learning techniques, where the models can be used to predict productivity and/or efficiency metrics for production lines of biotherapeutics. Further, models can be generated to control the operation of pieces of equipment included in the production lines.

20 Claims, 10 Drawing Sheets

(51) Int. Cl.
    *C12M 1/12*     (2006.01)
    *C12P 21/00*     (2006.01)

(52) U.S. Cl.
    CPC ............ *C12M 37/00* (2013.01); *C12M 47/12* (2013.01); *C12P 21/00* (2013.01)

(56) References Cited

U.S. PATENT DOCUMENTS

| | | | |
|---|---|---|---|
| 2013/0109291 A1* | 5/2013 | Holtz | B23P 11/00 29/428 |
| 2014/0255994 A1 | 9/2014 | Konstantinov et al. | |
| 2015/0370228 A1 | 12/2015 | Kohn et al. | |
| 2020/0066369 A1* | 2/2020 | Downey | C12N 5/0602 |

FOREIGN PATENT DOCUMENTS

| | | |
|---|---|---|
| CN | 103649297 | 3/2014 |
| CN | 107073469 | 8/2017 |
| WO | WO-2007067656 A2 | 6/2007 |
| WO | WO-2012122413 A1 | 9/2012 |
| WO | WO-2015057722 A1 | 4/2015 |
| WO | WO-2017156420 A1 | 9/2017 |
| WO | WO-2018087150 A1 | 5/2018 |
| WO | WO-2020168225 A2 | 8/2020 |
| WO | WO-2020168225 A3 | 9/2020 |

OTHER PUBLICATIONS

"Japanese Application Serial No. 2021-547388, Response filed Aug. 9, 2024 to Notification of Reasons for Refusal mailed Mar. 12, 2024", W/English Claims, 17 pgs.
"International Application Serial No. PCT/US2020/018336, International Search Report mailed Aug. 14, 2020", 5 pgs.
"International Application Serial No. PCT/US2020/018336, Written Opinion mailed Aug. 14, 2020", 5 pgs.
"European Application Serial No. 20714030.2, Response Filed Mar. 31, 2022 to Communication pursuant to Rules 161(1) and 162 EPC mailed Sep. 22, 2021", 23 pgs.
"Chinese Application Serial No. 202080014808.9, Office Action mailed Dec. 1, 2023", with English translation, 18 pages.
"International Application Serial No. PCT US2020 018336, International Preliminary Report on Patentability mailed Aug. 26, 2021", 7 pgs.
"Japanese Application Serial No. 2021-547388, Notification of Reasons for Refusal mailed Mar. 12, 2024", with English translation, 12 pages.
"Chinese Application Serial No. 202080014808.9, Response filed Apr. 16, 2024 to Office Action mailed Dec. 1, 2023", with English claims, 33 pages.
"Chinese Application Serial No. 202080014808.9, Response filed Oct. 28, 2024 to Office Action mailed Aug. 28, 2024", W/English Claims, 35 pgs.
"Japanese Application Serial No. 2021-547388, Notification of Reasons for Refusal mailed (Nov. 26, 2024", w/ English Translation, 9 pgs.
"Chinese Application Serial No. 202080014808.9, Decision of Rejection mailed Dec. 11, 2024", with English translation, 21 pages.
Jin, Haiming, "Microcomputer Measurement and Control Technology", China Coal Industry Publishing House, with Concise Statement of Relevance and manual English translation, (Dec. 31, 1995), 9 pages.
Long, Hongming, "Mathematical Models and Artificial Intelligence Applications of Metallurgical Processes", Intelligent PID Controller Beijing Metallurgical Industry Press with Concise Statement of Relevance and manual English translation, (Jun. 30, 2010), 10 pages.

* cited by examiner

FACILITIES AND PROCESSES TO PRODUCE BIOTHERAPEUTICS

CROSS-REFERENCE TO RELATED APPLICATION(S) AND PRIORITY CLAIM

This application is a U.S. national stage filing under 35 U.S.C. 371 from International Application No. PCT/US2020/018336, filed on 14 Feb. 2020, and published as WO 2020/168225 A2 on 20 Aug. 2020, which claims priority to U.S. Provisional Application No. 62/806,710 filed on Feb. 15, 2019 and entitled "Facilities and Processes to Produce Biotherapeutics," the entirety of which are incorporated herein by reference.

BACKGROUND

The production of molecules that can be used to treat various biological conditions often takes place at a relatively large scale. For example, proteins can be manufactured in facilities that utilize bioreactors having capacities from 5000 L to 25,000 L. Often, the production lines developed to produce these molecules include equipment that is arranged according to a specific footprint that is not easily modified within the production facility. The lack of flexibility in the types of equipment and the arrangement of equipment utilized to produce a particular molecule or group of molecules can limit the applicability of a specified production line to other molecules. Thus, modifying an existing production line or constructing a new production line to produce different molecules can increase the costs associated with providing these molecules to the public. In turn, companies that manufacture biotherapeutics often decide to limit the number of molecules they produce due to the amount of resources needed to develop facilities for manufacturing a single molecule or group of molecules. Consequently, the cost of manufacturing biotherapeutics to treat biological conditions can lead to a limited number of biological conditions that can be treated using biotherapeutics and the number of biotherapeutics available to treat a given biological condition can also be limited.

Further, the control of systems that manufacture molecules that can be used to treat biological conditions can be complex and take into consideration a number of variables in order to optimize the production of the molecules. However, it can be difficult to discern the modifications that can be made to a particular manufacturing process that can result in more efficient production of the molecules because the techniques utilized to modify a manufacturing process are often ad hoc or anecdotal and not based on empirical data. Additionally, control systems are typically limited to controlling manufacturing processes at a single facility and are not used to control the manufacturing of one or more molecules at different facilities. Thus, data gathered from manufacturing a molecule at one production facility may not be utilized to improve the production of the same or a different molecule at another production facility.

DETAILED DESCRIPTION

Figure 1:
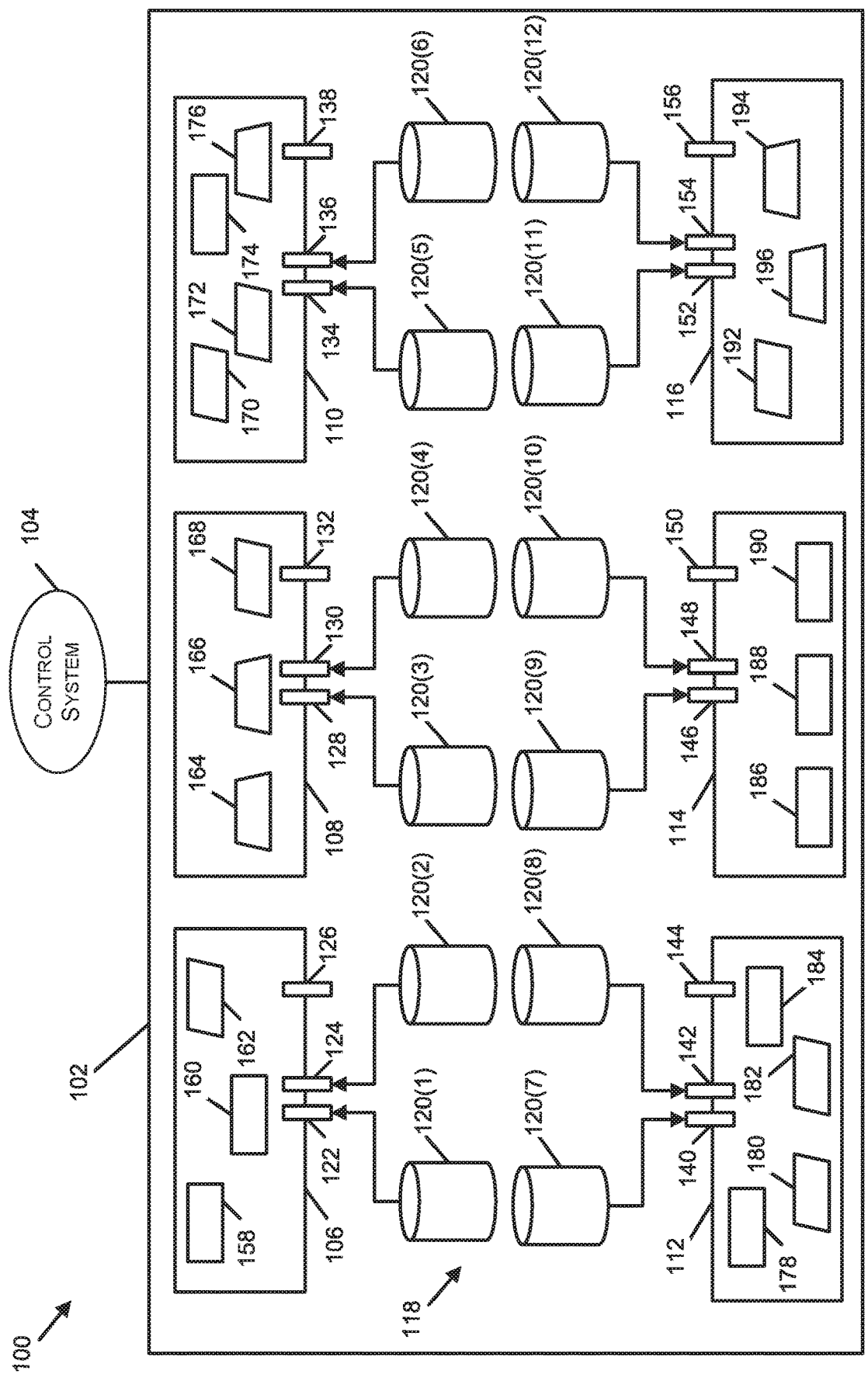
FIG. 1 is a diagram of some implementations of an architecture to manufacture one or more biotherapeutics using equipment contained in a number of modular cleanrooms according to some implementations.

The concepts described herein are directed to implementations of production facilities that can produce molecules, such as biotherapeutic, that can be used to treat biological conditions. As used herein, "biotherapeutics" refers to molecules that are made using cells from living organisms, such as humans, animals, plants, fungi, or bacteria, to make a product that can treat a biological condition. The biotherapeutics can include various molecules, such as proteins, enzymes, and antibodies. Also, as used herein, "biological condition" can refer to an abnormality of function and/or structure in an individual to such a degree as to produce or threaten to produce a detectable feature of the abnormality. A biological condition can be characterized by external and/or internal characteristics, signs, and/or symptoms that indicate a deviation from a biological norm in one or more populations. A biological condition can include at least one of one or more diseases, one or more disorders, one or more injuries, one or more syndromes, one or more disabilities, one or more infections, one or more isolated symptoms, or other atypical variations of biological structure and/or function of individuals.

The production facilities described herein can include a number of separate modular cleanrooms that comprise particular pieces of equipment to perform one or more aspects of the processes used to manufacture biotherapeutics. The modular cleanrooms are arranged such that material that is produced by the equipment of one modular cleanroom can be transferred to another modular cleanroom for additional processing. The modular cleanrooms can provide sterile, cleanroom environments having less than 0.5 micrometers (µm) particles per 100 ft$^3$ to 0.5 µm particles per 1,000,000 ft³. Additionally, the transfer of material between modular cleanrooms can take place without contamination of the material being transferred.

The separate modular cleanrooms can include equipment that perform operations related to solution preparation, inoculum preparation, cell culture, purification, and end product fill and finish. In some examples, the modular cleanrooms can utilize various cart pumps, bioreactors, chromatography systems, perfusion systems, mixing vessels, filtration devices, temperature control devices, testing devices, and material storage containers. Materials can be fed into the modular cleanrooms via airlocks that are coupled to storage containers. The storage containers can be located in a staging area of the production facility. In various implementations, the storage containers can include buffer solutions, intermediate products, end products, feed stock, material that has been removed in conjunction with a bleed operation, material used to feed cells utilized in the manufacturing process, such as glucose, or combinations thereof. The modular cleanrooms can also include materials transfer airlocks and changing rooms for personnel to wear clothing that complies with the standards for the modular cleanroom.

The equipment included in individual modular cleanrooms can be modified based on the product that is being manufactured. For example, a modular cleanroom that is configured to manufacture a first biotherapeutic using a perfusion system can be modified to manufacture a second biotherapeutic using a batch process. In another example, a modular cleanroom that performs purification operations using ion exchange chromatography columns to produce a first biotherapeutic can be modified to utilize affinity chromatography techniques to produce a second biotherapeutic. Thus, to produce a new biotherapeutic, the equipment located within one or more modular cleanrooms can be modified to correspond with the footprint needed to produce the new biotherapeutic. In this way, the production facilities described herein provide flexibility in the equipment that can be utilized in the production facility and, accordingly, a single production facility can be used to produce multiple biotherapeutics without a large capital expenditure to retrofit the production facility. Furthermore, in situations where additional capacity is needed, additional modular cleanrooms can be added to the production facility to increase the production of a biotherapeutic. In certain implementations, single use materials and corresponding equipment can be utilized in the production of biotherapeutics. By utilizing single use materials with certain equipment, contamination of the system can be minimized and manufacturing costs can also be minimized due to the decreased amount of cleaning and maintenance needed to operate single use equipment.

Also described herein, are systems and techniques to control and optimize the manufacturing of biotherapeutics. Data obtained from production lines can be analyzed using machine learning techniques to identify process variables that are statistically significant with respect to productivity metrics. The productivity metrics can include viable cell density, yield, and purity. In addition, data obtained from production lines can be analyzed using machine learning techniques to determine control variables that can be modified to impact one or more process variables. The process variables can be dependent on the control variables. That is, a modification to one or more control variables can cause a change in one or more process variables. In an illustrative example, changing the flow rate through a chromatography system can impact the carbon dioxide levels at one or more points along a production line for a biotherapeutic. In another illustrative example, modifying a temperature of the effluent of a bioreactor can impact the dissolved oxygen levels of the effluent. In an additional example, a rate of agitation in a bioreactor can impact the viable cell density of the end product of the production line.

In conventional biotherapeutic production lines, due to the unpredictable nature of biochemical processes, process variables that impact productivity metrics for the production lines are typically determined based on anecdotal evidence and, often, process variables that impact a productivity metric can be overlooked. Additionally, the control variables that can be modified to impact the process variables can also be difficult to identify in conventional systems and are typically identified through trial and error and/or after a production lapse has occurred. The techniques and systems described herein are directed to a proactive approach that identifies when process variables may be out of a threshold range of values and determines control variables that can be modified to keep the process variables within their operating range.

Furthermore, conventional production lines for biotherapeutics are often constructed in a customized manner and produce a single biotherapeutic on a relatively large scale (e.g., 5000 L or 10,000 L bioreactors) for a period of several years. Thus, data for process variables and control variables for additional production lines for a particular biotherapeutic are typically unavailable. Accordingly, the data used to determine settings for control variables is limited to the data collected from a single production line. The limited amount of information available to analyze in order to identify process variables and their respective control variables that impact productivity of a production line can result in some significant process variables and/or control variables going unidentified or not being identified until a lapse in production of the biotherapeutic takes place.

The systems and techniques described herein can obtain data from a number of production lines that have been constructed using modular cleanrooms. The similarities between the equipment and process flow of production lines constructed using modular cleanrooms can increase the amount of data available to analyze with respect to the productivity of the production lines. In this way, the process variables and control variables for the individual production lines can be identified more readily than conventional production lines for biotherapeutics. Additionally, analyzing a greater quantity of data than is available from conventional systems results in a more accurate identification of process variables and their respective control variables and in less time than conventional systems.

FIG. 1 is a diagram of some implementations of an architecture 100 to manufacture one or more biotherapeutics using equipment contained in a number of modular cleanrooms. The architecture 100 can include a production facility 102 that produces a biotherapeutic. In addition, the architecture 100 can include a control system 104 that determines information that can be utilized to control the operation of equipment included in the production facility 102. The control system 104 can obtain data from sensors that monitor conditions of a production line housed in the production facility 102. The control system 104 can also obtain data from testing and/or analysis of material extracted from the production line. For example, the control system 104 can obtain results from analytical tests performed on material extracted from various points on the production line.

The control system 104 can analyze the data obtained from the production facility 102 using one or more machine learning techniques. In particular implementations, the control system 104 can implement a partial least squares analysis to develop one or more models that predict one or more productivity metrics of the production line. For example, the control system 104 can develop a model to predict viable cell density of the production line. The model can include a number of process variables of the production line that impact the viable cell density of the production line. The control system 104 can also analyze the data obtained from the production facility 102 to determine one or more control variables that can have an effect on the process variables. The control system 104 can send control instructions to various pieces of equipment included in the production facility 102 in order to cause a change in values of one or more process variables. To illustrate, the control system 104 can determine that the viable cell density is outside of a threshold range and determine that pH of the material stored in a storage container is to be increased to bring the viable cell density back into the threshold range. Continuing with this example, the control system 104 can send instructions to a pump in the production facility 102 to add acid or base to the storage container in an amount that can modify the pH of the material stored in the storage container to a level that corresponds to a viable cell density that is within the threshold range.

In various implementations, the control system 104 can obtain data from a number of production facilities, including the production facility 102, to determine models to predict productivity metrics at the production facilities. In some cases, the control system 104 can develop a single model that can be used to predict a productivity metric at multiple production facilities for one or more biotherapeutics. For example, the control system 104 can determine a model to predict viable cell density for production lines of a biotherapeutic at multiple production facilities. In additional situations, the control system 104 can determine individual models to predict productivity metrics at a number of production facilities using data obtained from the number of production facilities. To illustrate, the control system 104 can determine a model to predict viable cell density at the production facility 102 based on data obtained from the production facility 102 and additional data obtained from additional production facilities.

The production facility 102 can include a number of modular cleanrooms that include equipment that is part of a production line to manufacture a biotherapeutic. Individual modular cleanrooms can include a subset of the equipment utilized to manufacture the biotherapeutic. Material produced by equipment from one of the modular cleanrooms can be transferred to another modular cleanroom for further processing until a final biotherapeutic is produced. In certain implementations, packaging or storing of the final biotherapeutic can take place in at least one of the modular cleanrooms.

In the illustrative implementation of FIG. 1, the production facility 102 includes a first modular cleanroom 106, a second modular cleanroom 108, a third modular cleanroom 110, a fourth modular cleanroom 112, a fifth modular cleanroom 114, and a sixth modular cleanroom 116. The individual modular cleanrooms 106, 108,110, 112, 114, 116 can comply with one or more international standards for airborne particular levels within the individual modular cleanrooms 106, 108, 110, 112, 114, 116. For example, the modular cleanrooms 106, 108, 110, 112, 114, 116 can comply with a class of cleanroom set forth by the International Organization for Standardization (ISO). The ISO classifications for cleanrooms specify a number of particles of a threshold size that can be present in a cleanroom. In a particular example, a cleanroom can be classified as an ISO 5 cleanroom with a maximum of 100,000 particles/m having a size no greater than 0.1 μm, a maximum of 23,700 particles/$m^3$ having a size no greater than 0.2 μm, a maximum of 10,200 particles/$m^3$ having a size no greater than 0.3 μm, a maximum of 3520 particles/$m^3$ having a size no greater than 0.5 μm, and a maximum of 832 particles/$m^3$ having a size no greater than 1 μm. The modular cleanrooms 106, 108, 110, 112, 114, 116 can also comply with other cleanroom standards, such as the European Union (EU) Good Manufacturing Practice (GMP) classifications for cleanrooms. In various implementations, individual modular cleanrooms of the modular cleanrooms 106, 108, 110, 112, 114, 116 can comply with the requirements of an ISO 5 class cleanroom, an ISO 6 class cleanroom, an ISO 7 class cleanroom, an ISO 8 class cleanroom, or an ISO 9 class cleanroom.

In illustrative examples, the production facility 102 can have an area from about 10,000 $ft^2$ to about 75,000 $ft^2$, an area from about 15,000 $ft^2$ to about 50,000 $ft^2$, or an area from about 20,000 $ft^2$ to about 30,000 $ft^2$. Additionally, the individual modular cleanrooms 106, 108, 110, 112, 114, 116 can have an area from about 400 $ft^2$ to about 2000 $ft^2$, from about 600 $ft^2$ to about 1,500 $ft^2$, or from about 700 $ft^2$ to about 1,000 $ft^2$. The production facility 102 can also include a staging area 118 that includes containers 120 that store materials that can be fed into the equipment included in one or more of the modular cleanrooms 106, 108, 110, 112, 114, 116. The staging area can include at least a portion of the production facility 102 that is not occupied by the modular cleanrooms 106, 108, 110, 112, 114, 116. In the illustrative example of FIG. 1, the staging area can include containers 120(1)-120(12) that are located within an interior portion of the production facility 102. In other implementations, one or more of the containers 120(1)-120(12) can be located in other portions of the production facility 102. For example, one or more of the containers 120(1)-120(12) can be located along a peripheral portion of the production facility 102 or located between adjacent modular cleanrooms, such as between modular cleanroom 106 and modular cleanroom 108. Furthermore, although the production facility 102 shown in the illustrative example of FIG. 1 has 12 containers 120, in other implementations, the production facility 102 can include more containers or fewer containers. In addition to the staging area 118 and the modular cleanrooms 120, the production facility 102 can include other areas not shown in FIG. 1, such as lobbies, meeting rooms, utility space, warehouse storage, quality control facilities, administrative offices, combinations thereof, and so forth.

The material stored in the containers 120 can be fed into the individual modular cleanrooms 106, 108, 110, 112, 114, 116 via various inlet ports that are included in the modular cleanrooms 106, 108, 110, 112, 114, 116. For example, the material from container 120(1) can be fed into the modular cleanroom 106 via an inlet port 122 and the material from the container 120(2) can be fed into the cleanroom 106 via an inlet port 124. The modular cleanroom 106 can also include an additional port 126 that can be used to transfer material into or out of the modular cleanroom 106. For example, material produced by one or more pieces of equipment in the modular cleanroom 106 can be transferred to a storage container (not shown in FIG. 1) or to another modular cleanroom via the additional port 126. Additionally, the modular cleanroom 108 can include inlet ports 128 and 130 that can pass material from the containers 120(3) and 120(4), respectively, into the modular cleanroom 108. The modular cleanroom 108 can also include the additional port 132 for transferring material into or out of the modular cleanroom 108. Further, the modular cleanroom 110 can include inlet ports 134, 136 and the additional port 138 and the modular cleanroom 112 can include inlet ports 140, 142 and the additional port 144. Also, the modular cleanroom 114 can include inlet ports 146, 148 and additional port 150 while the modular cleanroom 116 can include inlet ports 152, 154 and additional port 156. The inlet ports 134, 136 of the modular cleanroom 110 can be coupled to the containers 120(5) and 120(6), respectively, and the inlet ports 140, 142 of the modular cleanroom 112 can be coupled to the containers 120(7) and 120(8), respectively. The additional ports 138 and 144 can be used to transfer material into or out of the modular cleanrooms 110 and 112. In addition, the inlet ports 146, 148 of the modular cleanroom 114 can be coupled to the containers 120(9) and 120(10) and the inlet ports 152, 154 of the modular cleanroom 116 can be coupled to the containers 120(11) and 120(12) while the additional ports 150 and 156 can be used to transfer material into and out of the modular cleanrooms 114, 116. Although in the illustrative example of FIG. 1, the modular cleanrooms 106, 108, 110, 112, 114, 116 have two inlet ports and an additional port, in other implementations, the modular cleanrooms 106, 108, 110, 112, 114, 116 can have more or fewer inlet ports and/or more or fewer additional ports.

The modular cleanrooms 106, 108, 110, 112, 114, 116 can include various arrangements of equipment that are included in a production line for a biotherapeutic. In the illustrative example of FIG. 1, the modular cleanrooms 106, 108, 110, 112, 114, 116 can include different pieces of equipment that perform different operations in the manufacturing of a biotherapeutic. For example, the modular cleanroom 106 can include equipment 158, 160, 162 and the modular cleanroom 108 can include equipment 164, 166, 168. In addition, the modular cleanroom 110 can include equipment 170, 172, 174, 176 and the modular cleanroom 112 can include equipment 178, 180, 182, 184. Further, the modular cleanroom 114 can include equipment 186, 188, 190 and the modular cleanroom 116 can include equipment 192, 194, 196, 198. Although the illustrative example of FIG. 1 shows a particular number of pieces of equipment in the modular cleanrooms 106, 108, 110, 112, 114, 116, in other scenarios, the modular cleanrooms 106, 108, 110, 112, 114, 116 can include greater or fewer pieces of equipment. Additionally, the modular cleanrooms 106, 108, 110, 112, 114, 116 can include other features besides the equipment, such as material exchange airlocks, changing areas, integrity testing equipment, office furniture, laboratory equipment, computing devices, combinations thereof, and the like.

In illustrative examples, the modular cleanroom 106 can be a solution preparation area and the equipment 158, 160, 162 can be used to produce solutions that are used in the manufacturing of a biotherapeutic. For example, the equipment 158, 160, 162 can include one or more storage containers, one or more ventilation hoods, combinations thereof, and the like. In addition, the modular cleanroom 108 can be an inoculum preparation area and the equipment 164, 166, 168 can be used to produce inoculum that is later used to manufacture a biotherapeutic. In some situations, a cell line used to manufacture a biotherapeutic can be produced using the equipment 164, 166, 168. In various examples, the equipment 164, 166, 168 can include one or more reactors, one or more incubators, one or more refrigerators, testing equipment, combinations thereof, and so forth.

The modular cleanroom 110 can be a cell culture area that produces media that includes the biotherapeutic. The equipment 170, 172, 174, 176 can include one or more bioreactors, one or more perfusion systems, one or more chromatography systems, one or more filtration systems, one or more storage containers, one or more temperature control devices, one or more pumping systems, combinations thereof, and the like. In certain implementations, viral inactivation processes can be performed by equipment included in the modular cleanroom 110. Additionally, the modular cleanroom 112 can be a purification area where the product manufactured in a bioreactor of the modular cleanroom 110 can be purified. The purification of the product manufactured in the modular cleanroom 108 can be performed by separating different molecules included in the effluent of a bioreactor of the modular cleanroom 108. In particular implementations, one or more chromatographic processes can be used to purify the bioreactor product. The equipment 178, 180, 182, 184 included in the modular cleanroom 112 can include one or more chromatography systems, one or more filters, one or more storage containers, one or more pumping systems, one or more temperature control devices, combinations thereof, and so forth.

The modular cleanroom 114 can be a second purification area that further purifies the effluent from the bioreactor of the modular cleanroom 108. In particular implementations, the equipment 186, 188, 190 can include one or more filtering systems, one or more pumping systems, one or more storage containers, one or more temperature control devices, combinations thereof and so forth. In certain non-limiting implementations, the purification operations performed by the equipment of the modular cleanroom 114 can be optional. Further, the modular cleanroom 116 can include a biotherapeutic area where the biotherapeutic produced in the modular cleanroom 108 is readied for transport, delivery to a patient, and/or pre-processed before being provided to a facility that may modify the biotherapeutic to a form for delivery to a patient. In various implementations, the biotherapeutic can include sterile-filtered solutions and diluents. In non-limiting examples, the biotherapeutic may not include suspensions, vaccines, or biologics. In particular implementations, the biotherapeutic can be placed into vials and/or syringes. The equipment 192, 194, 196 can include one or more pumping devices, one or more storage containers, or one or more filling systems. The one or more filling systems can be used to dispense an amount of the biotherapeutic into a vessel, such as a vial or syringe.

Although the illustrative example of FIG. 1 includes six modular cleanrooms, the production facility 102 can include more modular cleanrooms or fewer modular cleanrooms. In certain implementations, the production facility 102 can include additional modular cleanrooms that include cell culture areas. Also, the production facility 102 can include additional modular cleanrooms that include equipment that performs purification operations and/or filtering operations.

Figure 2:
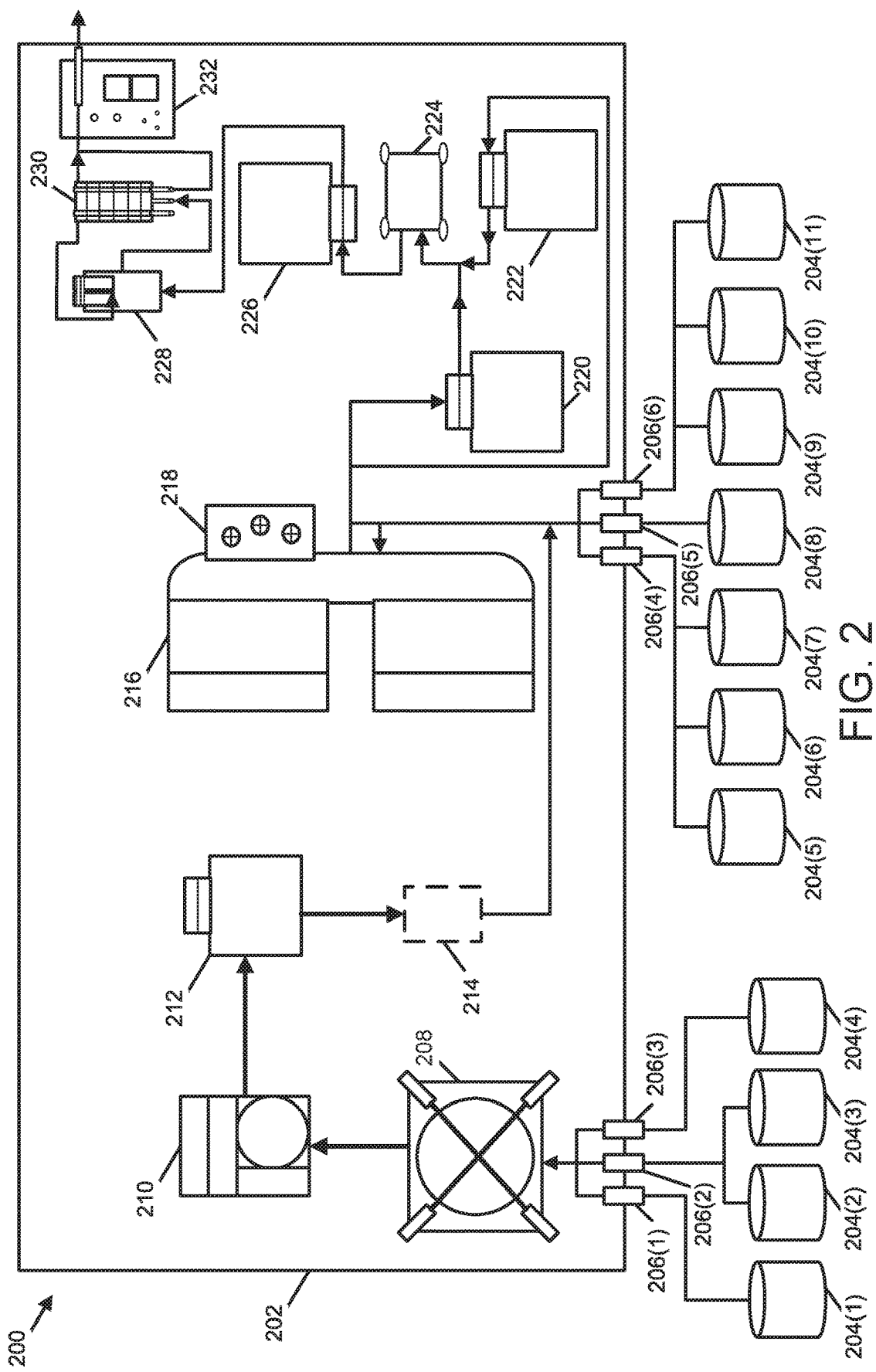
FIG. 2 is a schematic diagram of implementations of an environment that includes a modular cleanroom that can produce a virally inactivated pool according to some implementations.

FIG. 2 is a schematic diagram of implementations of an environment 200 that includes a modular cleanroom 202 that can produce a virally inactivated pool. In various implementations, the environment 200 can be included in a production facility, such as the production facility 102 of FIG. 1. The modular cleanroom 202 can include equipment that can be used to perform cell culture operations. The cell culture operations can cause a biotherapeutic to be produced using media that includes a cell line that can support the production of the biotherapeutic.

The modular cleanroom 202 can be coupled to a number of storage containers 204. The storage containers 204 can store material that is fed into one or more pieces of equipment included in the modular cleanroom 202 and/or material that is transferred out of one or more pieces of equipment housed in the modular cleanroom 202. In particular implementations, the storage containers 204 can be located in a staging area of a production facility. The storage containers 204 can have various capacities. For example, individual storage containers can have capacities from about 50 L to about 2000 L or from about 100 L to about 1000 L. In illustrative examples, one or more first containers 204 can have a capacity of about 100 L, one or more second containers 204 can have a capacity of about 200 L, and one or more third containers 204 can have a capacity of about 1000 L.

Material can be transferred between equipment located in the modular cleanroom 202 and the storage containers 204 via ports 206. In the illustrative example of FIG. 2, the environment 200 can include a storage container 204(1) coupled to a port 206(1), storage containers 204(2) and 204(3) coupled to a port 206(2), and a storage container 204(4) coupled to a port 206(3). The ports 206(1), 206(2), and 206(3) can be coupled to a bioreactor 208. In illustrative examples, the storage containers 204(1) and 204(4) can provide cell culture media to the bioreactor 208. Additionally, the storage container 204(2) can provide sodium bicarbonate to the bioreactor 208 and the storage container 204(3) can provide a cell growth material, such as glucose, to the bioreactor 208. In alternative implementations, the storage container 204(3) can store material that has been removed from the bioreactor 208 as part of a cell bleed operation.

The bioreactor 208 can include a vessel having a capacity from about 250 L to about 2000 L or from about 500 L to about 1000 L. The bioreactor 208 can include a pumping mechanism, an agitation mechanism, a sparger, combinations thereof, and the like. Conditions within the bioreactor 208 can be suitable to cause a biological reaction to take place that produces a specified biotherapeutic using cell culture media fed into the bioreactor 208 from one or more of the storage containers 204. The bioreactor 208 can operate on a continuous basis without shutting down for a period of time. To illustrate, the bioreactor 208 can operate for a duration from about 5 days to about 40 days, from about 10 days to about 30 days, or from about 15 days to about 25 days. Although the illustrative example of FIG. 2 shows a single bioreactor 208 housed within the modular cleanroom 202, in additional implementations, the modular cleanroom 202 can house two or more bioreactors.

In illustrative examples, for a single vessel volume, the bioreactor 208 can produce from about 0.5 g of biotherapeutic per liter of cell culture media per day to about 10 g of biotherapeutic per liter of cell culture media per day, from about 1 g of biotherapeutic per liter of cell culture media per day to about 6 g of biotherapeutic per liter of cell culture media per day, or from about 2 g of biotherapeutic per liter of cell culture media per day to about 4 g of biotherapeutic per liter of cell culture media per day. In other illustrative examples, for two vessel volumes, the bioreactor 208 can produce from about 0.25 g of biotherapeutic per liter of cell culture media per day to about 7 g of biotherapeutic per liter of cell culture media per day, from about 0.5 g of biotherapeutic per liter of cell culture media per day to about 5 g of biotherapeutic per liter of cell culture media per day, or from about 1 g of biotherapeutic per liter of cell culture media per day to about 2 g of biotherapeutic per liter of cell culture media per day. Although not shown in the illustrative example of FIG. 2, the bioreactor 208 can be coupled to, or otherwise include, a temperature control system and/or a human machine interface device.

The bioreactor 208 can be coupled to a perfusion system 210 that can utilize one or more pumping devices to add feed material to the bioreactor 208 and remove effluent from the bioreactor 208. The perfusion system 210 can provide effluent to a storage container 212. The effluent stored in the storage container 212 can be obtained by a continuous chromatography system 216. Optionally, the effluent stored in the storage container 212 can pass through a temperature control system 214 that can modify a temperature of the effluent before the effluent is provided to the continuous chromatography system 216. In illustrative examples, the temperature control system 214 can include a heat exchanger that can heat or cool the effluent stored in the storage container 212 as the effluent is transported to the continuous chromatography system 216. The continuous chromatography system 216 can include a group of chromatography columns 218. In various implementations, the group of chromatography columns 218 can include from 2 to 16 chromatography columns or from 3 to 9 chromatography columns. Additionally, in particular implementations, the continuous chromatography system 216 can have a disposable flow path, such that the continuous chromatography system 216 is a single use, continuous chromatography system.

The continuous chromatography system 216 can utilize various chromatographic processes. For example, the continuous chromatography system 216 can utilize one or more of Protein A affinity chromatographic processes, ion exchange chromatographic processes, mixed mode chromatographic processes, hydrophobic interaction chromatographic processes, or size exclusion chromatographic processes. In various implementations, the columns 218 of the continuous chromatography system 216 can have a diameter from about 40 cm to about 100 cm, from about 50 cm to about 80 cm, or from about 60 cm to about 70 cm. Additionally, in particular implementations, the columns 218 of the continuous chromatography system 216 can have a height from about 10 cm to about 40 cm, from about 15 cm to about 30 cm, or from about 20 cm to about 25 cm. In certain implementations, an amount of product produced by each column 218 of the continuous chromatography system 216 can be from about 80 g/L resin to about 140 g/L resin, from about 90 g/L resin to about 130 g/L resin, or from about 100 g/L resin to about 120 g/L resin. Further, effluent from the bioreactor 208 can be processed according to a number of cycles of the continuous chromatography system 216, such as from 4 to 15 cycles, from 6 to 12 cycles, or from 8 to 10 cycles. In illustrative examples, individual cycles of the continuous chromatography system 216 can have a duration from about 3 hours to about 12 hours, from about 4 hours to about 10 hours, or from about 6 hours to about 8 hours.

Buffer solution can be fed into the continuous chromatography system 216 from one or more of containers 204(5), 204(6), 204(7), 204(8), 204(9), 204(10), or 204(11) via ports 206(4), 206(5), and/or 206(6). In the illustrative example of FIG. 2, the containers 204(5), 204(6), and 204(7) can be coupled to port 206(4), container 204(8) can be coupled to port 206(5), and the containers 204(9), 204(10), and 204(11) can be coupled to port 206(6). Other implementations can include different arrangements of containers coupled to one or more of the ports 206(4), 206(5), and/or 206(6). In addition, although not shown in FIG. 2, a portion of the effluent from the continuous chromatography system 216 can be transported to one or more of the containers 204(5), 204(6), 204(7), 204(8), 204(9), 204(10), or 204(11).

The effluent from the continuous chromatography system 216 can be fed into a series of devices including a container 220, a container 222, a pumping device 224, and an additional container 226. In particular implementations, effluent from the continuous chromatography system 216 can be supplied to either the container 220 or the container 222. For example, the delivery of the effluent from the continuous chromatography system 216 can be alternated between the container 220 and the container 222. To illustrate, effluent from the continuous chromatography system 216 can be supplied to the container 220 for a period of time or until the volume of the effluent stored in the container 220 reaches a threshold level. After the period of time has expired or the volume of the effluent in the container 220 reaches at least the threshold level, the effluent from the continuous chromatography system 216 can be supplied to the container 222. Subsequently, the effluent from the continuous chromatography system 216 can be switched back to being supplied to the container 220 after the effluent from the continuous chromatography system 216 has been supplied to the container 222 for a period of time or the volume of the effluent in the container 222 reaches a threshold volume. The filling of one of containers 220, 222 and switching to the other of the containers 220, 222 with the effluent of the continuous chromatography system 216 can continue until the bioreactor 208 no longer produces product. At least one of the container 220 or the container 222 can collect product from the continuous chromatography system 216 for at least one day, at least 2 days, at least 3 days, at least 4 days, at least 5 days, at least 6 days, at least 7 days, or at least 8 days. In illustrative examples, at least one of the container 220 or the container 222 can collect product from the continuous chromatography system 216 for 0.5 days to 25 days, 1 day to 20 days, 2 days to 15 days, 3 days to 10 days, 4 days to 8 days, 5 days to 12 days, or 6 days to 15 days. In particular illustrative examples, the container 220 or the container 222 can have a volume of about 100 liters and collect product from the continuous chromatography system 216 for about 5 days.

The modular cleanroom 202 can also include a pump device 224. The pump device 224 can be used to add acid to the effluent from the continuous chromatography system 216. The addition of acid to the effluent from the continuous chromatography system 216 can be used as a viral inactivation process. In some implementations, the effluent from the continuous chromatography system 216 can be provided to the container 226 from the container 220 or container 222 before the acid is added to the effluent. In additional implementations, the pump device 224 can add acid to the effluent from the continuous chromatography system 216 while the effluent is stored in the container 220 or the container 222. In these situations, as effluent is being provided to one of the containers 220, 222 from the continuous chromatography system 216, the pump device 224 can add acid to the other of the containers 220, 222 to virally inactivate the effluent from the continuous chromatography system 216 being store therein. The effluent from the continuous chromatography system 216 can be treated with acid provided by the pump device 224 for a period of time to achieve viral inactivation of the effluent of the continuous chromatography system 216. For example, the effluent of the continuous chromatography system 216 can be treated with acid provided by the pump device 224 for at least 5 hours, at least 10 hours, at least 15 hours, at least 20 hours, at least 30 hours, at least 40 hours, at least 4 days, or at least 5 days. In illustrative scenarios, the effluent of the continuous chromatography system 216 can be treated with acid provided by the pump device 224 for 4 hours to 6 days, from 12 hours to 5 days, from 1 day to 4 days, from 18 hours to 3 days, or from 2 days to 5 days. In further implementations, instead of treating the effluent from the continuous chromatography system 216 with an acid, the effluent from the continuous chromatography system 216 can be treated with a detergent to produce the virally inactivated pool.

The virally inactivated pool can be pumped out of the modular cleanroom 202 using a pump 228 that sends the virally inactivated pool through a depth filter 230 and filter cart 232. The filter cart 232 can include a filter device having an average opening size of no greater than 1 micron, no greater than 0.8 microns, no greater than 0.6 microns, no greater than 0.4 microns, no greater than 0.2 microns, no greater than 0.1 microns, or no greater than 0.05 microns. In illustrative examples, the filter device of the filter cart can have openings with an average size from 0.05 microns to 1 micron, from 0.1 microns to 0.6 microns, or from 0.2 microns to 0.4 microns. After being pumped out of the modular cleanroom 202, the virally inactivated pool can be stored in a container (not shown) before being provided to an additional modular cleanroom included in a production facility.

Figure 3:
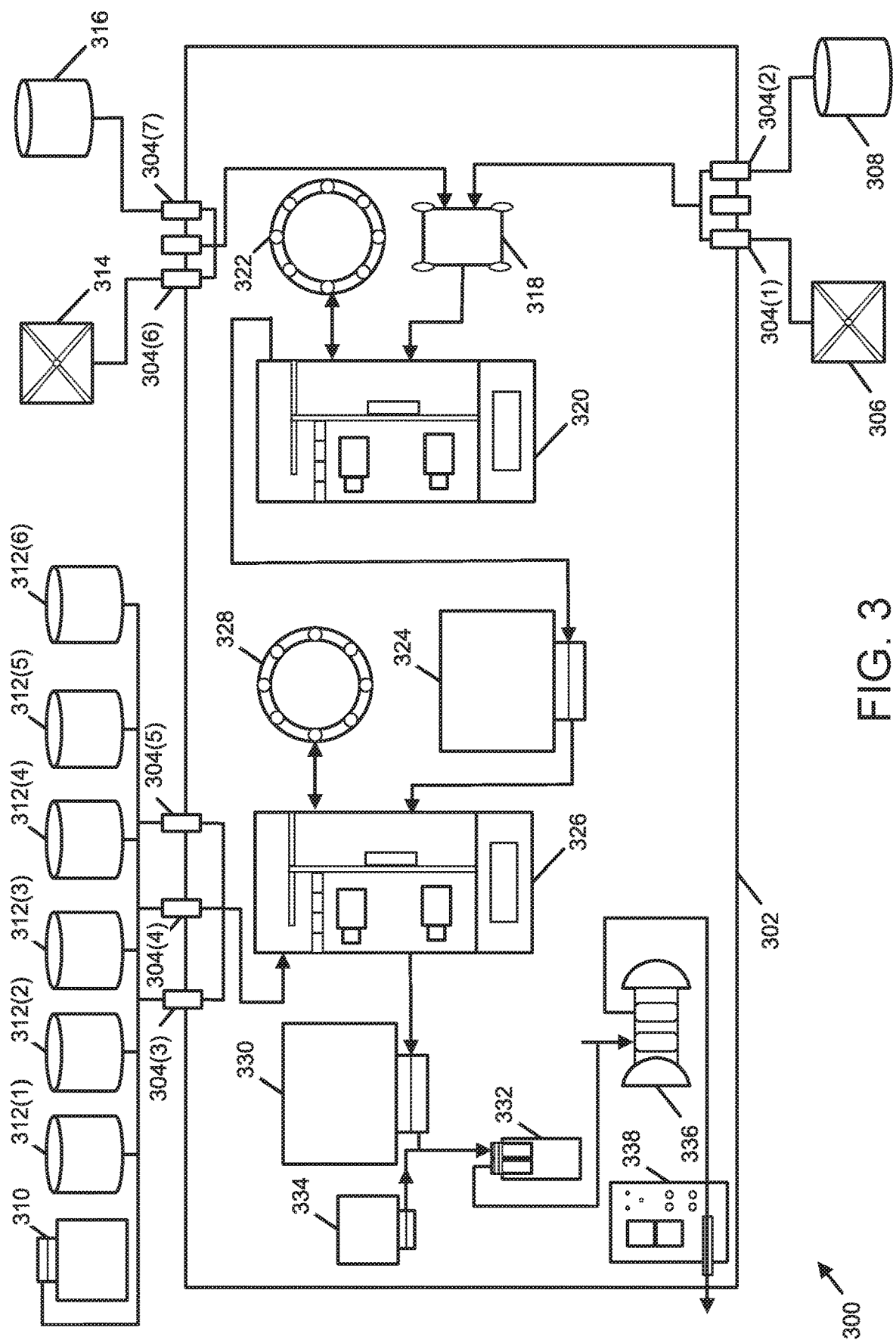
FIG. 3 is a schematic diagram of implementations of an environment that includes a modular cleanroom that can produce a viral filtered biotherapeutic according to some implementations.

FIG. 3 is a schematic diagram of implementations of an environment 300 that includes a modular cleanroom 302 that can produce a viral filtered biotherapeutic. In various implementations, the environment 300 can be included in a production facility, such as the production facility 102 of FIG. 1. The modular cleanroom 302 can include equipment to perform operations in the production of a viral filtered biotherapeutic using the virally inactivated pool produced by the modular cleanroom 202. For example, the modular cleanroom 302 can include equipment to perform purification operations with respect to the virally inactivated pool produced by the modular cleanroom 202.

The modular cleanroom 302 can include a number of ports 304 that can be coupled to containers that supply various solutions to equipment included in the modular cleanroom. In the illustrative example of FIG. 3, the modular cleanroom 302 can include a first port 304(1) coupled to a first storage container 306 and a second port 304(2) coupled to a second storage container 308. The first storage container 306 can store an amount of the virally inactivated elution pool produced by the modular cleanroom 202. Additionally, the second container 308 can store an amount of buffer solution that can be utilized by one or more pieces of equipment of the modular cleanroom 302. The first storage container 306 can have a volume from 1000 L to 3000 L, from 1500 L to 2500 L, or from 1750 L to 2250 L. Further, the second storage container 308 can have a volume from 500 L to 2000 L, from 750 L to 1500 L, or from 800 L to 1200 L.

The modular cleanroom 302 can also include a third port 304(3), a fourth port 304(4), and a fifth port 304(5). The ports 304(3), 304(4), 304(5) can be coupled to additional buffer storage containers 310, 312(1), 312(2), 312(3), 312(4), 312(5), and 312(6). The buffer storage containers 312 can have different volumes from the buffer storage container 310. To illustrate, the buffer storage container 310 can have a volume from 50 L to 250 L or from 100 L to 200 L. Additionally, the storage containers 312 can have volumes from 500 L to 2000 L, from 750 L to 1500 L, or from 800 L to 1200 L.

In addition, the modular cleanroom 302 can include a sixth port 304(6) coupled to a third storage container 314 and a fourth storage container 316. The third storage container 314 can store an amount of virally inactivated pool produced by the modular cleanroom 202 and the fourth storage container 316 can include a buffer solution. The third storage container 314 can have a volume from 1000 L to 3000 L, from 1500 L to 2500 L, or from 1750 L to 2250 L and the fourth storage container 316 can have a volume from 500 L to 2000 L, from 750 L to 1500 L, or from 800 L to 1200 L. In illustrative examples, the storage containers 308, 310, 312, 316 that store buffer solution can store a sodium bicarbonate buffer solution. Also, the storage containers 306, 308, 310, 312, 314, 316 can be located in a staging area of a production facility. In particular implementations, at least a portion of the storage containers 306, 308, 310, 312, 314, 316 can be stored in the staging area along with at least a portion of the storage containers 204 of FIG. 2.

The virally inactivated pool from the containers 306, 314 and/or the buffer solution from the containers 308, 316 can be fed into a temperature control unit 318. The temperature control unit 318 can include a heat exchanger, in some implementations. Additionally, the temperature control unit 318 can be portable. In particular implementations, the temperature control unit 318 can be optional depending on the temperature of the virally inactivated pool and the temperature of the buffer solution.

The virally inactivated pool and buffer solutions at appropriate temperatures can be fed into a first chromatography system 320 that includes a number of chromatography columns 322. In various implementations, the number of chromatography columns 322 utilized for a given process can include from 2 to 16 chromatography columns or from 3 to 8 chromatography columns. In some implementations, the first chromatography system 320 can have a disposable flow path, such that the first chromatography system 320 is a single use chromatography system. The first chromatography system 320 can utilize various chromatographic processes. For example, the first chromatography system 320 can utilize one or more of Protein A affinity chromatographic processes, ion exchange chromatographic processes, mixed mode chromatographic processes, hydrophobic interaction chromatographic processes, size exclusion chromatographic processes, or ion exchange chromatographic processes. In various implementations, the columns 322 of the first chromatography system 320 can have a diameter from about 40 cm to about 100 cm, from about 50 cm to about 80 cm, or from about 60 cm to about 70 cm. Additionally, the columns 322 of the first chromatography system 320 can have a height from about 10 cm to about 40 cm, from about 15 cm to about 30 cm, or from about 20 cm to about 25 cm. In certain implementations, an amount of product produced by each column 322 of the first chromatography system 320 can be from about 80 g/L resin to about 140 g/L resin, from about 90 g/L resin to about 130 g/L resin, or from about 100 g/L resin to about 120 g/L resin. Further, virally inactivated pool can be processed according to a number of cycles of the first chromatography system 320, such as from 4 to 15 cycles, from 6 to 12 cycles, or from 8 to 10 cycles. In illustrative examples, individual cycles of the first chromatography system 320 can have a duration from about 3 hours to about 12 hours, from about 4 hours to about 10 hours, from about 6 hours to about 8 hours, or from about 3 hours to about 6 hours.

The purified product from the first chromatography system 320 can be stored in a storage container 324. The storage container 324 can have a volume from 100 L to 1500 L, from 250 L to 1250 L, from 500 L to 1000 L, or from 600 L to 700 L. The purified product from the first chromatography system 320 stored in the storage container 324 can be fed to an additional chromatography system 326 having a number of columns 328. Buffer solution can also be fed into the additional chromatography system 326 from the containers 310, 312. The additional chromatography system 326, in some implementations, can have a similar configuration as the first chromatography system 320. Depending on a purity of the product produced by the first chromatography system 320, the second chromatography system 326 can be optionally implemented.

In particular implementations, the number of chromatography columns 328 utilized for a given process can include from 2 to 16 chromatography columns or from 3 to 8 chromatography columns. In some implementations, the additional chromatography system 326 can have a disposable flow path, such that the additional chromatography system 326 is a single use chromatography system. The additional chromatography system 326 can utilize various chromatographic processes. For example, the additional chromatography system 326 can utilize one or more of Protein A affinity chromatographic processes, ion exchange chromatographic processes, mixed mode chromatographic processes, hydrophobic interaction chromatographic processes, size exclusion chromatographic processes, or ion exchange chromatographic processes. In various implementations, the columns 328 of the additional chromatography system 326 can have a diameter from about 40 cm to about 100 cm, from about 50 cm to about 80 cm, or from about 60 cm to about 70 cm. Additionally, the columns 328 of the additional chromatography system 326 can have a height from about 10 cm to about 40 cm, from about 15 cm to about 30 cm, or from about 20 cm to about 25 cm. In certain implementations, an amount of product produced by each column 328 of the additional chromatography system 326 can be from about 80 g/L resin to about 140 g/L resin, from about 90 g/L resin to about 130 g/L resin, or from about 100 g/L resin to about 120 g/L resin. Further, purified product produced by the first chromatography system 320 can be processed according to a number of cycles of the additional chromatography system 326, such as from 4 to 15 cycles, from 6 to 12 cycles, or from 8 to 10 cycles. In illustrative examples, individual cycles of the additional chromatography system 326 can have a duration from about 3 hours to about 12 hours, from about 4 hours to about 10 hours, from about 6 hours to about 8 hours, or from about 3 hours to about 6 hours.

In particular implementations, the product purified by the additional chromatography system 326 can be stored in an additional storage container 330. The additional storage container 330 can have a volume from 100 L to 1500 L, from 250 L to 1250 L, from 500 L to 1000 L, or from 600 L to 700 L. The additional storage container 330 can be coupled with a pumping device 332 that is also coupled to a smaller storage container 334. The smaller storage container 334 can include additional solution that can be pumped by the pumping device 332, such as a buffer solution. The smaller storage container 334 can have a volume from 25 L to 250 L, from 35 L to 150 L, or from 40 L to 75 L.

The pumping device 332 can feed the product purified by the additional chromatography system 326 stored in the additional storage container 330 and/or the solutions stored by the smaller storage container 334 into a viral filtration device 336. The viral filtration device can have from 1 m² to 10 m² of filtration area, from 2 m² to 8 m² of filtration area, or from 3 m² to 6 m² of filtration area. The time for filtration of the product purified by the first chromatography system 320, and optionally by the second chromatography system 326, can be from 5 hours to 15 hours, from 7 hours to 12 hours, or from 8 hours to 10 hours. The viral filtered biotherapeutic from the viral filtration device 336 can be fed to a filter cart 338 to transport the viral filtered biotherapeutic out of the modular cleanroom 302.

Figure 4:
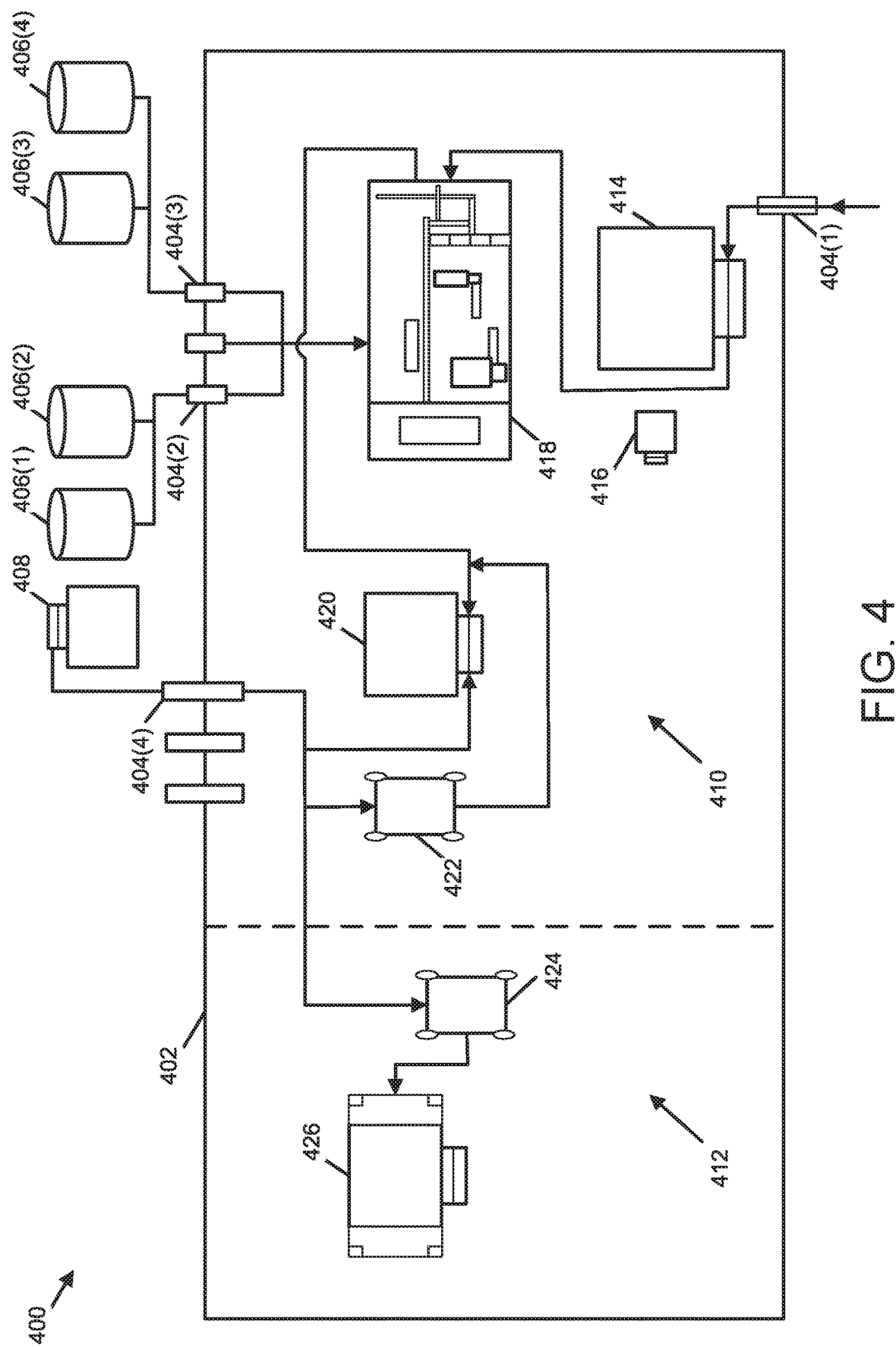
FIG. 4 is a schematic diagram of implementations of an environment that includes a modular cleanroom that can produce a purified biotherapeutic according to some implementations.

FIG. 4 is a schematic diagram of implementations of an environment 400 that includes a modular cleanroom 402 that can produce a purified biotherapeutic. In various implementations, the environment 400 can be included in a production facility, such as the production facility 102 of FIG. 1. The modular cleanroom 402 can include equipment to perform operations in the production of a purified biotherapeutic using the viral filtered biotherapeutic produced by the modular cleanroom 302. For example, the modular cleanroom 402 can include equipment to perform additional purification operations with respect to the viral filtered biotherapeutic produced by the modular cleanroom 302.

The modular cleanroom 402 can include a number of ports 404 that can be coupled to containers that supply various solutions to equipment included in the modular cleanroom 402. In the illustrative example of FIG. 4, the modular cleanroom 402 can include a first port 404(1) that supplies the viral filtered biotherapeutic produced by the modular cleanroom 302 to equipment located in the modular cleanroom 402 for further purification of the viral filtered biotherapeutic. In some implementations, the viral filtered biotherapeutic can be stored in a storage container that is coupled to the port 404(1). Additionally, the modular cleanroom 402 can include a second port 404(2) that is coupled to storage containers 406(1) and 406(2) and a third port 404(3) that is coupled to storage containers 406(3) and 406(4). The containers 408 can store an amount of buffer solution that can be utilized by one or more pieces of equipment of the modular cleanroom 402. The storage containers 406 can have a volume from 500 L to 2000 L, from 750 L to 1500 L, or from 800 L to 1200 L. Further, the modular cleanroom 402 can include a fourth port 404(4) that is coupled to a storage container 408 that can also store buffer solution that is to be fed to equipment in the modular cleanroom 402. The storage container 408 can have a volume from 50 L to 250 L or from 100 L to 200 L. In some implementations, the storage containers 406, 408 can be located in a staging area of a production facility, such as the production facility 102 of FIG. 1.

The modular cleanroom 402 can include two areas 410 and 412. At least portions of the two areas 410, 412 can be separated by a physical barrier. In particular implementations, the areas 410, 412 can be separated by curtains. In other implementations, the areas 410, 412 can be separated by at least a partial wall that allows access between the two areas 410, 412. The first area 410 can be a filtration area and the second area 412 can be a fill/finish area. In some implementations, at least a portion of the second area 412 can be located under a hood that allows laminar flow within the second area 412. In various implementations, the concentration of particles in the second area 412 may be less than the concentration of particles in the first area 410. In these situations, a cleanroom classification of the second area 412 can be different from a cleanroom classification of the first area 410.

The first area 410 of the modular cleanroom 402 can include a first storage container 414 that can store an amount of the viral filtered biotherapeutic from the modular cleanroom 302 and an additional storage container 416 that can store an amount of buffer solution. The first holding container 414 can have a volume from 200 L to 2000 L, from 400 L to 1500 L, or from 600 L to 1000 L. Additionally, the additional storage container 416 can have a volume from 25 L to 200 L, from 40 L to 150 L, or from 50 L to 100 L. The virally filtered product stored in the first holding container 414 can be fed, along with buffer solution from the additional storage container 416 in some situations, into a filtration device 418. The filtration device 418 can perform ultrafiltration and/or diafiltration operations. In particular implementations, the filtration device 418 can include a tangential flow filtration device. The filtration device 418 can include a number of membranes that separate molecules on the basis of the size of the pores of the membranes. Diafiltration can also be performed by the filtering device 418. Buffer solution obtained from one or more of the containers 406 can also be fed into the filtration device 416 to be used in the ultrafiltration/diafiltration processes. In particular implementations, the filtration device 416 can be coupled to a temperature control unit.

In illustrative examples, the filtration device 416 can include a filtration area from 2 $m^2$ to 20 $m^2$, from 4 $m^2$ to 15 $m^2$, or from 8 $m^2$ to 12 $m^2$. In addition, the filtration device 416 can be operated for a number of cycles. For example, the filtration device 416 can be operated for 2 to 12 cycles, 4 to 10 cycles, or 6 to 8 cycles to produce the purified biotherapeutic. Further, each cycle of the filtration device 416 can have a duration from 2 to 20 hours, from 4 to 15 hours, or from 6 to 10 hours. In various implementations, the total processing time at the filtration device 416 can be from 4 to 120 hours, from 10 to 100 hours, from 25 to 75 hours, or from 40 to 50 hours.

The filtered product from the filtration device 416 can be stored in an additional storage container 420. The additional storage container 420 can have a volume from 50 L to 1200 L, from 100 L to 750 L, or from 200 L to 400 L. In addition, the additional storage container 420 can be coupled to a first pump device 422 that can add buffer solution from the storage container 408 to the additional holding container 420. Further, the first pump device 422 can provide the purified biotherapeutic stored in the additional storage container 420 to a second pump device 424 that is located in the second area 412. The second pump device 424 can be coupled to a third storage container 426 located in the second area 412. The second pumping device 424 can be used to provide buffer solution to the purified biotherapeutic stored in the additional holding container 420. The third holding container can have a volume from 50 L to 1200 L, from 100 L to 750 L, or from 200 L to 400 L.

The purified biotherapeutic can undergo one or more fill and/or finish operations in the second area 412. The filling operations can be performed in an automated process where a number of vials are filled at a particular rate per minute. For example, the fill operations can take place at a rate of 5 to 100 vials per minute, 10 to 75 vials per minute, or 20 to 60 vials per minute. In illustrative examples, the vials can have volumes from 2 mL to 40 mL, from 5 mL to 30 mL, and from 10 mL to 20 mL.

Although the illustrative examples of FIGS. 2-4 are directed to a perfusion-based system to produce biotherapeutics, modular cleanrooms can also be utilized to produce biotherapeutics using batch processes. In these implementations, a modular cleanroom can include one or more bioreactors and the products produced by the one or more bioreactors can be stored in various storage containers. The product stored in the storage containers can then be fed into a first chromatography system. In various implementations, the product stored in the storage containers can be fed into an additional storage container coupled to a first chromatography system. The first chromatography system can, in some implementations, be located in the same modular cleanroom as the one or more bioreactors or in a separate modular cleanroom. The product stored in the additional storage container can be fed into the first chromatography system. After being purified by the first chromatography system, the purified product can be subjected to a viral inactivation process. The viral inactivated pool can then be sent to one or more additional modular cleanrooms, such as the modular cleanroom 300 of FIG. 3 and the modular cleanroom 400 of FIG. 4.

In illustrative examples, the pieces of equipment included in the modular cleanrooms 200, 300, 400 can include a production line to produce a biotherapeutic. In some implementations, the biotherapeutic can include a therapeutic protein. The term "therapeutic protein" means a pharmacologically active protein applicable to the prevention, treatment, or cure of a disease or condition of human beings. Examples of therapeutic proteins include, but are not limited to, monoclonal antibodies, recombinant forms of a native protein (e.g., a receptor, ligand, hormone, enzyme or cytokine), fusion proteins, peptibodies, and/or a monomer domain binding proteins, e.g., based on a domain selected from LDL receptor A-domain, thrombospondin domain, thyroglobulin domain, trefoiVPD domain, VEGF binding domain, EGF domain, Anato domain, Notch/LNR domain, DSL domain, integrin beta domain, and Ca-EGF domain. "Polypeptide" and "protein" are used interchangeably herein and include a molecular chain of two or more amino acids linked covalently through peptide bonds. The terms do not refer to a specific length of the product.

The term "recombinant" indicates that the material (e.g., a nucleic acid or a polypeptide) has been artificially or synthetically (i.e., non-naturally) altered by human intervention. The alteration can be performed on the material within, or removed from, its natural environment or state. The term "recombinant protein" or "recombinant polypeptide" as used herein refers to a protein molecule, e.g., a therapeutic protein of interest, which is expressed using a recombinant DNA molecule. A "recombinant host cell" is a cell that contains and/or expresses a recombinant nucleic acid.

The term "polynucleotide" or "nucleic acid" includes both single-stranded and double-stranded nucleotide polymers containing two or more nucleotide residues. The nucleotide residues comprising the polynucleotide can be ribonucleotides or deoxyribonucleotides or a modified form of either type of nucleotide. A "polynucleotide sequence" or "nucleotide sequence" or "nucleic acid sequence," as used interchangeably herein, is the primary sequence of nucleotide residues in a polynucleotide, including of an oligonucleotide, a DNA, and RNA, a nucleic acid, or a character string representing the primary sequence of nucleotide residues, depending on context. From any specified polynucleotide sequence, either the given nucleic acid or the complementary polynucleotide sequence can be determined. Included are DNA or RNA of genomic or synthetic origin which may be single- or double-stranded, and represent the sense or antisense strand. Unless specified otherwise, the left-hand end of any single-stranded polynucleotide sequence discussed herein is the 5'end; the left-hand direction of double-stranded polynucleotide sequences is referred to as the 5' direction.

An expression cassette is a typical feature of recombinant expression technology. The expression cassette includes a gene encoding a protein of interest, e.g., a gene encoding an antibody sequence, such as an immunoglobulin light chain and/or heavy chain sequence. A eukaryotic "expression cassette" refers to the part of an expression vector that enables production of protein in a eukaryotic cell, such as a mammalian cell. It includes a promoter, operable in a eukaryotic cell, for mRNA transcription, one or more gene(s) encoding protein(s) of interest and a mRNA termination and processing signal. Recombinant expression technology typically involves the use of a recombinant expression vector comprising an expression cassette and a mammalian host cell comprising the recombinant expression vector with the expression cassette or at least the expression cassette, which may for example, be integrated into the host cell genome.

The term "vector" means any molecule or entity (e.g., nucleic acid, plasmid, bacteriophage or virus) used to transfer protein coding information into a host cell.

The term "expression vector" or "expression construct" as used herein refers to a recombinant DNA molecule containing a desired coding sequence and appropriate nucleic acid control sequences necessary for the expression of the operably linked coding sequence in a particular host cell.

"Cell," "cell line," and "cell culture" are often used interchangeably and all such designations herein include cellular progeny.

Biotherapeutics produced herein can be produced by culturing protein-secreting mammalian cells in one or more single-use perfusion bioreactors comprising a liquid culture medium under conditions that allow the cells to secrete the recombinant therapeutic protein into the medium for a production cultivation period of at least 20 days.

A "cell culture" means the extracellular culture medium (fresh or conditioned) and the mammalian cells cultured therein. "Cell culture medium" or "culture medium," used interchangeably herein, is a sterile aqueous medium suitable for growth of cells, and preferably animal cells, more preferably mammalian cells (e.g., CHO cells), in in vitro cell culture. "Feed medium" is fresh cell culture medium added to a cell culture after inoculation of the cells into the cell culture medium and cell growth has been commenced.

The term "production cultivation period" means the period during which recombinant therapeutic protein-secreting mammalian cells are kept under incubation conditions in the bioreactor(s) which physiologically permit the continued production of the therapeutic protein of interest. In various implementations, the production cultivation period can be at least 10 days, or more, or at least 20 days, or more, e.g., 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or more; or 10-20 days, or more, or 20-30 days, or more, or 30-45 days, or more, or 45-60 days, or more.

During the production cultivation period, fresh sterile liquid culture medium is automatically added into the one or more perfusion bioreactors, mixed contemporaneously from a plurality of different concentrated medium component solutions and an aqueous diluent. The phrase "mixed contemporaneously" means that the concentrated medium components and diluent are mixed together to make fresh culture medium, only within a few seconds or minutes (s 2 minutes) of when needed to replace volumes of medium that are removed from each of the perfusion bioreactor(s), either as volumes of permeate or cell bleed. A bioreactor has a characteristic mixing time, based on bioreactor and impeller design, and the agitation rate.

In various implementations, the fresh sterile liquid culture medium is added to the one or more perfusion bioreactors, by injecting the plurality of different concentrated component solutions at fixed ratios to one another, directly into the perfusion bioreactor(s), while an aqueous diluent (a suitable buffer or water) is also added at varied ratio(s) relative to the plurality of different concentrated medium component solutions, to maintain a constant culture volume in each perfusion bioreactor(s). Additionally, the fresh sterile liquid culture medium is added to the one or more perfusion bioreactors, by injecting the plurality of different concentrated component solutions and the aqueous diluent (a suitable buffer or water) at fixed ratios relative to one another, directly into the perfusion bioreactor(s), to maintain a constant culture volume in each perfusion bioreactor(s). In still other embodiments, the fresh sterile liquid culture medium is added to the one or more perfusion bioreactors, by injecting the plurality of different concentrated component solutions and the aqueous diluent (a suitable buffer or water), at fixed ratios relative to one another, into a mixing chamber wherein fresh sterile liquid culture medium is mixed contemporaneously (in a sterile mixing vessel fluidly connected to the bioreactor(s)) before being added to each perfusion bioreactor(s) to maintain a constant culture volume.

The particular ratios at which the medium components and the diluent are suitably mixed will vary depending on the culture medium recipe used and the concentrations of the concentrated medium components stocks used, and the appropriate ratios can be conveniently calculated by the skilled practitioner.

Sub-surface addition of the different concentrated medium component solutions and aqueous diluent is preferably avoided. Delivery of all medium component solutions and aqueous diluent on demand, through separate ports, can be accomplished manually or by using a ratio-controlled pumping skid and automation to maintain the culture volume in the perfusion bioreactor.

The term "buffer" or "buffered solution" refers to solutions which resist changes in pH by the action of its conjugate acid-base range. Examples of useful buffers include acetate, MES, citrate, Tris, bis-tris, histidine, arginine, succinate, citrate, glutamate, and lactate, or a combination of two or more of these, or other mineral acid or organic acid buffers; phosphate is another example of a useful buffer. Salts containing sodium, ammonium, and potassium cations are often used in making a buffered solution.

The term "antibody", or interchangeably "Ab", is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab, Fab', F(ab')$_2$, Fv, single chain antibodies, diabodies). Antibodies of any isotype class or subclass, including IgG, IgM, IgD, IgA, and IgE, IgG1, IgG2, IgG3, IgG4, IgA1 and IgA2, or any allotype, are contemplated. The term "monoclonal antibody" as used herein refers to an antibody obtained from a population of substantially homogeneous antibodies, i.e., the individual antibodies comprising the population are identical except for possible naturally occurring mutations that may be present in minor amounts.

The term "immunoglobulin" encompasses full or partial antibodies comprising two dimerized heavy chains (HC), each covalently linked to a light chain (LC); a single undimerized immunoglobulin heavy chain and covalently linked light chain (HC+LC), or a chimeric immunoglobulin (light chain+heavy chain)-Fc heterotrimer (a so-called "hemibody"), or a fusion protein comprising a dimerized or undimerized Fc domain, e.g. a peptibody. An "immunoglobulin" is a protein, but is not necessarily an antigen binding protein, e.g., a carrier antibody which is covalently linked to a clinically relevant target-binding moiety.

In an "antibody", each tetramer is composed of two identical pairs of polypeptide chains, each pair having one "light" chain of about 220 amino acids (about 25 kDa) and one "heavy" chain of about 440 amino acids (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. The variable region differs among different antibodies. The constant region is the same among different antibodies. Within the variable region of each heavy or light chain, there are three hypervariable subregions that help determine the antibody's specificity for antigen in the case of an antibody that is an antigen binding protein. The variable domain residues between the hypervariable regions are called the framework residues and generally are somewhat homologous among different antibodies. Immunoglobulins can be assigned to different classes depending on the amino acid sequence of the constant domain of their heavy chains. Human light chains are classified as kappa (.kappa.) and lambda (.lamda.) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)). An "antibody" also encompasses a recombinantly made antibody, and antibodies that are glycosylated or lacking glycosylation.

The term "light chain" or "immunoglobulin light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" or "immunoglobulin heavy chain" includes a full-length heavy chain and fragments thereof having sufficient variable region sequence to confer binding specificity. A full-length heavy chain includes a variable region domain, $V_H$, and three constant region domains, $C_{H1}$, $C_{H2}$, and $C_{H3}$. The $V_H$ domain is at the amino-terminus of the polypeptide, and the $C_H$ domains are at the carboxyl-terminus, with the $C_{H3}$ being closest to the carboxy-terminus of the polypeptide. Heavy chains are classified as mu (μ), delta (δ), gamma (γ), alpha (α), and epsilon (ε), and define the antibody's isotype as IgM, IgD, IgG, IgA, and IgE, respectively. Heavy chains may be of any isotype, including IgG (including IgG1, IgG2, IgG3 and IgG4 subtypes), IgA (including IgA1 and IgA2 subtypes), IgM and IgE. Several of these may be further divided into subclasses or isotypes, e.g. IgG1, IgG2, IgG3, IgG4, IgA1 and IgA2.

The term "antigen binding protein" (ABP) includes antibodies or antibody fragments, as defined herein, that specifically bind a target ligand or antigen of interest. An antigen binding protein, e.g., a therapeutic protein of interest, such as an immunoglobulin protein, or an antibody or antibody fragment, "specifically binds" to a target ligand or antigen of interest when it has a significantly higher binding affinity for, and consequently is capable of distinguishing, that target ligand or antigen, compared to its affinity for other unrelated proteins, under similar binding assay conditions. Typically, an antigen binding protein is said to "specifically bind" its target antigen when the dissociation constant ($K_D$) is $10^{-8}$ M or lower. The antigen binding protein specifically binds antigen with "high affinity" when the $K_D$ is $10^{-9}$ M or lower, and with "very high affinity" when the $K_D$ is $10^{-10}$ M or lower. "Antigen binding region" or "antigen binding site"

means a portion of a protein that specifically binds a specified target ligand or antigen.

A "chromatography system" is an arrangement of at least one enclosed chromatography matrix, with closed conduit hardware (e.g., pipes or tubing) for fluid ingress and egress from the at least one chromatography matrix. The chromatography system involves one or more pumps and/or valves to automatically or manually control the fluid flow rate and pressure. Chromatography systems of the inventive process and facility can incorporate chromatography matrices of various sorts, which the skilled practitioner knows how to select and use in sequence, as appropriate for the therapeutic protein of interest. Encompassed within the term "matrix" are resins, beads, nanoparticles, nanofibers, hydrogels, membranes (e.g., membrane adsorbers (MAs)), and monoliths, or any other physical matrix, bearing a relevant covalently bound chromatographic ligand (e.g., Protein A, Protein G, or other affinity chromatographic ligand, such as a target ligand, a charged moiety, or a hydrophobic moiety, etc.).

The term "elution buffer" or "eluant" refers to the buffer used to elute the protein of interest reversibly bound to a matrix. As used herein, the term "solution" refers to either a buffered or a non-buffered solution, including water. The term "elution pool" or "eluant pool" means the material eluted from a matrix, which material includes the recombinant protein of interest.

The terms "single-use" or "single use component(s)", used interchangeably, means that a particular aseptic production line component, i.e., a aseptic piece of equipment, used in the inventive automated facility or in performing the inventive process is constructed or configured to be employed for a single production run (but may be re-used if quality and aseptic sanitation can be assured for multiple runs). The single-use component can then be disposed of and replaced for subsequent production runs by a another single-use component of the same or modified configuration without the need for cleaning and sanitization of the component between production runs. Examples of single-use components that can be employed in the present invention include, but are not limited to, a perfusion bioreactor, the first chromatography system, the second chromatography system, the third chromatography system, the low pH or detergent viral inactivation system, the neutralization system, the viral filtration system, or the ultrafiltration/diafiltration system. Such single-use components can be constructed or obtained commercially.

The term "filter bank" or "filter assembly system", used interchangeably refers to an apparatus that includes multiple filter assemblies with each filter assembly including at least one filter. A filter included in a filter assembly can be a single-use filter and replaced after a period of time and/or after an amount of use. A filter bank can be a portable piece of equipment. For example, a filter bank can be disposed on a filtration cart that can be moved to various locations in an automated facility. The filters included in a filter bank can include a filtration system comprising a depth filter, a 0.2 micrometer filter, a membrane filter, a 20 nanometer (nm) filter, a viral filtration device, an ultrafiltration device, a diafiltration device, or combinations thereof. A filter bank can be configured such that while material is flowing through at least one filter of the filter bank, another filter of the filter bank remains unused. In various embodiments, a filter bank can be coupled to a diverter valve or other flow control device to control the flow of material to the filters included in the filter bank. The diverter valve or flow control device can be pneumatically controlled.

Manufacturing biotherapeutics described herein involves culturing recombinant therapeutic protein-secreting mammalian cells. Such recombinant mammalian host cells are made by transient or stable transfection. The biotherapeutics can be obtained by culturing the transfected or transformed host cells under physiological conditions allowing the cells to express recombinant proteins. Most conveniently, the expressed recombinant proteins are directly secreted into the extracellular culture medium (by employing appropriate secretory-directing signal peptides) and are harvested therefrom; otherwise additional steps will be needed to isolate the expressed antibodies from a cell extract.

The transfected or transformed host cells are typically cultured by any conventional type of culture, such as batch, fed-batch, intensified fed-batch, or continuous. The host cells used to produce biotherapeutics or POI (e.g., non-glycosylated or glycosylated proteins) described herein can be cultured in a variety of media.

The culture conditions, to be predetermined, such as temperature (for mammalian cells, typically, but not necessarily, about 37±1° C.), pH (typically, but not necessarily, the cell culture medium is maintained within the range of about pH 6.5-7.5), oxygenation, and the like, will be apparent to the ordinarily skilled artisan. By "culturing at" or "maintaining at" a predetermined culture condition, is meant that the process control systems are set at a particular value for that condition, in other words the intended volume, target temperature, pH, oxygenation level, or the like, maintained at predetermined set points for each parameter, within a narrow range (i.e., "narrow deadband") most optimal for the cell line and biotherapeutic of interest.

Typically, a viable cell density can be used from about $1.0 \times 10^6$ up to about $2 \times 10^8$ cells/mL, for example, in the range of $1.0 \times 10^6$ to $2.0 \times 10^7$ cells/mL, or in the range of about $4 \times 10^7$ cells/mL to about $5 \times 10^7$ cells/mL, or in the range of about $1 \times 10^8$ cells/mL to about $2 \times 10^8$ cells/mL. It is known that increasing the concentration of cells toward the higher end of the preferred ranges can improve volumetric productivity. Nevertheless, ranges of cell density including any of the above point values as lower or higher ends of a range are envisaged. The desired scale of the recombinant expression and cell culture will be dependent on the type of expression system and quantities of biotherapeutic desired.

Upon culturing the transfected or transformed host cells, the recombinant polypeptide or protein is directly secreted into the medium. Harvesting the recombinant protein involves separating it from particulate matter that can include host cells, cell aggregates, and/or lysed cell fragments, into a cell-free fraction that is free of host cells and cellular debris, i.e., a cell-free "permeate." Such cells and cellular debris is removed from the conditioned medium, for example, by centrifugation and/or microfiltration. For example, to make the permeate, one can employ hollow fiber membranes (pore size 0.2 μm) or a series of filtration steps such as depth filtration, which can be configured on a mobile, interchangeable and/or single use and "filtration cart."

The purification of recombinant proteins is usually accomplished by an optional series of chromatographic steps such as anion exchange chromatography, cation exchange chromatography, affinity chromatography (using Protein A or Protein G or Protein L as an affinity ligand or another different affinity ligand), hydrophobic interaction chromatography (HIC), hydroxy apatite chromatography, Reverse Phase HPLC, and size exclusion chromatography. In particular implementations for manufacturing biotherapeutics described herein, the recombinant therapeutic protein in the cell-free permeate is captured by one or more chromatographic capture steps of a first chromatography system that can partially purify and/or concentrate the protein, such as, but not limited to, Protein A or Protein G or Protein L affinity chromatography, or affinity chromatography employing a different affinity ligand covalently bound to a solid matrix.

The first, second, and/or optional third chromatography system(s) are configured as needed for the therapeutic protein of interest, preferably with one, two, three or more different chromatographic matrices (e.g., chromatography columns) fluidly linked in succession, and which, optionally, can be arranged in a mobile, interchangeable, or disposable, single-use unit, skid or "cart." In various implementations, the second chromatography system comprises a single-use membrane adsorber (MA), such as, a surface-functionalized membrane. Such membrane adsorbers can involve anion-exchange groups for mAb polishing operations in negative mode, in which trace impurities are removed without binding the protein of interest (so-called "flow-through chromatography").

In particular implementations, processes to produce the biotherapeutic herein can include switching the protein isolate fraction obtained or collected from the first chromatography system, into a low pH or detergent viral inactivation system, and a neutralization system (i.e., if neutralization is needed subsequent to viral inactivation by low pH), to obtain a virally inactivated pool comprising the recombinant therapeutic protein.

The resulting virally inactivated pool is subsequently introduced into the second chromatography system (in some embodiments, after being stored for at least 10 days or at least 20 days or at least 30 days) in a temperature controlled or chilled holding vessel (HV1) to obtain a purified product pool comprising the recombinant therapeutic protein. The second chromatography system is configured as needed for further purification of the therapeutic protein of interest, preferably with one, two, three or more different chromatographic matrices (e.g., chromatography columns) fluidly linked in succession, and which, optionally, can be arranged in a mobile, interchangeable, or disposable, single-use unit, skid or "cart."

Introducing the virally inactivated product pool into the second chromatography system is controlled according to a coordinated schedule with respect to the culturing and viral inactivation steps. The coordinated schedule is calculated to maximize the efficient routing of virally inactivated product pool into the second chromatography system. This loading of the virally inactivated product pool into the second chromatography system according to the coordinated schedule is by automatic (continuous format) or batch-wise manual control (semi-continuous format). (See, also, Garcia, F A and Vandiver, MW, Throughput Optimization of Continuous Biopharmaceutical Manufacturing Facilities, PDA J Pharm Sci Technol 71(3):189-205 (2017)).

From the second chromatography system the resulting purified product pool comprising the recombinant therapeutic protein is switched fluidly into an optional third chromatography system and/or a viral filtration system to obtain a virus-free filtrate comprising the recombinant therapeutic protein. Switching of the purified product pool into the optional chromatography system and/or viral filtration system is by automatic or manual control. The optional third chromatography system is configured, as needed for further purification of the therapeutic protein of interest, preferably with one, two, three or more different chromatographic matrices (e.g., chromatography columns) fluidly linked in succession, and which, optionally, can be arranged in a mobile, interchangeable, or disposable, single-use unit, skid or "cart." If a third chromatography system is not employed in the inventive process (or facility), then the purified product pool is switched and flows fluidly directly to the viral filtration system. Useful viral systems are commercially available, including single-use viral filtration systems.

The resulting virus-free filtrate containing the purified therapeutic protein of interest is subsequently switched fluidly into an ultrafiltration/diafiltration system to obtain the purified therapeutic protein drug substance comprising the purified recombinant therapeutic protein drug substance. Switching of the virus-free filtrate into the ultrafiltration/diafiltration system is by automatic or manual control.

In scenarios where multiple single-use perfusion bioreactors are utilized in a facility for the production of a purified therapeutic protein drug substance, multiple operations performed with respect to each bioreactor can be performed concurrently. For example, while an ultrafiltration/diafiltration operation is taking place with respect to the virus-free filtrate produced from a first perfusion bioreactor, a chromatography operation can be performed with respect to a virally inactivated product pool produced by the viral inactivation system (and, if needed, the neutralization system). The viral inactivation system can produce this virally inactivated pool by processing a protein isolate fraction that is received after processing by the first chromatography system of cell-free permeate derived from culturing in a second single-use perfusion bioreactor. In another example, while an ultrafiltration/diafiltration operation is taking place with respect to the virus-free filtrate ultimately produced by the inventive method from culturing in a first single-use perfusion bioreactor, a viral filtration operation can be performed with respect to a virally inactivated pool ultimately produced by the processes herein from culturing in a second perfusion bioreactor. In additional embodiments, at least one chromatography process and/or viral filtration process performed on virus-free filtrate produced from a first perfusion bioreactor can take place during continuous chromatography capture or viral inactivation processes performed on cell-free permeate volumes produced by a second single-use bioreactor in accordance with the inventive process.

Figure 5:
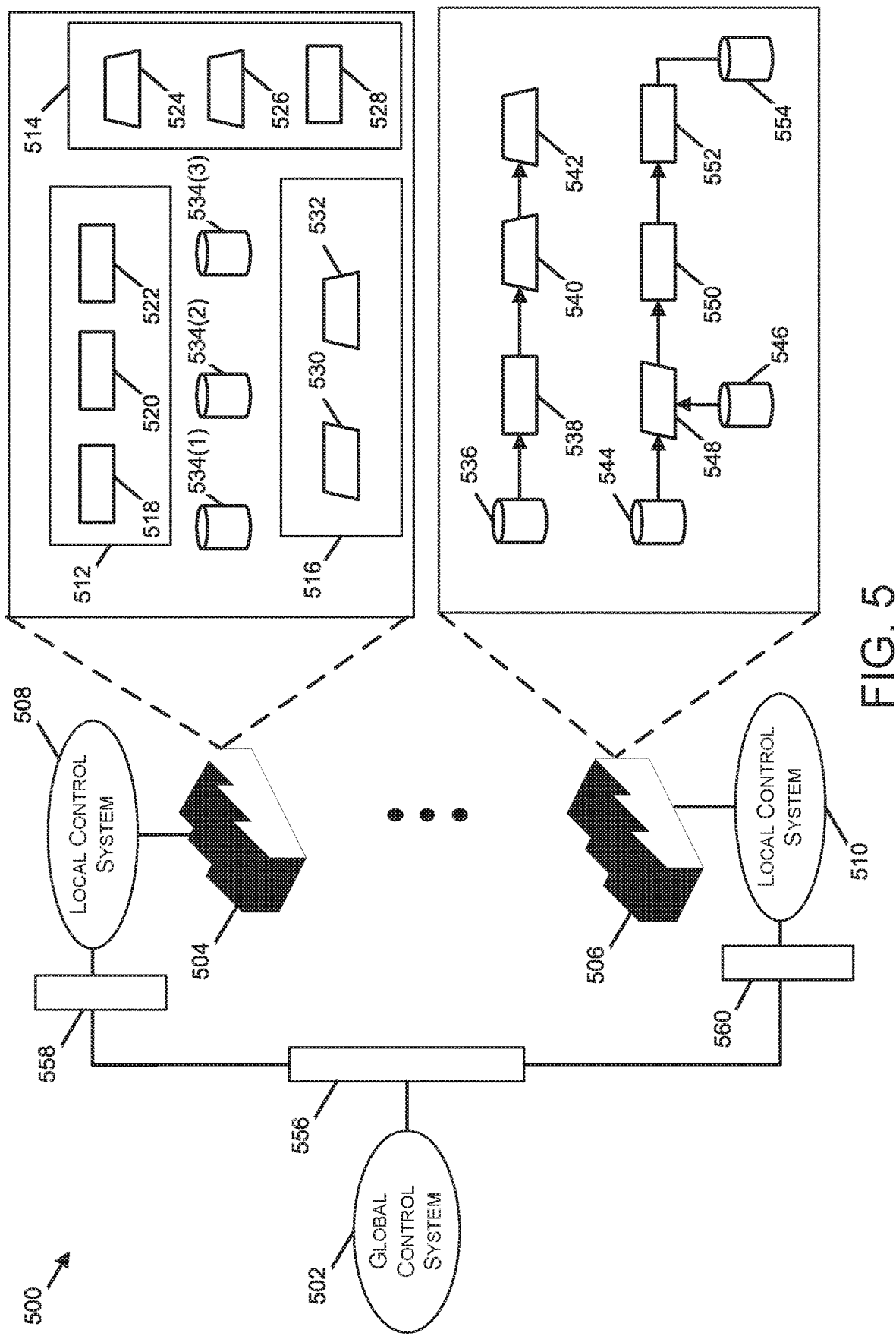
FIG. 5 is a diagram of an architecture to analyze data obtained from multiple production facilities and determine operational parameters for the control of pieces of equipment utilized in production lines of purified biotherapeutics according to some implementations.

FIG. 5 is a diagram of an architecture 500 to analyze data obtained from multiple production facilities and determine operational parameters for the control of pieces of equipment utilized in production lines of purified biotherapeutics. The architecture 500 can include a global control system 502 that collects and/or analyzes data from a number of production facilities including a first production facility 504 and a second production facility 506. The global control system 502 can analyze data obtained from the first production facility 504 and the second production facility 506 to determine control settings for pieces of equipment included in the first production facility 504 and the second production facility 506. The data collected by the global control system 502 can correspond to data from sensors that are associated with various pieces of equipment used in the production lines of the production facilities 502, 504. The sensor data can include or indicate temperature values, pH values, dissolved oxygen values, carbon dioxide values, capacitance values, pressure values, concentrations of one or more substances, quantity of one or more types of cells, flow rates, or combinations thereof.

The first production facility 504 can include or otherwise be in communication with a first local control system 508 and the second production facility 506 can include or otherwise be in communication with a second local control system 510. The first local control system 508 can also be referred to herein as a first production facility control system and the second local control system 510 can also be referred to herein as a second production facility control system. The first local control system 508 can analyze data obtained from pieces of equipment included in the first production facility 504. The first local control system 508 can also provide signals to control the operation of pieces of equipment included in the first production facility 504. The first production facility 504 can include a number of modular cleanrooms, such as a first modular cleanroom 512, a second modular cleanroom 514, and a third modular cleanroom 516. Although the illustrative example of FIG. 5 shows three modular cleanrooms in the first production facility 504, the first production facility 504 can include more modular cleanrooms or fewer modular cleanrooms. In various examples, the first production facility 504 can include at least one of the modular cleanroom 200 of FIG. 2, the modular cleanroom 300 of FIG. 3, or the modular cleanroom 400 of FIG. 4.

In the illustrative example of FIG. 5, the first modular cleanroom 512 can include a first piece of equipment 518, a second piece of equipment 520, and a third piece of equipment 522. In addition, the second modular cleanroom 514 can include a fourth piece of equipment 524, a fifth piece of equipment 526, and a sixth piece of equipment 528. Further, the third modular cleanroom 516 can include a seventh piece of equipment 530 and an eighth piece of equipment 532. Although the illustrative example of FIG. 5 shows that the modular cleanrooms 512, 514, 516 include a particular number of pieces of equipment, the modular cleanrooms 512, 514, 516 can include more or fewer pieces of equipment than the number shown in FIG. 3.

The pieces of equipment 518, 520, 522, 524, 526, 528, 530, 532 can include various pieces of equipment used to produce purified biotherapeutics. For example, at least one of the pieces of equipment 518, 520, 522, 524, 526, 528, 530, 532 can include a chromatography system. In another example, at least one of the pieces of equipment 518, 520, 522, 524, 526, 528, 530, 532 can include a bioreactor. In additional examples, at least one of the pieces of equipment can include a perfusion system. Further, at least one of the pieces of equipment 518, 520, 522, 524, 526, 528, 530, 532 can include a filter device. In various implementations, at least one of the pieces of equipment 518, 520, 522, 524, 526, 528, 530, 532 can include a pump device, a temperature control device, a storage container, or combinations thereof.

The first production facility 504 can also include a number of containers 534(1), 534(2), and 534(3). In particular implementations, the containers 534 can be located in a staging area of the first production facility 504. The containers 534 can store solutions or other materials that can be fed into one or more of the pieces of equipment 518, 520, 522, 524, 526, 528, 530, 532. In certain examples, one or more of the containers 534 can store buffer solutions. In additional examples, one or more of the containers 534 can include a material produced by a modular cleanroom 512, 514, 516. To illustrate, one or more of the containers 534 can store a virally inactivated pool produced by one of the modular cleanrooms 512, 514, 516 that can be fed into another one of the modular cleanrooms 512, 514, 516. Although the illustrative example of FIG. 5 shows three containers 534 located in the first production facility 504, the first production facility 504 can include fewer or more containers.

Additionally, the second local control system 510 can collect and analyze data obtained from pieces of equipment included in the second production facility 506. The second local control system 510 can also provide signals to control the operation of pieces of equipment included in the second production facility 504. The second production facility 506 can produce purified biotherapeutics without locating equipment in modular cleanrooms. The second production facility 506 can include a fourth container 536 coupled to a ninth piece of equipment 538 with the ninth piece of equipment 540 being coupled to a tenth piece of equipment 540 that is, in turn, coupled to an eleventh piece of equipment 542. The fourth container 536 and the pieces of equipment 538, 540, 542 can operate as at least a portion of a production line to produce the purified biotherapeutics. In the illustrative example of FIG. 5, the second production facility 506 can also include a fifth container 544 and a sixth container 546 coupled to a twelfth piece of equipment 548. The twelfth piece of equipment 548 can also be coupled to a thirteenth piece of equipment 550 that is coupled to a fourteenth piece of equipment 552. The fourteenth piece of equipment 552 can also be coupled to a seventh container 554.

The containers 536, 544, 546 can store various substances that are fed into the pieces of equipment 536 and 548. In illustrative examples, at least one of the containers 536, 544, 546 can store one or more buffer solutions. In additional illustrative examples, at least one of the containers 536, 544, 546 can store cell culture media. In particular illustrative examples, the container 544 can store effluent from the piece of equipment 542. Additionally, the container 554 can store effluent from the piece of equipment 552. Although the illustrative example of FIG. 5 shows a particular number of pieces of equipment and containers arranged in a particular configuration, the second production facility 506 can include more or fewer pieces of equipment and containers arranged in various configurations. The pieces of equipment and the configuration of the pieces of equipment can be based on a purified biotherapeutic being produced at the second production facility 506.

The pieces of equipment 538, 540, 542, 548, 550, 552 can include various pieces of equipment used to produce purified biotherapeutics. For example, at least one of the pieces of equipment 538, 540, 542, 548, 550, 552 can include a chromatography system. In another example, at least one of the pieces of equipment 538, 540, 542, 548, 550, 552 can include a bioreactor. In additional examples, at least one of the pieces of equipment 538, 540, 542, 548, 550, 552 can include a perfusion system. Further, at least one of the pieces of equipment 538, 540, 542, 548, 550, 552 can include a filter device. In various implementations, at least one of the pieces of equipment 538, 540, 542, 548, 550, 552 can include a pump device, a temperature control device, a storage container, or combinations thereof.

The architecture 500 can include a number of layers of network security to protect the global control system 502, the first local control system 508, and the second local control system 510 from intruders seeking to obtain and/or manipulate data collected and/or stored by the global control system 502, the first local control system 508, and the second local control system 510. The layers of network security can include one or more first firewalls 556, one or more second firewalls 558, and one or more third firewalls 560. The firewalls 556, 558, 560 can include hardware, software, firmware, or combinations thereof, that monitor and control communications coming into and going out of the overall control system 502, the first local control system 508, and the second local control system 510. The firewalls 556, 558, 560 can implement a number of security rules to allow or block communications directed to the overall control system 502, the first local control system 508, and the second local control system 510. In various examples, at least one of the one or more second firewalls 558 or the one or more second firewalls 560 can be combined with the one or more first firewalls 556.

Conventional production facility control systems are typically designed to control a preset configuration of equipment. In these scenarios, the logical and hardware couplings between pieces of equipment do not change. Thus, the identifiers and control operations that can be performed with respect to each piece of equipment are static. The implementations of production facility control systems, such as the first local control system 508 and the second local control system 510, described herein, support variable configurations of equipment in a production line. In these situations, a piece of equipment can have different functionality, perform different operations, and/or be controlled using different sets of control commands and/or variables based on the location of the piece of equipment within a production line. Thus, the production lines and control systems described herein include software configurations and physical hardware that are different from conventional systems.

The implementations described herein can be performed by one or more systems that can automatically control the flow of material through each step of the process to produce purified biotherapeutics. Alternatively, at least a portion of the control functions can be performed by operator intervention, and there may be circumstances (especially process disruptions) that may require operator intervention. The control functions can be performed using process data obtained from sensors coupled to various pieces of equipment used in the production of the purified biotherapeutics. The sensors can include temperature sensors, pH sensors, flow rate sensors, weight sensors (e.g., load cells), volume sensors (e.g., guided wave radar sensors), pressure sensors, timers, capacitance sensors, optical density sensors, or combinations thereof. The data generated by the sensors can be collected locally by the pieces of equipment. In certain implementations, the pieces of equipment can forward the sensor data to a production facility control system. The production facility control system can collect data from sensors of a number of pieces of equipment being used to manufacture the purified biotherapeutics. The production facility control system can include one or more computing devices and/or one or more data stores that are in electronic communication with each other. At least a portion of the one or more computing devices and/or one or more data stores can be located in a same location, in some scenarios. Additionally, at least a portion of the one or more computing devices and/or the one or more data stores can be located remotely from the equipment included in a production facility. In this situation, at least a portion of the operations performed by the production facility control system can be implemented in a cloud computing architecture.

The data collected from the sensors can be stored in electronic data stores that can be referred to herein as "data historians." In various implementations, a first data historian can collect and store data for at least a subset of the pieces of equipment operating in the first production facility 504 and a second data historian can collect and store data for at least a subset of the pieces of equipment operating in the second production facility 506. The first data historian and the second data historian can store data for a period of time and then forward the data to a third data historian that is a repository for data collected regarding the operation of pieces of equipment coupled to first local control system 508 and the second local control system 510. In particular implementations, the third data historian can be coupled to or otherwise be in communication with the global control system 502. In certain situations, the first data historian and the second data historian can then be reset and begin collecting and storing additional data from the first production facility 504 and the second production facility 506 for an additional period of time. The first local control system 508 and the second local control system 510 can also include one or more batch historians that collect and store data related to the operation of pieces of equipment included in the first production facility 504 and/or the second production facility 506 for the production of particular batches of the purified biotherapeutics. The data historians can be accessed by the global control system 502, the first local control system 508, and/or the second local control system 510 and analyzed to determine parameters for the operation of pieces of equipment included under the control of the control systems 502, 508, 510.

The control systems 502, 508, 510 can analyze the data obtained from the sensors associated with the pieces of equipment included in the first production facility 504 and the second production facility 506 and determine operating conditions for one or more of the pieces of equipment. In some cases, the set points and acceptable operating parameters, and/or run recipe for the operation of a piece of equipment can be entered into the control systems 502, 508, 510 by an operator. In other situations, the set points and acceptable operating parameters, and/or run recipe for the operation of a piece of equipment can be automatically sent to one or more pieces of equipment utilized in a production line via at least one of the control systems 502, 508, 510. Alerts and alarm notifications can also be generated by at least one of the control systems 502, 508, 510 based on the sensor data obtained from pieces of equipment located in the first production facility 504 and the second production facility 506. For example, in situations where sensor data indicates that an operating condition for a piece of equipment in a production line is outside of a threshold range, at least one of the control systems 502, 508, 510 can trigger an alarm and send notification to an operator.

Various pieces of equipment used to produce the purified biotherapeutics can include one or more communication interfaces that enable communications between the pieces of equipment and/or with one or more of the control systems 502, 508, 510. The communication interfaces can include hardware devices, firmware devices, and/or software implemented systems that enable communication of data between pieces of equipment used in a production line and/or with at least one control system 502, 508, 510. The communication interfaces can enable communication of data over a number of networks, such as local area wired networks, local area wireless networks, wide area wireless networks, and/or wide area wired networks. In particular examples, the communication interfaces can include Ethernet network communication interfaces, Internet Protocol network communication interfaces, Institute of Electrical and Electronics Engineers (IEEE) 802.11 wireless network communication interfaces, Bluetooth communication interfaces, or combinations thereof.

The pieces of equipment used to produce the purified biotherapeutics can include one or more processors and one or more memory devices. The one or more processors can be central processing units, such as standard programmable processors that perform arithmetic and logical operations necessary for the operation of computing systems. The one or more memory devices can include volatile and nonvolatile memory and/or removable and non-removable media implemented in any type of technology for storage of information, such as computer-readable instructions, data structures, program modules, or other data. Such computer-readable storage media can include, but is not limited to, RAM, ROM, EEPROM, flash memory or other memory technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, removable storage media, or any other medium that can be used to store the desired information and that can be accessed by the control systems 502, 508, 510 or by the individual pieces of equipment included in a production line.

The control systems 502, 508, 510 can store one or more control modules that can be executed to control the operation of the pieces of equipment included in the production facilities 504, 506. The control modules can include computer-readable instructions that can be executed to cause the pieces of equipment included in the production facilities 504, 506 to take one or more actions. The control modules can be part of a framework that enables the pieces of equipment included in the production facilities 504, 506 to produce purified biotherapeutics in a continuous or semi-continuous manner. The actions performed by various pieces of equipment included in the production facilities 504, 506 can be related to start up processes, hold processes, shutdown processes, feed processes, or end of production processes.

Various pieces of equipment can be controlled by different sets of control modules. For example, a perfusion system can be controlled by one or more first control modules, a bioreactor can be controlled by a one or more second control modules, and a chromatography system can be controlled by one or more third control modules. Additionally, in particular implementations, the same piece of equipment can be controlled by different control modules depending on the function of the piece of equipment within a production line. To illustrate, a storage container that operates as a feed tank can be controlled by one set of control modules, while the same storage container when operating as a collection tank can be controlled by another set of control modules.

In particular implementations, the control systems described herein can be used to control production lines that have flexible configurations. That is, the control systems 502, 508, 510 can accommodate multiple configurations that utilize portable equipment that can be coupled to other components of a production line. In various implementations, a production line can include one or more skids that include original manufacturer's equipment, such as a single-use bioreactor system, a perfusion system, or a continuous chromatography system. The skids can also include flow control devices, such as pumps. Additionally, the skids can include one or more communication interfaces, also referred to herein as "drops," that enable the physical coupling of portable pieces of equipment to the skid. The physical coupling between the portable pieces of equipment and the skid can be achieved using electrical cabling. The electrical cabling can be configured to enable ethernet communications. In certain examples, the electrical cabling can be Recommended Standard 232 (RS-232) cabling.

The portable pieces of equipment can include or otherwise be coupled to a network gateway hardware device that enables communication between the respective portable pieces of equipment and the production facility control system. The network gateway hardware device for each portable piece of equipment can be coupled to a communication interface of a respective skid. In addition, at least some of the skids can be logically configured to be coupled to various pieces of portable equipment. In this way, the pieces of portable equipment can be physically connected to a particular skid based on the configuration of a particular production line and the skids can be configured to operate in different configurations based on the different pieces of equipment coupled to the skid.

Additionally, the portable pieces of equipment can be coupled to at least one information communication and/or storage device, such as a dongle. The information communication and/or storage device can store information that is provided to the respective piece of equipment to which it is coupled that enables control of the respective piece of equipment via the production facility control system. The information communication and/or storage device can store information that includes one or more identifiers of a respective piece of equipment, one or more functions of the respective piece of equipment, one or more control signals corresponding to the respective piece of equipment, one or more status flags related to the respective piece of equipment, or combinations thereof. In some examples, the data stored by the information communication and/or storage device can be based at least partly on the functions, or a type, of the respective piece of equipment. In situations where a portable piece of equipment is placed in a different location along a production line and/or has a different function, the information communication and/or storage device of the portable piece of equipment can be switched to an additional information communication and/or storage device that indicates a different function and a different identifier for the portable piece of equipment.

Further, the control systems 502, 508, 510 can include an additional logical layer that can be used on top of conventional control software and systems. In particular implementations, the control systems 502, 508, 510 can include an additional abstraction layer that enables the assignment, also referred to as "binding," of the portable pieces of equipment to various identifiers, tags, operating conditions, and flags that correspond to a specified set of functions for a specific piece of equipment at a particular location along the production line. In this way, a piece of equipment is not logically represented in the control system until the location and function of the piece of equipment is known. Thus, portable pieces of equipment can be coupled with skids in a variety of combinations without having to change the underlying control software that is being utilized to control the components of the skids and also control the portable pieces of equipment.

In illustrative examples, a production line included in the first production facility 504 or the second production facility 506 can include a first skid that includes a single use bioreactor system, a second skid that includes a perfusion system, and a third skid that includes a continuous first chromatography system. In situations where skids are included in the first production facility 504, one or more skids can be included in each of the modular cleanrooms 512, 514, 516. The skids can be configured to couple to multiple portable pieces of portable equipment. For example, the skids can include interfaces and physical hardware to couple to portable storage containers, filter banks, divert valve systems (for switching automatically switchable alternate dual flow path or multi-flow path unit operations), and/or other flow control devices.

In additional illustrative examples, a control system 502, 508, 510 can determine that a filter bank is coupled between a perfusion bioreactor and a first chromatography system based on information obtained from a dongle coupled to the filter bank. In these situations, the filter bank can operate as a depth filter. The control system 502, 508, 510 can identify one or more control modules, flags, and/or status identifiers for a depth filter and execute the one or more control modules while the filter bank is being used in a production line. The control system 502, 508, 510 can monitor pressure within the filter assemblies of the filter bank based on pressure values obtained from pressure sensors included in the filter assemblies. Additionally, the control system 502, 508, 510 can determine that the pressure within a first filter assembly through which material is flowing has reached at least a threshold level. The threshold level of pressure can indicate that a filter included in the first assembly needs to be replaced due to a decrease in the amount of material that can be processed by the filter. The control system 502, 508, 510 can then send a signal to control a diverter valve coupled to the filter bank to cause the material to flow through a second filter assembly of the filter bank. The filter included in first filter assembly can then be replaced.

After coupling a piece of portable equipment to a skid, the piece of portable equipment can be registered with a control system 502, 508, 510. The piece of portable equipment can have a unique address that the piece of portable equipment can communicate to a control system 502, 508, 510. The unique address can indicate a type of the piece of portable equipment and a unit identifier to a control system 502, 508, 510. A dongle coupled to the piece of portable equipment can store an additional identifier that corresponds to a location of the skid to which the portable piece of equipment is coupled and one or more functional roles of the portable piece of equipment. For example, a mix tank can be identified as a feed tank, or a collection tank based on the location of the portable piece of equipment and the logical association of the drop to which the portable piece of equipment is coupled. In another example, a filter bank can be identified as a viral filtration device in a first configuration of a production line and then identified as a diafiltration device in a second configuration of a production line. In these situations, a first dongle can be coupled to the filter bank in the first configuration of the production line and a second dongle can be coupled to the filter bank in the second configuration of the production line. Additionally, the type of filter used in the filter bank can be changed when the filter bank is used in different locations of a production line.

In response to obtaining the information from the portable piece of equipment after being coupled to the skid, a control system 502, 508, 510 can determine the location and functions of the portable piece of equipment and assign the corresponding control templates to the portable piece of equipment. For example, in situations where a storage container is functioning as a collection tank, a control system 502, 508, 510 can assign a first set of tags, flags, identifiers, and set points to the storage container and in situations where a storage container is functioning as a feed tank, a control system 502, 508, 510 can assign a second set of tags, flags, identifiers, and set points to the storage container. A control system 502, 508, 510 can then assign a particular set of control modules to the portable piece of equipment based on the information obtained from the portable piece of equipment after being coupled to the skid.

In various embodiments, pieces of equipment that are not considered portable, such as large storage containers (e.g., having a volume greater than 1000 L) can also be coupled to the skid. In these scenarios, the non-portable pieces of equipment may not include the hardware and/or communication and storage devices that enable dynamic configuration of the non-portable piece of equipment with respect to a control system 502, 508, 510. If the non-portable piece of equipment is not configured for a dynamic configuration, an operator of a control system 502, 508, 510 can manually establish the template and/or control module used to control the operation of the non-portable piece of equipment.

In addition to the control of the pieces of equipment included in a production line, a control system 502, 508, 510 can also track the decay rate of a batch during production of a purified therapeutic protein drug substance. Decay rate can be defined as "a period of time in which materials used for the production of sub-lots can be identified and tracked." For example, the materials used (buffers, cell culture medium, etc.) in a resulting chromatography eluate pool collection (1 of many) can be identified and tracked in a dynamic fashion. In a continuous batch production process, a control system 502, 508, 510 can estimate the decay rate for a production process for purified therapeutic protein drug substances. In various implementations, a control system 502, 508, 510 can assign batch identifiers to certain portions of the production of the batch and initiate a decay monitor until the current batch identifier is changed to a new batch identifier and a new decay monitor is implemented for the new batch identifier.

In various implementations, the global control system 502 can analyze data obtained from the first local control system 508 and the second local control system 510 to generate one or more models to control the operation of pieces of equipment included in the first production facility 504 and/or the second production facility 506. The global control system 502 can also analyze data obtained from the first local control system 508 and the second local control system 510 to generate one or more additional models to predict the efficiency and/or productivity of one or more pieces of equipment and/or the efficiency and/or productivity of one or more production lines included in the first production facility 504 and the second production facility 506. The use of data obtained from multiple production facilities to predict the operation of production lines and to predict the efficiency and/or productivity of pieces of equipment and/or production lines can lead to generating more accurate models and generating the models more efficiently. The global control system 502 can also analyze data obtained from the first control system 508 and/or the second control system 510 to generate models to predict values of process variables of one or more pieces of equipment included in the first production facility 504 and the second production facility 506.

In particular, conventional production facilities are often customized and the data gathered for each conventional production facility may only be useful for determining control of that particular production facility. In contrast, the global control system 502 can leverage similarities between production facilities to gather sufficient quantities of relevant data more quickly than conventional systems. In this way, the global control system 502 can generate models used in the control of production lines and models to predict the efficiency and/or productivity of production lines more quickly, and more accurately than with respect to conventional systems due to the increased amount of data available to the global control system 502 that can be used to generate the models. Additionally, by generating one model or a single set of models that can be used to control production lines and predict the efficiency and/or productivity of multiple production facilities, the global control system 502 can minimize the computing resources utilized in the control of a number of production facilities because different models don't need to be implemented for different production facilities. Additionally, a single control system can implement a model for multiple production facilities.

In particular implementations, the global control system 502 can obtain data from the first local control system 508 that indicates various process conditions for one or more production lines included in the first production facility 504. The process conditions can correspond to data obtained by sensors associated with pieces of equipment in the one or more production lines. In some illustrative examples, the process conditions can correspond to pH values, temperature values, capacitance values, flow rates, volumes, mass/weight values, concentration of one or more substances, cell counts, or combinations thereof. The global control system 502 can analyze the data obtained from the first local control system 508 to determine a number of factors that are indicators of efficiency and/or productivity of the one or more production lines. In various implementations, the global control system 502 can determine a significance for individual factors based on the data obtained from the first production facility and identify factors having a significance above a threshold level. The global control system 502 can then generate a model with variables that correspond to the factors having at least a threshold significance. In this way, the global control system 502 can generate a model that can be implemented to predict an efficiency and/or productivity based on factors that have at least a threshold amount of impact on the efficiency and/or productivity of the one or more production lines.

The global control system 502 can utilize one or more machine learning techniques to determine that factors having at least a threshold amount of impact on the efficiency and/or productivity of the one or more production lines of the first production facility 502. For example, the global control system 502 can utilize inferential modeling techniques to determine the factors having at least a threshold amount of impact on the efficiency and/or productivity of the one or more production lines of the first production facility 502. In illustrative examples, the global control system 502 can implement partial least squares techniques to determine factors that have at least a threshold amount of impact on the productivity and/or efficiency of one or more production lines included in the first production facility 504. In additional illustrative examples, the global control system 502 can implement polynomial lag techniques to determine factors that have at least a threshold amount of impact on the productivity and/or efficiency of one or more production lines included in the first production facility 504. The global control system 502 can also determine coefficients corresponding to each of the factors included in the model. The coefficients can indicate an amount of impact of the respective factors on the productivity and/or efficiency of the one or more production lines.

In various implementations, the global control system 502 can analyze data obtained from the first production facility 504 over a first period of time using a partial least squares technique to determine the one or more factors having at least a threshold impact on the production and/or efficiency to include in a model and then utilize data obtained over a second period of time, subsequent to the first period of time, to validate the model. In particular examples, the global control system 502 can analyze data obtained from the first production facility 504 for a period of at least two days before a set date and/or time using a partial least squares technique and generate a model based on the data obtained during that period of time. The global control system 502 can then utilize data obtained for a period of time of at least one day after the set date and/or time to validate the model.

The global control system 502 can modify the factors included in the model and/or the coefficients associated with the factors as data obtained from the first production facility 504 changes over time. For example, the global control system 502 can make changes to the factors included in a model based on changes to data obtained from the first production facility 504. To illustrate, the global control system 502 can determine that a different set of factors have a threshold amount of impact on the productivity and/or efficiency of a production line than an initial set of factors identified by the global control system 502. In these situations, the global control system 502 can modify the factors included in a model used to predict the efficiency and/or productivity of the production line. In additional examples, the global control system 502 can determine that coefficients of a model are to be modified based on changes to data obtained by the global control system 502 from one or more production lines of the first production facility 504. In some implementations, the global control system 502 can utilize a rolling window of time to continually update a model. That is, the global control system 502 can periodically analyze data obtained from the first production facility 504 over a predetermined amount of time and modify one or more of the factors and/or coefficients included in the model based on changes to the data obtained from the first production facility 504.

In various implementations, the global control system 502 can determine that factors such as a previous day's viable cell density, cell viability, dissolved oxygen readings, carbon dioxide levels, temperature, and/or pH have at least a threshold impact on one or more production lines included in the first production facility 504. In particular examples, the data analyzed by the global control system 502 to determine the factors to include in a model can be obtained from a bioreactor included in the first production facility 504. In additional examples, the data analyzed by the global control system 502 to determine the factors included in a model can be obtained from one or more chromatography systems. In still other examples, the data analyzed by the global control system 502 to determine factors included in a model can be obtained from one or more filter banks, one or more storage containers, one or more temperature control devices, one or more pumping devices, or combinations thereof.

In some implementations, the global control system 502 can determine a model for individual pieces of equipment included in a production line of the first production facility 504. Further, the global control system 502 can determine a model for a single production line that includes a plurality of pieces of equipment. Additionally, as the configuration of a production line changes, the global control system 502 can generate a different model for the different configurations of a production line. The factors included in the models generated by the global control system 502 can also be based at least partly on bioreactor volume, purified biotherapeutic produced by a production line, cell line utilized to produce a biotherapeutic, a measure of productivity and/or efficiency predicted, and/or whether the process is a perfusion process or a batch process. Examples of measures of productivity and/or efficiency for a production line can include yield, titer, purity, and viable cell density. A model can be generated by the global control system 502 for a single measure of productivity and/or efficiency, in some situations, while in other scenarios, the global control system 502 can generate a model for multiple measures of productivity and/or efficiency of a production line.

In particular illustrative examples, the global control system 502 can obtain data from a 2-liter fed-batch bioreactor and generate a model to predict future viable cell density for the 2-liter fed-batch bioreactor that includes factors corresponding to at least one of a previous day's viable cell density, cell viability, dissolved oxygen levels, carbon dioxide levels, temperature, pH, or time since last viable cell density measurement. In other illustrative examples, the global control system 502 can obtain data from a perfusion bioreactor and generate a model for the perfusion bioreactor to predict future viable cell density that includes factors corresponding to at least one of perfusion rate, previous day's viable cell density, and cell viability.

The global control system 502 can also analyze data obtained from the first local control system 508 to determine factors that have an effect on the factors that have an impact on the efficiency and/or productivity of a production line producing purified biotherapeutics. In implementations described herein, factors that can be indicators of efficiency and/or productivity of a process can be referred to as "process variables", while factors that can impact the process variables can be referred to as "control variables". In particular implementations, control variables can be related to a control setting of a piece of equipment included in a production line. For example, temperature can be impacted by modifying a temperature setting on a piece of equipment, such as a bioreactor or a heat exchanger. In additional examples, pH can be impacted by adding an acidic buffer solution or a basic buffer solution to a piece of equipment, such as a bioreactor, a chromatography system, or a storage container. In various implementations, at least a portion of the control variables for a given process variable can be the same as the control variables for another process variable, while in additional scenarios, at least a portion of the control variables for a specified process variable can be different from the control variables for an additional process variable. To illustrate, at least one of the control variables having an impact on dissolved oxygen levels can be different from at least one of the control variables having an impact on cell viability.

The control variables that can be modified to impact one or more process variables may not be directly related. In a particular example, a process having a cell density that is less than a minimum threshold may not have a higher cell density in response to increasing a number of cells added to the process. Additionally, a process having a cell density above a maximum threshold may not have with a lower cell density in response to decreasing a number of cells removed from the process, such as by increasing the bleed rate. In these situations, machine learning techniques can be implemented with respect to data obtained by the global control system 502 from the first local control system 508 to determine control variables that can have at least a threshold amount of impact on one or more process variables. In some implementations, inferential machine learning techniques, such as partial least squares techniques, can be used to determine one or more control variables that correspond to individual process variables.

Models generated by the global control system 502 using data obtained from the first local control system 508 can also be utilized with respect to other production lines included in additional production facilities. For example, models generated by the global control system 502 using data obtained from the first local control system 508 can be utilized with respect to one or more production lines included in the second production facility 506. Additionally, the global control system 502 can generate one or more models to predict efficiency and/or productivity of one or more production lines of the first production facility 504 and the second production facility 506 using data obtained from both the first local control system 508 and the second local control system 510.

The global control system 502 can also generate models that predict values of various process variables that can be used when determining control parameters and/or settings for pieces of equipment included in a production line. In particular implementations, the data obtained from the first local control system 508 and/or the second local control system 510 can be analyzed to determine factors that are significant in predicting values of process variables and include factors having at least a threshold amount of significance in models to predict process value variables. The global control system 502 can then compare the predicted values for process variables to various thresholds for those process variables. The thresholds for process variables can indicate when action should be taken with respect to a particular piece of equipment or process. In this way, in situations where one or more process variables are outside of specified threshold values, the global control system 502 can determine one or more actions that can be performed based on the values of the process variables with respect to the threshold values. In various implementations, the global control system 502 can determine one or more actions that can be performed to move the values for the process variables back to being within the threshold values.

In various implementations, the global control system 502 can generate models to determine the productivity, efficiency, and/or control of production lines in facilities having a similar configuration of a production line. A configuration of a production line can be similar to another configuration when the pieces of equipment included in the production line are of a same or similar type and/or arranged in a same or similar order. Also, the global control system 502 can generate models to determine productivity, efficiency, and/or control for individual pieces of equipment included in multiple production facilities. That is, the global control system 502 can determine a model to predict the productivity, efficiency, and/or control of a bioreactor that is included in multiple production facilities. In various implementations, the model can predict the productivity, efficiency, and/or control of a bioreactors having a same or similar size and/or manufactured by a same manufacturing company that are included in multiple production facilities, such as the first production facility 504 and the second production facility 506. In additional examples, the global control system 502 can predict the productivity, efficiency, and/or control of continuous chromatography systems having a same or similar size and/or manufactured by a same manufacturing company that are included in multiple production facilities. In certain situations, the global control system 502 can generate models that account for the number of chromatography columns included in the chromatography systems, the length of columns of the chromatography systems, a size and/or molecular weight of molecules being processed by the chromatography systems, or combinations thereof.

In particular implementations, the global control system 502 can generate models for different phases of growth in a bioreactor. For example, the global control system 502 can generate a first model to predict the productivity, efficiency, and/or control of a growth phase of bioreactors included in one or more production facilities. In additional examples, the global control system 504 can generate a second model to predict the productivity, efficiency, and/or control of a steady-state phase of bioreactors included in one or more production facilities.

Further, the global control system 502 can determine periods of time when one or more models can be applied with respect to the productivity, efficiency, and/or control of one or more pieces of equipment included in production lines of the first production facility 504 and/or the second production facility 506. The global control system 502 can also determine periods of time when one or more models are not applicable with respect to the productivity, efficiency, and/or control of one or more pieces of equipment included in production lines of the first production facility 502 and/or the second production facility 506. To illustrate, the global control system 502 can determine parameters corresponding to conditions where the accuracy of the predictions made by models generated by the global control system 502 is above a threshold level of accuracy. In some illustrative examples, the global control system 502 can determine values of temperatures, pH values, flow rates, cell culture media, end products, equipment used in production lines, viable cell density values, carbon dioxide levels, dissolved oxygen levels, or combinations thereof, that are applicable to a given model. In situations where the conditions for a process are outside of those that are applicable to one or more models, the global control system 502 can determine one or more default modes of operation and/or send a notification to an operator indicating that the process conditions are outside of those for which one or more models generated by the global control system 502 are applicable.

The global control system 502 can also determine data points that may be missing from the data obtained from the first local control system 508 and the second local control system 510. For example, the global control system 502 can obtain data periodically from the first local control system 508 and the second local control system 510. In some situations, at least a portion of the data expected to be received by the global control system 502 may not be received. In these scenarios, the global control system 502 can generate models and/or perform calculations related to the control of the first production facility 504 and/or the second production facility 506 without the missing data. In other implementations, the global control system 502 can estimate the missing data. To illustrate, the global control system 502 can utilize previous data to estimate the missing data. In an illustrative example, the global control system 502 can fill in the missing data using an average of previous values over a period of time. In other illustrative examples, the global control system 502 can fill in the missing data by replicating one or more previous values. In a particular illustrative example, the global control system 502 can determine that one or more pH values are missing from a bioreactor included in the first production facility 504. The global control system 502 can utilize previous values of the pH of the bioreactor to fill in the missing data and the global control system 502 can implement one or more models related to the productivity, efficiency, and/or control of the bioreactor using a data set that includes the missing data. In particular implementations, the global control system 502 can determine that missing data needs to be filled in when a threshold amount of data is missing, such as a threshold number of data points being missing over a specified period of time.

Although the illustrative example of FIG. 5 includes a first production facility 504 and a second production facility 506, the global control system 502 can generate models to predict the productivity, efficiency, and/or control of more production facilities. Additionally, the global control system 502 can generate models that are applicable to multiple production facilities that include production lines located in modular cleanrooms. The global control system 502 can also produce models that are applicable to multiple production facilities that include production lines that are not located in modular cleanrooms. In still additional situations, the global control system 502 can produce models that are applicable to both production facilities having production lines that are located in modular cleanrooms and production facilities having production lines that are not located in modular cleanrooms. Further, the global control system 502 can generate models that can be used in relation to the first production facility 504 and the second production facility 506 and pass the models to the first local control system 508 and the second local control system 510. In these scenarios, the first local control system 508 and the second local control system 510 can analyze data obtained from pieces of equipment located in the first production facility 504 and the second production facility 506 and apply the data to the models provided by the global control system 502. In this way, the calculations performed to implement models with respect to the first production facility 504 and the second production facility 506 can be performed by the first local control system 508, the second local control system 510, and/or the global control system 502.

Figure 6:
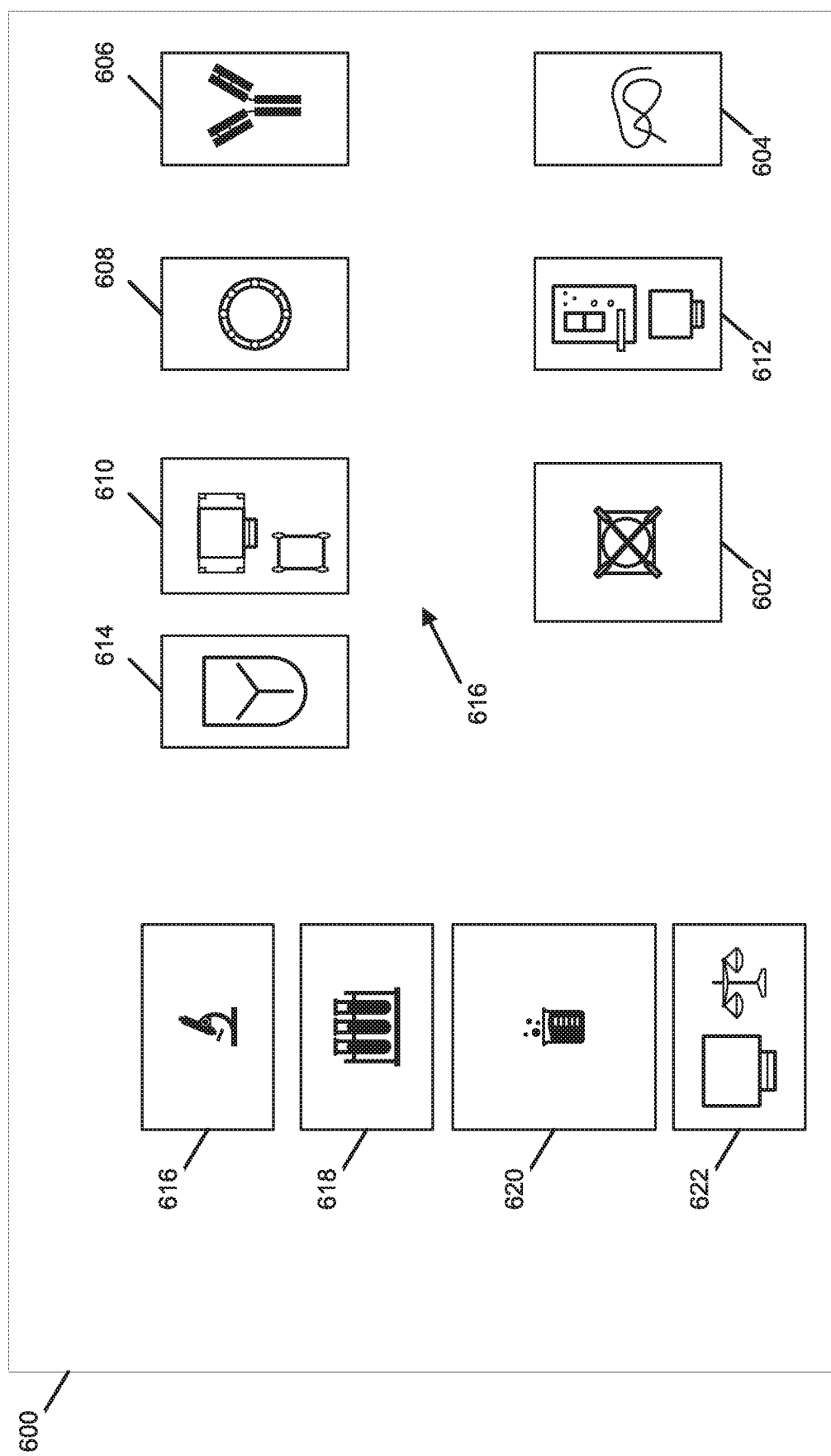
FIG. 6 is a diagram of a layout of a production facility that includes a number of modular cleanrooms that include pieces of equipment that are used to produce one or more biotherapeutics.

FIG. 6 is a diagram of a layout of a production facility 600 that includes a number of modular cleanrooms that include pieces of equipment that are used to produce one or more biotherapeutics. For example, the production facility 600 can include a first modular cleanroom 602. The first modular cleanroom 602 can include at least one bioreactor that can produce a biotherapeutic, such as a recombinant therapeutic protein, using cell culture media, cell growth material, and one or more buffer solutions. In one or more examples, the first modular cleanroom 602 can include additional pieces of equipment. In various implementations, the first modular cleanroom 602 can include a perfusion system. In additional implementations, the first modular cleanroom 602 can include a continuous chromatography system to process effluent produced by the bioreactor. In one or more illustrative examples, the first modular cleanroom 602 can include equipment to virally inactivate effluent produced by the bioreactor. To illustrate, the first modular cleanroom 602 can include one or more pumping devices and one or more storage containers that store effluent produced by the bioreactor such that the one or more pumping devices can supply an acid or a detergent to material stored in the one or more storage containers to produce a virally inactivated pool.

In the illustrative example of FIG. 6, the production facility 600 can also include a second modular cleanroom 604 and a third modular cleanroom 606. The second modular cleanroom 604 can include a first additional bioreactor and the third modular cleanroom 606 can include a second additional bioreactor. The first additional bioreactor included in the second modular cleanroom 604 and/or the second additional bioreactor included in the third modular cleanroom 606 can be used to produce a same biotherapeutic as the bioreactor located in the first modular cleanroom 602. In various implementations, the first additional bioreactor included in the second modular cleanroom 604 and/or the second additional bioreactor included in the third modular cleanroom 606 can operate concurrently to produce a biotherapeutic. In additional implementations, the first additional bioreactor included in the second modular cleanroom 604 and/or the second additional bioreactor included in the third modular cleanroom 606 can operate in a serial manner such that after the bioreactor included in the first modular cleanroom 602 has produced an amount of a biotherapeutic, at least one of the first additional bioreactor included in the second modular cleanroom 604 or the second additional bioreactor included in the third modular cleanroom 606 can produce an additional amount of the biotherapeutic.

In further implementations, at least one of the first additional bioreactor included in the second modular cleanroom 604 or the second additional bioreactor included in the third modular cleanroom 606 can be used to produce a biotherapeutic that is different from the biotherapeutic produced by the bioreactor included in the first modular cleanroom 602. In one or more implementations, the second modular cleanroom 604 and/or the third modular cleanroom 606 can include pieces of equipment in addition to a bioreactor, such as one or more chromatography systems, one or more storage containers, one or more pumping devices, one or more perfusion systems, one or more filter devices, or one or more combinations thereof. In one or more illustrative examples, at least one of the first modular cleanroom 602, the second modular cleanroom 604, or the third modular cleanroom 606 can include an arrangement of pieces of equipment that corresponds to the arrangement of equipment described with respect to FIG. 2.

The production facility 600 can also include a fourth modular cleanroom 608. The fourth modular cleanroom 608 can include equipment that can be used to purify material produced by one or more pieces of equipment located in at least one of the first modular cleanroom 602, the second modular cleanroom 604, or the third modular cleanroom 606. For example, the fourth modular cleanroom 608 can include one or more chromatography systems. In various examples, the one or more chromatography systems located in the fourth modular cleanroom 608 can purify virally inactivated material transferred from at least one of the first modular cleanroom 602, the second modular cleanroom 604, or the third modular cleanroom 606. In one or more implementations, the fourth modular cleanroom 608 can include equipment to produce virally inactivated material that is then purified using one or more chromatography systems located in the fourth modular cleanroom 608. Additionally, the fourth modular cleanroom 608 can include one or more viral filtration devices. The one or more viral filtration devices can produce a virus-free filtrate. In one or more illustrative examples, the arrangement of pieces of equipment included in the fourth modular cleanroom 608 can correspond to the arrangement of equipment described with respect to FIG. 3.

Further, the production facility 600 can include a fifth modular cleanroom 610. The fifth modular cleanroom 610 can include one or more additional filtering devices that can perform one or more filtering operations in relation to the virus-free filtrate produced by equipment located in the fourth modular cleanroom 608. To illustrate, the fifth modular cleanroom 610 can include one or more filtering devices to perform one or more ultrafiltration operations. In one or more implementations, the fifth modular cleanroom 610 can include one or more filtering devices to perform one or more diafiltration operations. The production facility 600 can also include a sixth modular cleanroom 612 that can include one or more pieces of equipment to perform at least one of one or more ultrafiltration operations or one or more diafiltration operations with respect to virus-free filtrate produced by the equipment located in the fourth modular cleanroom 608. The equipment located in the fifth modular cleanroom 610 and the equipment located in the sixth modular cleanroom 612 can operation concurrently to process virus-free filtrate produced by equipment located in the fourth modular cleanroom 608. In additional implementations, the equipment located in the fifth modular cleanroom 610 and the equipment located in the sixth modular cleanroom 612 can operate at different times or in a serial manner to process virus-free filtrate produced by equipment located in the fourth modular cleanroom 608. In one or more illustrative examples, the arrangement of equipment located in at least one of the fifth modular cleanroom 610 or the sixth modular cleanroom 612 can correspond to the arrangement of equipment described with respect to FIG. 4.

Additionally, the production facility 600 can include a seventh modular cleanroom 614. The seventh modular cleanroom 614 can include one or more pieces of equipment to perform one or more cell expansion operations. In various examples, the cells produced by pieces of equipment included in the seventh modular cleanroom 614 can be used by one or more bioreactors included in the first modular cleanroom 602, the second modular cleanroom 604, and/or the third modular cleanroom 606.

Individual modular cleanrooms 602, 604, 606, 608, 610, 612, 614, can have the same or similar dimensions. In additional implementations, one or more of the modular cleanrooms 602, 604, 606, 608, 610, 612, 614 can have different dimensions from at least one other modular cleanroom 602, 604, 606, 608, 610, 612, 614. In one or more illustrative examples, the modular cleanrooms 602, 604, 606, 608, 610, 612, 614 can have an area from about 15,000 $ft^2$ to about 50,000 $ft^2$. Additionally, the modular cleanrooms 602, 604, 606, 608, 610, 612, 614 can be operated in accordance with one or more cleanroom standards. For example, an environment of at least one of the fifth modular cleanroom 610, the sixth modular cleanroom 612, or the seventh modular cleanroom 614 can be maintained according to ISO 7 cleanroom standards. In addition, an environment of the fourth modular cleanroom 608 can be maintained according to ISO 8 cleanroom standards. In some situations, an environment of the fourth modular cleanroom 608 can be maintained according to ISO 8 cleanroom standards. In one or more implementations, an environment in at least one of the first modular cleanroom 602, the second modular cleanroom 604, or the third modular cleanroom 606 can be maintained according to ISO 8 or ISO 7 cleanroom standards.

Further, although the production facility 600 shown in the illustrative example of FIG. 6 includes seven modular cleanrooms arranged according to a particular layout, in one or more additional implementations, the production facility 600 can include a different number of modular cleanrooms arranged according to one or more different layouts. In addition, the modular cleanrooms 602, 604, 606, 608, 610, 612, 614 can be positioned differently than shown in the illustrative example of FIG. 6.

The production facility 600 can also include a staging area 616. The staging area 616 can include storage containers that can store material that is to be transferred into equipment located in one or more of the modular cleanrooms 602, 604, 606, 608, 610, 612, 614. In addition, the staging area 616 can include one or more storage containers that can store material that is transferred out of one or more of the modular cleanrooms 602, 604, 606, 608, 610, 612, 614. In various examples, one or more storage containers located in the staging area 616 can be coupled to at least one port of at least one of the modular cleanrooms 602, 604, 606, 608, 610, 612, or 614 to transfer material into or out of one or more respective modular cleanroom 602, 604, 606, 608, 610, 612, 614.

The production facility 600 can also include a number of additional areas that can support the operations performed by equipment located in one or more of the modular cleanrooms 602, 604, 606, 608, 610, 612, 614. For example, the production facility 600 can include a first area 616 that can correspond to quality control and/or shipping or labeling control. In various examples, quality control samples can be obtained with respect to one or more pieces of equipment included in at least one of the modular cleanrooms 602, 604, 606, 608, 610, 612, 614. The quality control samples can then be tested in a quality control area 616.

In addition, the production facility 600 can include a second area 618 that can correspond to a preparation area. To illustrate, at least one of buffer solutions and/or cell culture media can be prepared in the second area 618. The production facility 600 can also include a third area 620 that can correspond to a washing and cleaning area. Equipment utilized in the production and/or storage of one or more biotherapeutics can be cleaned and/or sterilized in the third area 620. In one or more implementations, the production facility 600 can include a fourth area 622 that can correspond to a weighing and/or storage area. For example, the fourth area 622 can be used to weigh material that is transferred into one or more of the modular cleanrooms 602, 604, 606, 608, 610, 612, 614. The fourth area 622 can also be used to weigh material that is transferred out of one or more of the modular cleanrooms 602, 604, 606, 608, 610, 612, 614. Additionally, the fourth area 622 can include one or more storage containers that store material that is used by one or more pieces of equipment included in at least one of the modular cleanrooms 602, 604, 606, 608, 610, 612, 614. Further, the fourth area 622 can include one or more storage containers that store material that is produced by equipment included in at least one of the modular cleanrooms 602, 604, 606, 608, 610, 612, 614.

Although the illustrative example of FIG. 6 shows that the production facility 600 includes four additional areas 616, 618, 620, 622, in additional implementations, the production facility 600 can include further areas in which one or more operations take place. For example, the production facility 600 can include at least one of office space, one or more shipping areas, one or more receiving areas, one or more waste disposal areas, one or more warehouse areas, and so forth. Also, although various operations have been described in relation to a respective area 616, 618, 620, 622, these operations can take place within or outside of the respective areas 616, 618, 620, 622. Furthermore, operations described in relation to one of the respective areas 616, 618, 620, 622 can be consolidated into another one of the respective areas 616, 618, 620, 622, in various implementations. In addition, although the additional areas 616, 618, 620, 622 are shown as having a respective size within the production facility 600, the relative area associated with the respective areas 616, 618, 620, 622 can differ from that shown in the illustrative example of FIG. 6.

In one or more illustrative examples, as at least one of the bioreactor included in the first modular cleanroom 602, the first additional bioreactor included in the second modular cleanroom 604, or the second additional bioreactor included in the third modular cleanroom 606 have completed a production run for a first biotherapeutic, at least one of the bioreactor included in the first modular cleanroom 602, the first additional bioreactor included in the second modular cleanroom 604, or the second additional bioreactor included in the third modular cleanroom 606 can be used in a production run to produce a second, different biotherapeutic. In these scenarios, equipment can be moved into and/or out of one or more of the modular cleanrooms 602, 604, 606, 608, 610, 612, 614. For example, at least one of a pumping device, a filter device, a chromatography system, or a storage container can change locations within the production facility such that the equipment included in one or more of the modular cleanrooms 602, 604, 606, 608, 610, 612, 614 is suitably arranged to produce the second biotherapeutic. In various examples, a different bioreactor can be used to produce the second biotherapeutic while equipment included in one or more processes that are downstream from the bioreactor can be similar or the same as the processes performed to produce the initial biotherapeutic. To illustrate, a first biotherapeutic can be produced by the bioreactor included in the first modular cleanroom 602 and the purification and post-viral operations can be performed by equipment included in the fourth modular cleanroom 608 and the fifth modular cleanroom 610, respectively. Additionally, the second biotherapeutic can be produced by the first additional bioreactor included in the second modular cleanroom 604 and the purification operations can also be performed by equipment included in the fourth modular cleanroom 608. Subsequent post-viral operations can be performed by equipment included in the fifth modular cleanroom 610 or the sixth modular cleanroom 612. In one or more implementations, before equipment included in at least one of the fourth modular cleanroom 608, the fifth modular cleanroom 610, or the sixth modular cleanroom 612 is reused to produce the second biotherapeutic one or more cleaning operations can take place with respect to the equipment included in at least one of the fourth modular cleanroom 608, the fifth modular cleanroom 610, or the sixth modular cleanroom 612 before the second biotherapeutic is produced. Further, before equipment included in at least one of the fourth modular cleanroom 608, the fifth modular cleanroom 610, or the sixth modular cleanroom 612 is reused to produce the second biotherapeutic, single-use components can be replaced with respect to the equipment included in at least one of the fourth modular cleanroom 608, the fifth modular cleanroom 610, or the sixth modular cleanroom 612 used to produce the second biotherapeutic.

In various implementations, the transfer of equipment and/or material throughout the production facility can be tracked using identifiers that are assigned to respective pieces of equipment, identifiers that are assigned to respective samples, identifiers that are assigned to respective storage containers, or one or more combinations thereof. In illustrative examples, individual identifiers can be encoded by at least one of an alphanumeric identifier, a barcode, a quick response (OR) code, or radio frequency identification (RFID). In this way, as materials and equipment change locations within the production facility 600, the respective characteristics of the materials and equipment can be identified at a given time.

Figure 7:
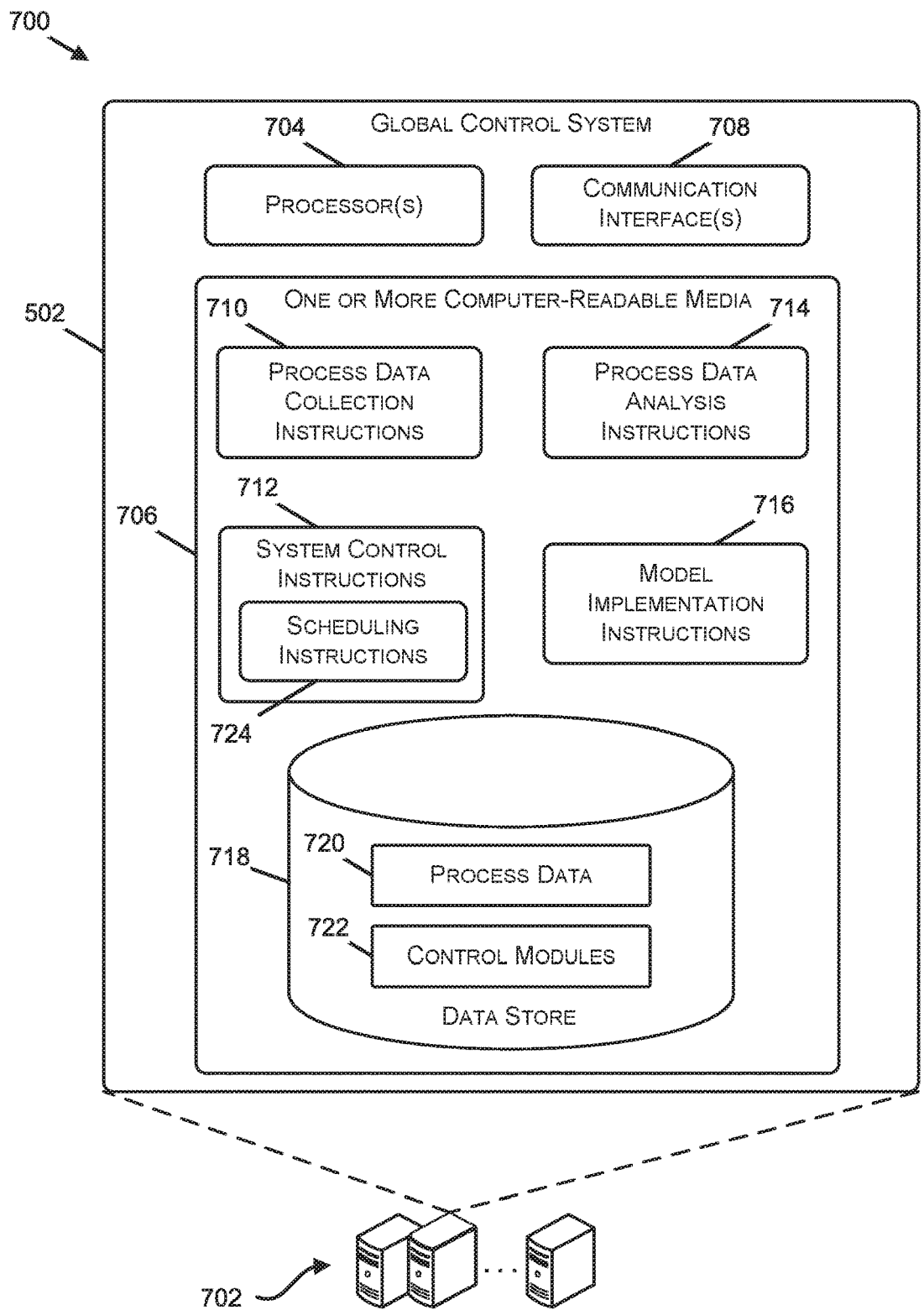
FIG. 7 illustrates some implementations of a system to control production lines that produce a purified biotherapeutic according to some implementations.

FIG. 7 illustrates some implementations of a system 700 to control production lines that produce a purified biotherapeutic. The system 700 includes a global system 502 that can be implemented by the one or more computing devices 702. In some implementations, the one or more computing devices 702 can be included in a cloud computing architecture that operates the one or more computing devices 702 on behalf of an entity implementing the global control system 502. In these scenarios, the cloud computing architecture can instantiate one or more virtual machine instances on behalf of the entity implementing the global control system 502 using the one or more computing devices 702. The cloud computing architecture can be located remote from the entity implementing the global control system 502. In additional implementations, the one or more computing devices 702 can be under the direct control of the entity implementing the global control system 502. For example, the entity implementing global control system 502 can maintain the one or more computing devices 702 to perform operations related to generating one or more models related to the efficiency, productivity, and/or control of pieces of equipment included in a production line to produce one or more biotherapeutics. In various implementations, the one or more computing devices 702 can include one or more server computers.

The global control system 502 can include one or more processors, such as processor 704. The one or more processors 704 can include at least one hardware processor, such as a microprocessor. In some cases, the one or more processors 704 can include a central processing unit (CPU), a graphics processing unit (GPU), or both a CPU and GPU, or other processing units. Additionally, the one or more processors 704 can include a local memory that may store program modules, program data, and/or one or more operating systems.

In addition, the global control system 502 can include one or more computer-readable storage media, such as computer-readable storage media 706. The computer-readable storage media 706 can include volatile and nonvolatile memory and/or removable and non-removable media implemented in any type of technology for storage of information, such as computer-readable instructions, data structures, program modules, or other data. Such computer-readable storage media 706 can include, but is not limited to, RAM, ROM, EEPROM, flash memory or other memory technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, removable storage media, or any other medium that can be used to store the desired information and that can be accessed by a computing device. Depending on the configuration of the global control system 502, the computer-readable storage media 706 can be a type of tangible computer-readable storage media and can be a non-transitory storage media.

The global control system 502 can include one or more communication interfaces 708 to communicate with other computing devices via one or more networks (not shown), such as one or more of the Internet, a cable network, a satellite network, a wide area wireless communication network, a wired local area network, a wireless local area network, or a public switched telephone network (PSTN).

The computer-readable storage media 706 can be used to store any number of functional components that are executable by the one or more processors 704. In many implementations, these functional components comprise instructions or programs that are executable by the one or more processors 704 and that, when executed, implement operational logic for performing the operations attributed to the global control system 502. Functional components of the global control system 502 that can be executed on the one or more processors 704 for implementing the various functions and features related to the control and operation of production lines producing biotherapeutics, as described herein, include process data collection instructions 710, system control instructions 712, process data analysis instructions 714, and model generating instructions 716.

Additionally, the one or more computing devices 702 can include one or more input/output devices (not shown). The one or more input/output devices can include a display device, keyboard, a remote controller, a mouse, a printer, audio input/output devices, a speaker, a microphone, a camera, and so forth The global control system 502 can also include, or be coupled to, a data store 718 that can include, but is not limited to, RAM, ROM, EEPROM, flash memory, one or more hard disks, solid state drives, optical memory (e.g. CD, DVD), or other non-transient memory technologies. The data store 718 can maintain information that is utilized by the global control system 502 to perform operations related to the control and operation of production lines that produce biotherapeutics. For example, the data store 718 can store process data 720 and control modules 722. The process data 720 can include values obtained from sensors coupled to pieces of equipment included in a production line for producing a biotherapeutic. The control modules 722 can include instructions for the control of various pieces of equipment that can be included in a production line that produces a biotherapeutic. The control modules 722 can include setpoints, threshold values, status flags, tags, identifiers, equipment characteristics, combinations thereof, and the like. In some examples, the equipment characteristics can include a type for a respective piece of equipment, a size of the piece of the equipment (e.g., capacity)

The process data collection instructions 710 can be executable by the one or more processors 704 to obtain data produced by sensors on pieces of equipment that operate as part of one or more production lines to produce a biotherapeutic. The data obtained by the process data collection instructions 710 can also include data that corresponds to diagnostic or testing procedures that are not based on sensor data. For example, the process data collection instructions 710 can obtain data that indicates a concentration of a biotherapeutic at one or more stages of the production line. In some examples when the biotherapeutic is an antibody, measurement of the concentration of the biotherapeutic can include determining the functional concentration or dilution-factor of a stock solution of antibody for a given immunoassay, which can be referred to herein as "titer". In particular implementations, the process data collection instructions 710 can send requests to one or more production facilities to obtain at least a portion of the process data 720. In additional implementations, the global control system 502 can receive portions of the process data 720 periodically and store the data in the data store 718 as the process data 720. Further, the data obtained by the process data collection instructions 710 can be requested and/or received by the global control system 502 periodically, at predetermined intervals, at irregular times, or combinations thereof.

The process data collection instructions 710 can store data obtained from the production facilities according to a schema that enables the efficient retrieval of the data. In some illustrative examples, the data obtained by the process data collection instructions 710 can be stored based on the production facility supplying the data. Additionally, the data obtained by the process data collection instructions 710 can store the data based on the types of the respective pieces of equipment associated with the data, such as bioreactor, chromatography system, filter device, pump device, temperature control device, storage container. The data obtained by the process data collection instructions 710 can also be stored based on the types of data being collected, such as pH data, temperature data, flow rate data, viable cell density data, capacitance data, volume levels data, weight data.

Further, the data obtained by the process data collection instructions 710 can be stored based on a configuration of a production line producing a biotherapeutic agent, such as the placement of various pieces of equipment within the production lines and/or whether one or more pieces of equipment included in the production lines are housed in modular cleanrooms. In various implementations, the data obtained by the process data collection instructions 710 can be stored based on the biotherapeutic produced by the production lines, cell lines used to produce the biotherapeutic, and/or reagents used in the production of the biotherapeutic agent.

The system control instructions 712 can be executable by the processors 704 to determine control settings for pieces of equipment included in production lines to produce biotherapeutics. Additionally, the system control instructions 712 can include scheduling instructions to generate control data, such as signals or commands, to send to the production facilities to use in the control of pieces of equipment included in the production lines. In particular implementations, the control data can indicate a timing for a piece of equipment to perform a specified operation and a modification or setting for the piece of equipment. For example, the scheduling instructions 724 can generate control data for a perfusion system indicating a flow rate for the perfusion system. The scheduling instructions 724 can also generate control data indicating a timing for the perfusion system to implement the flow rate. In additional examples, the scheduling instructions 724 can generate control data for a bioreactor indicating at least one of a temperature setting for the bioreactor, a pH level for the bioreactor, a feed rate for the bioreactor, or an agitation rate for the bioreactor.

In particular implementations, the system control instructions 712 can analyze the process data 720 with respect to a number of rules for the control of pieces of equipment included in a production line to produce a biotherapeutic. In certain implementations, the system control instructions 712 can analyze the process data 720 in relation to one or more policies and/or rules to determine control settings for pieces of equipment included in production lines to produce biotherapeutics. The policies and/or rules can indicate various thresholds and/or ranges of values that correspond to respective values for process variables and/or control variables. For example, the policies and/or rules can indicate at least one of pump settings or flow rates for buffer solution into a bioreactor in relation to pH levels of the bioreactor. In additional examples, the policies and/or rules can indicate agitation rates for a bioreactor based on volume of material in the bioreactor, growth rate of one or more end products, temperatures related to the bioreactor, or combinations thereof.

In some illustrative examples, the rules and/or policies can indicate actions that correspond to different volume levels of a storage container. To illustrate, a rule corresponding to a storage container coupled to a chromatography system can indicate that at a first volume of material included in the storage container, a pump of the chromatography system is stopped and that at a second volume of material included in the storage container that is higher than the first volume, a pump of the chromatography system is set to a slow setting until a third volume level of material in the storage container is reached, where the third volume is greater than the second volume. Continuing with this illustrative example, the rule can indicate that at a fourth volume of material in the storage container that is higher than the third volume the pump of the chromatography system is set to a fast setting until the third volume level is reached and that at a fifth volume that is greater than the fourth volume, material being fed into the storage container is diverted away from the storage container into a drain.

In additional illustrative examples, the rules can indicate a volume level of a first storage container that triggers material being pumped into the first storage container being diverted to a second storage container. For example, a first storage container and a second storage container can be coupled to a chromatography system. The chromatography system can pump effluent into the first storage and the system control instructions 712 can be executable to monitor the volume in the first storage container and send control data to the chromatography system or send a notification to an operator to pump effluent to the second storage container in response to the volume of material included in the first storage container being a threshold level. In further illustrative examples, the system control instructions 712 can monitor a pressure level of a filter assembly that is part of a filter bank. The system control instructions 712 can determine that the pressure level of the filter assembly has reached a threshold level and cause the scheduling instructions 724 to send control data to the filter assembly or notify an operator to divert material away from the filter assembly to another filter assembly that has a pressure less than the threshold pressure.

The system control instructions 720 can also be executable by the one or more processors 704 to determine control modules to utilize with respect to pieces of equipment included in a production line to produce a biotherapeutic. The system control instructions 720 can determine a control module 722 or a set of control modules 722 to implement for the control of a piece of equipment based on information received by the global control system 502 about the piece of equipment. In various implementations, the system control instructions 712 can obtain information about a piece of equipment including an identifier of the piece of equipment and a function of the piece of equipment. In these situations, the system control instructions 712 can determine a control module 722 or set of the control modules 722 that correspond to the identifier and function received by the global control system 502. In an illustrative example, the system control instructions 712 can receive an identifier and function for a piece of equipment that corresponds to a chromatography system, and the system control instructions 712 can identify one or more of the control modules 722 that correspond to the control of a chromatography system and implement the one or more of the control modules 722 for the control and operation of the chromatography system.

In additional illustrative examples, the system control instructions 712 can determine that an identifier and/or function of a piece of equipment changes and identify a different set of the control modules 722 to control the operation of the piece of equipment. To illustrate, the system control instructions 712 can identify one or more first control modules 722 to control the operation of a storage container based on a first identifier and a first function received by the global control system 502 with respect to the storage container. Continuing with this example, the storage container can be utilized in a different location within a production line or utilized with respect to a different production line and the system control instructions 712 can obtain information from a production facility indicating that the storage container is associated with a second identifier and a second function. The system control instructions 712 can then determine that one or more second control modules 722 are to be utilized to control the operation of the storage container based on the second identifier and the second function. In a particular illustrative example, the first identifier and the first function can indicate that the storage container operates to collect effluent from a bioreactor and the second identifier and the second function can indicate that the storage container operates to collect effluent from a chromatography system.

In situations where a production line is located in a number of modular cleanrooms, the system control instructions 712 can generate control signals that correspond to the flow of material between the modular cleanrooms. For example, the system control instructions 712 can determine a flow rate of material transferred between modular cleanrooms based on volumes of material stored in one or more storage containers and send signals to a production facility control system to cause one or more pumping devices to operate to achieve the flow rate.

In various implementations, the signals can be sent to perfusion systems, chromatography systems, and/or stand-alone pumping devices.

The process data analysis instructions 714 can be executable by the processors 704 to analyze the process data 720 and determine factors that can have at least a threshold impact on the productivity, efficiency, and/or control of a production line that produces a biotherapeutic. In illustrative examples, the productivity and/or efficiency of a production line can correspond to a yield of a biotherapeutic produced by the production line. In other illustrative examples, the productivity and/or efficiency of a production line can correspond to viable cell density associated with a biotherapeutic agent produced by the production line. In additional illustrative examples, the productivity and/or efficiency of a production line can correspond to a purity of an end product that includes a biotherapeutic agent produced by the production line. In various implementations, a first portion of the process data 720 can be utilized to train the models, while a second portion of the process data 720 can be used to validate the models. To illustrate, a portion of the process data 720 collected over a first period of time with respect to a production line can be used to train a model in relation to the productivity, efficiency, and/or control of the production line, while another portion of the process data 720 collected over a second period of time subsequent to the first period of time with respect to the production line can be utilized to validate the model.

The process data analysis instructions 714 can implement a partial least squares technique to identify the factors having at least the threshold impact on the productivity, efficiency, and/or control of the production line. The process data analysis instructions 714 can generate one or more models that can be used to predict the productivity and/or efficiency of a production line. The process data analysis instructions 714 can also generate models that predict values of the process data that can be used to control pieces of equipment included in a production line. The models can include a number of variables that each correspond to a factor having at least a threshold amount of impact on the productivity and/or efficiency of a production line. The models can also include coefficients associated with each of the variables. The coefficients can correspond to an amount of impact that a respective variable has on the productivity, efficiency, and/or control of a production line. In particular implementations, the models can include process variables that correspond to the productivity and/or efficiency of a production line and control variables that can be modified to have an impact on the process variables.

The model implementation instructions 716 can be executable by the processors 704 to implement the models generated by the process data analysis instructions 714. For example, the model implementation instructions 716 can obtain a portion of the process data 720 obtained by the process data collection instructions 710 that is related to productivity and/or efficiency of a production line and apply the portion of the process data 720 with respect to a model that predicts the productivity and/or efficiency of the production line. In particular implementations, the model implementation instructions 716 can determine that a productivity and/or efficiency predicted by the model is outside of a specified range for the productivity and/or efficiency or less than a threshold productivity and/or efficiency. In these situations, the model implementation instructions 716 can utilize the model to determine one or more control variables that can be modified to move the productivity and/or efficiency of the production line within the specified range or above the threshold productivity and/or efficiency. The model implementation instructions 716 can also determine settings for the control variables that can impact the productivity and/or efficiency of the production line.

In an illustrative example, the model implementation instructions 716 can predict that viable cell density for a production line will be less than a threshold viable cell density. The model implementation instructions 716 can also determine that pH of a bioreactor is below a threshold pH level and that a flow rate through a chromatography system is greater than a threshold flow rate. In this situation, the model implementation instructions 716 can utilize the model to determine that control variables that can impact the productivity of the production line are bleed rate of the bioreactor and flow rate of a basic buffer solution into the bioreactor. The model implementation instructions 716 can then determine that increasing the bleed rate from the bioreactor by a particular amount and increasing the flow of basic buffer solution into the bioreactor by a specified amount can increase the productivity and/or efficiency of the production line.

The model implementation instructions 716 can also operate in conjunction with the scheduling instructions 724 to determine schedules for automated control of one or more production lines. In particular implementations, the model implementation instructions 716 can implement a model generated by the process data analysis instructions 714 to predict process variables for one or more pieces of equipment included in a production line based on data obtained from the production line. The model implementation instructions 716 can also implement the model to predict productivity and/or efficiency metrics for the production line, also based on data obtained from the production line. Additionally, the model implementation instructions 716 can determine settings for pieces of equipment included in the production line that are predicted to cause the process variables and the productivity and/or efficiency metrics to be within specified ranges. The scheduling instructions 724 can then determine control signals and timing of the control signals to send to the pieces of equipment to cause the pieces of equipment to operate according to the control settings.

Although operations are described with respect to FIG. 6 as being performed by global control system 502, at least a portion of the operations can be performed by local control systems. For example, at least a portion of the operations performed by the model implementation instructions 716 can be performed by a local control system. To illustrate, the global control system 502 can generate models related to the productivity, efficiency, and/or control and a local control system can implement the models. Additionally, at least a portion of the system control instructions 712 can be performed by local control systems.

Figure 8:
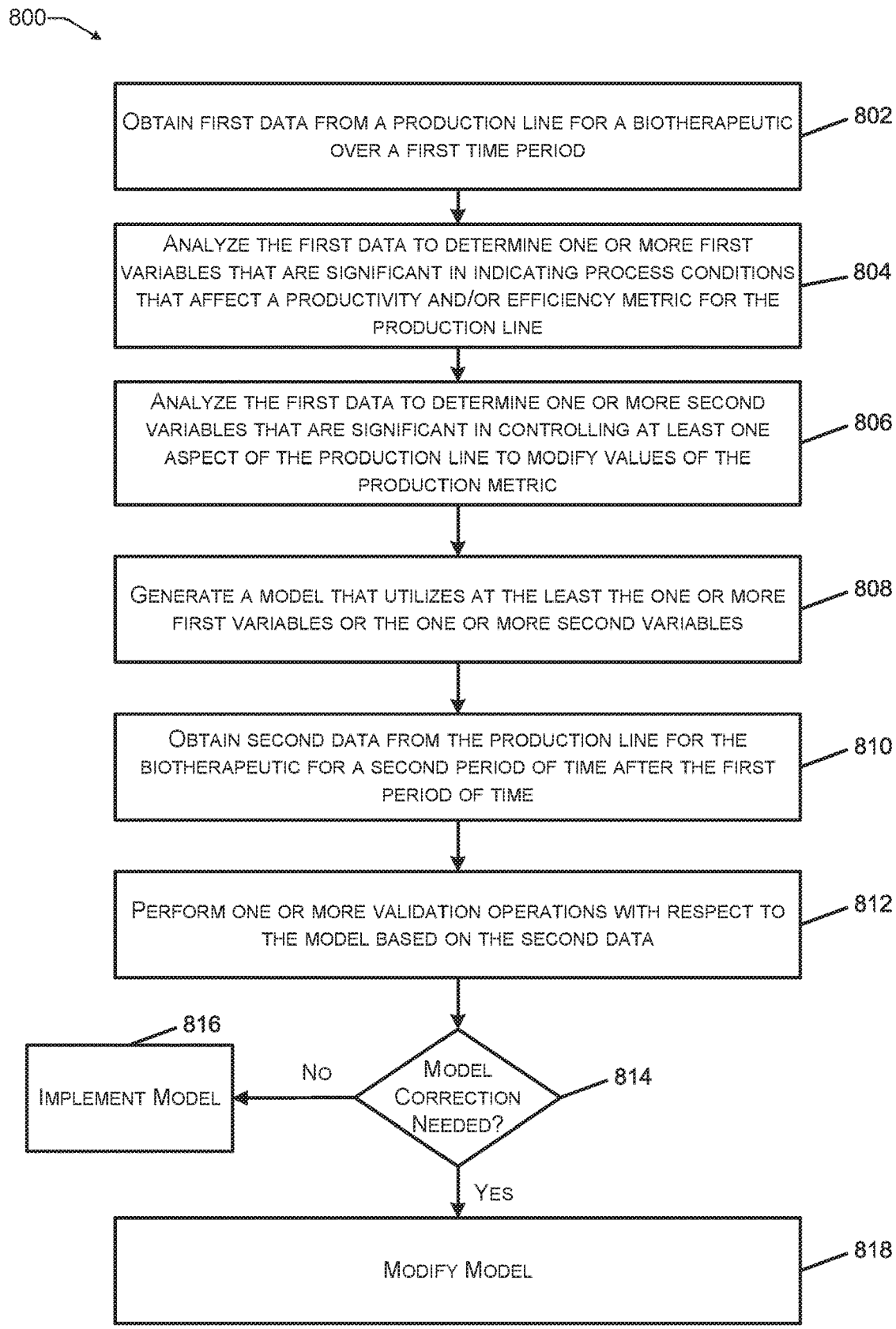
FIG. 8 is a flow diagram of an example process to generate a model used to predict values related to at least one of the production or efficiency of a production line according to some implementations.
Figure 9:
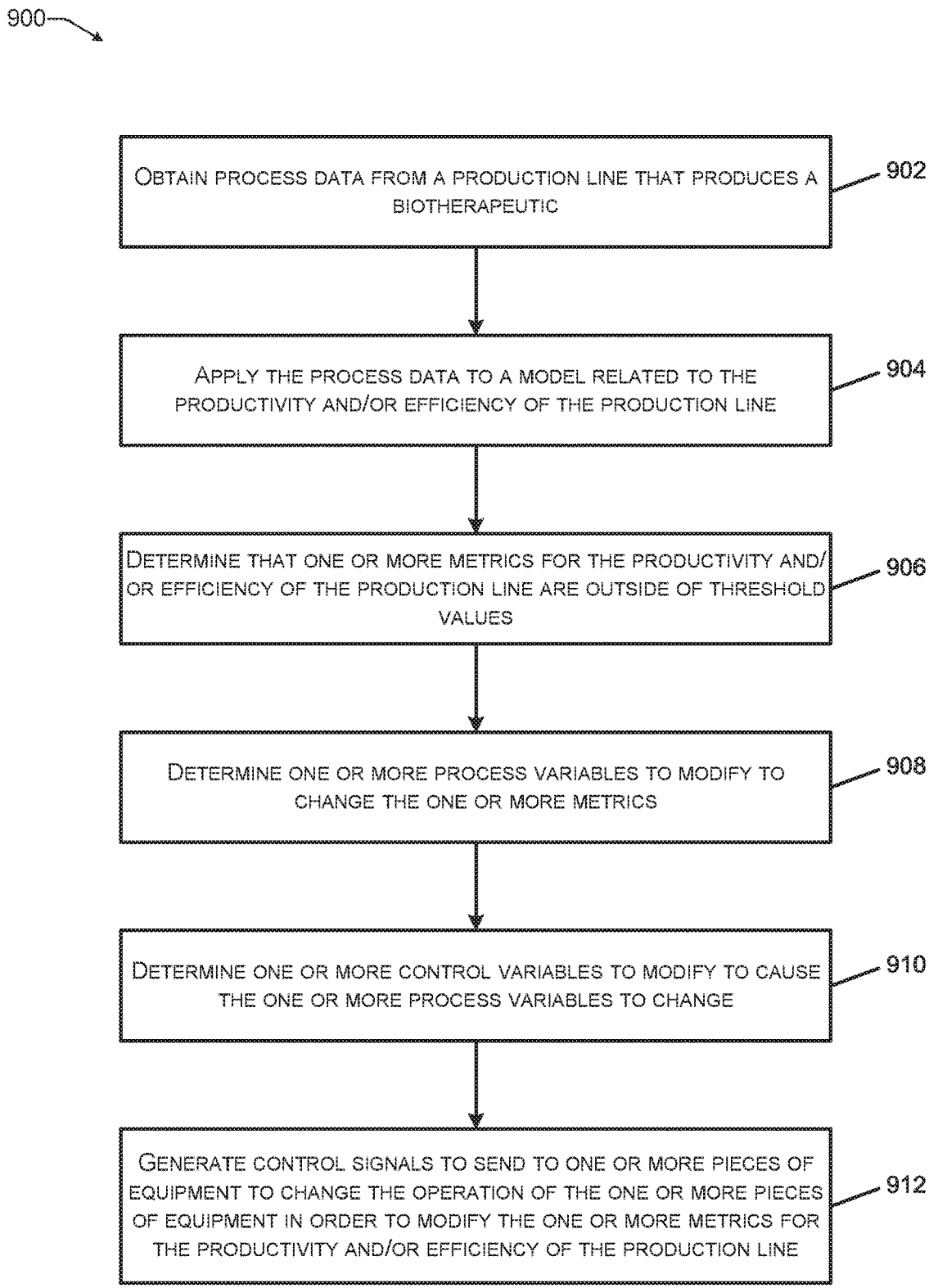
FIG. 9 is a flow diagram of an example process to implement a model used to predict values related to at least one of the production or efficiency of a production line in the control of the production line according to some implementations.
Figure 10:
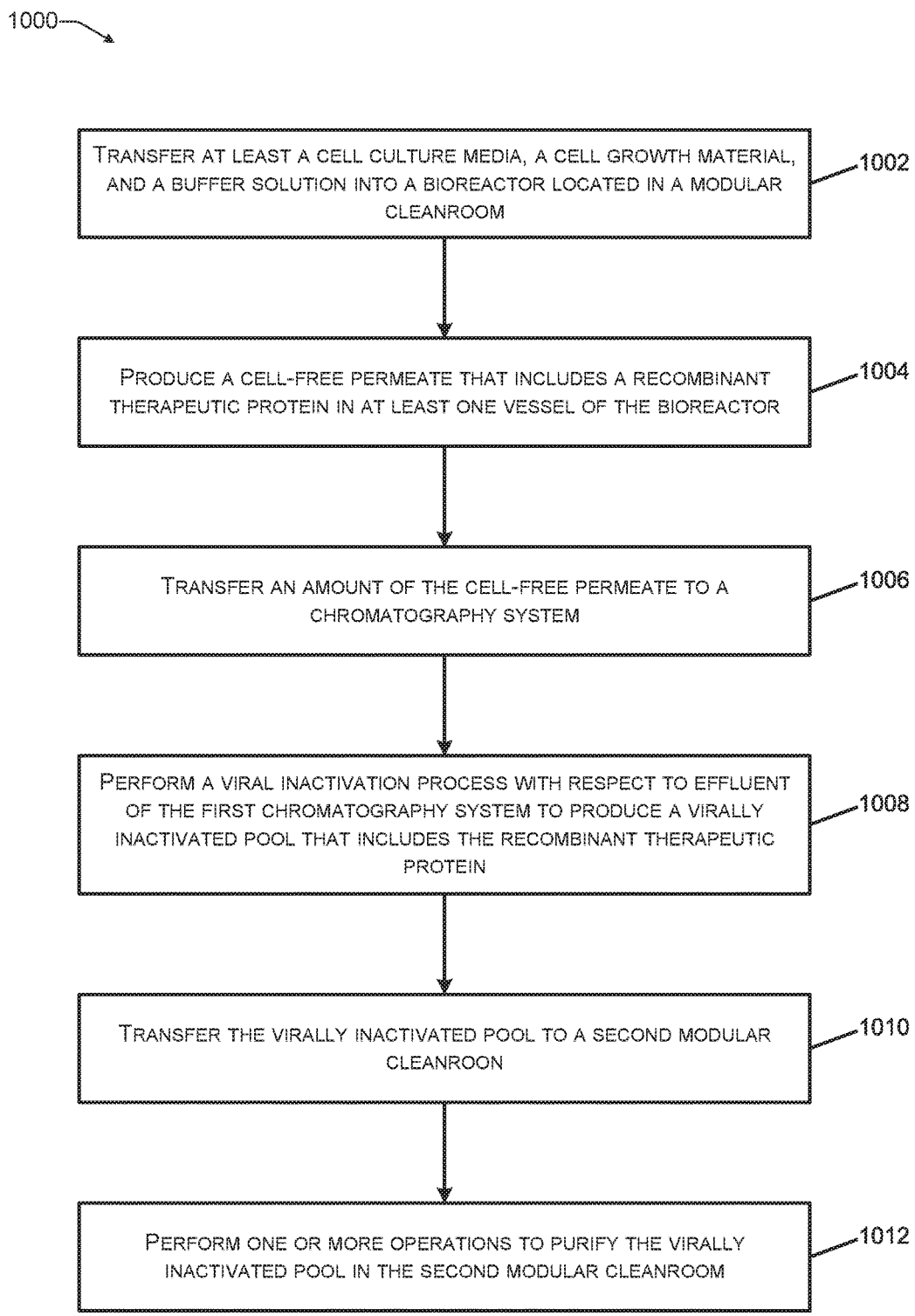
FIG. 10 is a flow diagram of an example process to produce a biotherapeutic using a production facility having multiple modular cleanrooms

FIGS. 8 and 9 illustrate example processes of generating and applying models related to the productivity, efficiency, and control of production lines that produce biotherapeutics and FIG. 10 illustrates an example process to produce a biotherapeutic using a production facility having multiple modular cleanrooms. These processes (as well as each process described herein) are illustrated as logical flow graphs, each operation of which represents a sequence of operations that can, at least in part, be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the process.

FIG. 8 is a flow diagram of an example process 800 to generate a model used to predict values related to the production and/or efficiency of a production line. At 802, the process 800 includes obtaining first data from a production line for a biotherapeutic over a first period of time. The data may be obtained by a global control system that controls the operation of a plurality of facilities that produce biotherapeutics. In some implementations, the equipment of the production line can be disposed among a number of modular cleanrooms. In additional implementations, the equipment of the production line can be disposed in a continuous space of a production facility that does not include modular cleanrooms.

At 804, the process 800 can include analyzing the first data to determine one or more first variables that are significant in indicating process conditions that affect a productivity and/or efficiency metric for the production line. The one or more first variables can be significant in indicating process conditions that affect a productivity and/or efficiency metric for the production line when measures of the one or more first variables indicate a statistical significance in relation to a productivity and/or efficiency metric. In various implementations, the one or more first variables can have at least a threshold amount of impact on the productivity and/or efficiency metric. In illustrative examples, partial least squares techniques can be implemented to determine the one or more first variables. In some implementations, the productivity and/or efficiency metric can correspond to viable cell density, titer, yield, and/or purity of a biotherapeutic.

At 806, the process 800 can include analyzing the first data to determine one or more second variables that are significant in controlling at least one aspect of the production line to modify values of the production metric. In particular implementations, the one or more second variables can have a threshold amount of impact on the one or more first variables. In illustrative implementations, partial least squares techniques can be implemented to determine the one or more second variables.

At 808, the process 800 can include generating a model that utilizes at least the one or more first variables and the one or more second variables. The model can also include one or more coefficients related to the respective one or more first variables and/or the one or more second variables. In this way, the data obtained over the first period of time can be used to train the model. At 810, the process 800 can include obtaining second data from the production line for the biotherapeutic for a second period of time after the first period of time, and, at 812, the process 800 can include performing one or more validation operations with respect to the model based on the second data. In particular implementations, the one or more validation operations can include comparing first values of the one or more productivity and/or efficiency metrics generated by applying the first data to the model with second values of the one or more productivity and/or efficiency metrics generated by applying the second data to the model.

At 814, the process 800 can include determining whether the correction of the model is needed. If correction of the model is not needed, the process 800 can proceed to 816 where the model is implemented. An illustrative example of the implementation of a model will be described with respect to FIG. 9. If correction of the model is needed, the process 800 can proceed to 818 where the model is modified. In particular implementations, the model can be modified in situations where the first values and the second values differ by more than a threshold amount. Additionally, modifying the model can include modifying at least a first variable or a second variable included in the model. That is, a variable can be removed or added to the model based on the significance of the variables changing as more data is analyzed. In other implementations, the model can be modified by changing at least one coefficient included in the model. The at least one coefficient can be modified as the significance of at least one of the first variables and/or at least one of the second variables changes as more data is analyzed. In some situations, the additional data used to modify the model can include the second data obtained over the second period of time.

FIG. 9 is a flow diagram of an example process 900 to implement a model used to predict values related to the production and/or efficiency of a production line in the control of the production line according to some implementations. At 902, the process 900 can include obtaining process data from a production line that produces a biotherapeutic. In some examples, the process data can include information obtained from sensors of pieces of equipment included in the production line. In additional examples, the process data can include data obtained by performing tests on material produced by pieces of equipment included in the production line.

At 904, the process 900 can include applying the process data to a model related to the productivity and/or efficiency of the production line. In some implementations, the model can be produced using the example process of FIG. 8. Applying the process data to the model can result in generating one or more productivity and/or efficiency metrics based on the process data.

At 906, the process 900 can include determining that one or more metrics for the productivity and/or efficiency of the production line are outside of threshold values. The one or more productivity and/or efficiency metrics being outside of the threshold values can indicate that the settings on various pieces of equipment need to be changed in order to achieve the desired productivity and/or efficiency metrics.

At 908, the process 900 can include determining one or more process variables to modify to change the one or more metrics. In particular implementations, the one or more process variables to be changed can be based on an amount of impact that changing particular process variables can have on the productivity and/or efficiency metrics. In various examples, one or more machine learning techniques can be implemented to determine the one or more process variables to modify.

At 910, the process 900 can include determining one or more control variables to modify to cause the one or more process variables to change. In some situations, the control variables that impact the process variables can be indirect. For example, cell count may not necessarily be improved by adding more cells to a production line. Rather, other variables, such as agitation rate, pH, temperature, and the like may impact cell count. The control variables that correspond to the process variables can be determined based on an analysis of previous data indicating that changes to the control variables have at least a threshold impact on the process variables. In particular implementations, machine learning techniques can be used to determine one or more control variables that have an impact on a respective process variable.

At 912, the process 900 can include generating control signals to send to one or more pieces of equipment to change the operation of the one or more pieces of equipment in order to modify the one or more metrics for the productivity and/or efficiency of the production line. In various implementations, an amount of change in the control variables and/or process variables can be determined and the control signals can correspond to an amount of change in the operation of various pieces of equipment that leads to changes in the process variables that, in turn, modify the productivity and/or efficiency metrics.

FIG. 10 is a flow diagram of an example process 1000 to produce a biotherapeutic using a production facility having multiple modular cleanrooms. The process 1000 can include, at 1002, obtaining, by a bioreactor located in a first modular cleanroom, cell culture media, a cell growth material, and a buffer solution from at least one storage container. The at least one storage container can be located outside of the first modular cleanroom. In various examples, the buffer solution can be stored in a first storage container, the cell culture media can be stored in a second storage container, and the cell growth material can be stored in a third storage container. The first modular cleanroom can have an area from about 15,000 ft$^2$ to about 50,000 ft$^2$.

Additionally, at 1004, the process 1000 can include producing a cell-free permeate that includes a recombinant therapeutic protein. The recombinant therapeutic protein can be produced in at least one vessel of the bioreactor. The at least one vessel of the bioreactor can have a capacity from about 250 L to about 2000 L. In one or more implementations, the bioreactor can produce an amount of the recombinant therapeutic protein at a rate from about 0.5 g of the recombinant therapeutic protein per liter of cell culture media per day to about 10 g of the recombinant therapeutic protein per liter of cell culture media per day.

In one or more examples, the cell free permeate can be produced by one or more operations performed by the bioreactor. In additional examples, the cell free permeate can be produced by at least one of one or more operations performed by the bioreactor or one or more operations performed by a perfusion system coupled to the bioreactor. In one or more implementations, effluent from the bioreactor can be transferred to a perfusion system and effluent from the perfusion system including the cell-free permeate can be transferred to a storage container. In various examples, the cell-free permeate can be transferred to a temperature control system from the storage container. The temperature control system, in some illustrative examples, can include a heat exchanger.

Further, the process 1000 can include, at 1006, transferring an amount of the cell-free permeate to a chromatography system. The chromatography system can also be located in the first modular cleanroom. The cell-free permeate can be transferred to the chromatography system from a storage container that is holding the cell-free permeate. Additionally, the cell-free permeate can be transferred to the chromatography system from a temperature control system that can modify the temperature of the cell-free permeate before the cell-free permeate is transferred to the chromatography system. The chromatography system can include a continuous chromatography system that produces a protein isolate fraction after 4 to 15 cycles of the continuous chromatography system. Individual cycles of the continuous chromatography system can have a duration from about 3 hours to about 12 hours. The continuous chromatography system can produce an amount of the protein isolate fraction from about 80 g/L of resin to about 140 g/L of resin. In one or more implementations, the chromatography system can include 3 to 9 columns with each column having a diameter from about 40 cm to about 100 cm and a height from about 10 cm to about 40 cm.

The effluent from the chromatography system can be transferred to one or more storage containers. The one or more storage containers can be located in the first modular cleanroom. In one or more illustrative examples, the effluent from the chromatography system can be transferred to two storage containers with the transfer of the effluent alternating between the two storage containers. For example, the chromatography system can transfer effluent to a first storage container for a first period of time. One or more sensors of the first storage container can measure a volume of the effluent from the chromatography system that is stored in the first storage container. Additionally, a rate of the transfer of effluent out of the chromatography system and an amount of time that the chromatography system has been transferring effluent to the first storage container can also be measured.

In various examples, the volume of the protein isolate fraction stored by the first container can be monitored by a control system. The control system can also monitor the rate of the transfer of the protein isolate fraction out of the chromatography system and the amount of time that the chromatography system has been transferring the protein isolate fraction to the first storage container. In one or more implementations, the control system can determine that one or more threshold criteria have been met and can cause the transfer of the protein isolate fraction to the first storage container to stop and cause the protein isolate fraction to be transferred to a second storage container. In one or more examples, the control system can determine that a volume of the protein isolate fraction stored by the first storage container corresponds to a threshold volume. In additional, the control system can determine, based on the flow rate of effluent from the chromatography system to the first storage container, that the amount of time that the protein isolate fraction has been transferred to the first storage container corresponds to a threshold period of time. The control system can then send one or more signals to cause the flow of effluent from the chromatography system to the first storage container to stop and to cause the flow of effluent from the chromatography system to the second storage container to begin. To illustrate, the control system can send one or more signals to a valve that directs the flow of the effluent from the chromatography system to cause the flow of effluent from the chromatography system to the first storage container to cease and to cause flow of effluent from the chromatography system to the second storage container to begin. Further, after a threshold condition has been satisfied with respect to the amount of protein isolate fraction stored by the second storage container, the flow of effluent from the chromatography system to the second storage container can stop and the effluent from the chromatography system can then be directed to the first storage container.

The process 1000 can also include, at 1008, performing a viral inactivation process with respect to effluent of the chromatography system to produce a virally inactivated pool that includes the recombinant therapeutic protein. The virally inactivated pool can be produced by adding an acid or a detergent to the protein isolate fraction produced by the chromatography system. The acid or detergent can be stored in one or more storage containers located outside of the first modular cleanroom. The acid or detergent can be added to the protein isolate fraction while the protein isolate fraction is stored in a storage container. In various examples, a pumping device located in the first modular cleanroom can be used to treat the protein isolate fraction produced by the chromatography system with acid or detergent to produce the virally inactivated pool.

At 1010, the process 1000 can include transferring an amount of the virally inactivated pool to a second modular cleanroom. The virally inactivated pool can be transferred to the second modular cleanroom by transferring an amount of the virally inactivated pool to an additional storage container located outside of the first modular cleanroom. In various examples, the additional storage container can be coupled to a port of the first modular cleanroom. In one or more implementations, the virally inactivated pool can be transferred to the additional storage container outside of the first modular cleanroom using an additional pumping device located in the first modular cleanroom. Additionally, the virally inactivated pool can pass through one or more filtering devices located in the first modular cleanroom before being transferred to the additional storage container located outside of the first modular cleanroom. In various examples, an amount of the virally inactivated pool can be transferred to the second modular cleanroom by coupling the additional storage container to a port of the second modular cleanroom. In additional examples, an amount of the virally inactivated pool can be transferred to the second modular cleanroom by transferring contents of the additional storage container to another storage container that is located outside of the second modular cleanroom and coupled to a port of the second modular cleanroom. The other storage container located outside of the second modular cleanroom can have a capacity that is greater than a capacity of the additional storage container that captures the virally inactivated pool from the first modular cleanroom.

The process 1000 can include, at 1012, performing one or more operations to purify the virally inactivated pool using one or more pieces of equipment in the second modular cleanroom. The virally inactivated pool can be purified using one or more additional chromatography systems located in the second modular cleanroom. In various examples, one or more resins used in the one or more chromatography systems located in the second modular cleanroom to purify the virally inactivated pool can be different from one or more resins used by the chromatography system located in the first modular cleanroom to produce the protein isolate fraction. In addition, the one or more chromatography systems included in the second modular cleanroom can implement one or more chromatographic techniques that are different from at least one chromatographic technique implemented by the chromatography system located in the first modular cleanroom. The purification processes implemented by the one or more chromatography systems located in the second modular cleanroom can produce a purified product pool. In one or more implementations, the purified product pool can be transferred to a viral filtration device. The viral filtration device can produce a virus-free filtrate. In one or more illustrative examples, the viral filtration device can be located in the second modular cleanroom.

In additional examples, further purification can be performed. For example, the virus-free filtrate can be transferred to an additional filtration device that can perform at least one of one or more ultrafiltration operations or one or more diafiltration operations to produce a purified protein drug substance. In various examples, the additional filtration device can be located in a third modular cleanroom. Amounts of the purified therapeutic protein drug substance can be transferred to a number of vials. To illustrate, one or more fill operations and/or one or more finish operations can be performed to transfer amounts of the purified therapeutic drug substance at a rate of 5 vials to 100 vials per minute. The filling of the number of vials with the purified therapeutic protein drug substance can be performed in an automated manner using at least one piece of equipment to perform the filling of the vials with the purified therapeutic protein drug substance. In one or more illustrative examples, the number of vials can individually have a volume from about 2 mL to about 40 mL.

The biotherapeutic produced using implementations of the process 1000 can take place in a production facility that can produce multiple biotherapeutics using different arrangements of equipment in the modular cleanrooms of the production facility. For example, after an amount of a first biotherapeutic is produced using a first arrangement of equipment, an amount of a second biotherapeutic can be produced using a different arrangement of equipment. In one or more examples, pieces of equipment can be added to, removed from, or change locations within one or more modular cleanrooms to create the production line used to produce the second biotherapeutic in relation to the arrangement of pieces of equipment to produce the first biotherapeutic. To illustrate, one or more filtration devices can be added to, removed from, or change locations to produce the second biotherapeutic in relation to the first arrangement of equipment used to produce the first biotherapeutic. Additionally, one or more pumping devices and/or one or more storage containers can be added to, removed from, or change locations to produce the second biotherapeutic in relation to the first arrangement of equipment used to produce the first biotherapeutic. In various examples, a chromatography system used to produce the first biotherapeutic may not be used to produce the second biotherapeutic. Further, in one or more implementations, an additional chromatography system can be used to produce the second biotherapeutic that was not used to produce the first biotherapeutic. In situations where pieces of equipment that are used to produce the first biotherapeutic are also used to produce the second biotherapeutic, single-use components of the pieces of equipment can be removed from the pieces of equipment after production of the first biotherapeutic ceases and then replaced before production of the second biotherapeutic begins. For example, after an amount of the purified therapeutic protein drug substance is produced, one or more first single-use components can be removed from at least one of the bioreactor, the chromatography system, or the additional chromatography system. Subsequently, the one or more first single-use components can be replaced with one or more second single-use components. The bioreactor can then obtain additional cell culture media, additional cell growth material, and additional buffer solution from one or more storage containers and produce an additional cell-free permeate that includes an additional recombinant therapeutic protein that is different from the initial recombinant therapeutic protein produced by the bioreactor.

Additionally, the process 1000 can be implemented in one or more scenarios where a second bioreactor is producing a biotherapeutic and operations with respect to effluent from the first bioreactor and effluent from the second bioreactor can take place concurrently. In one or implementations, the second bioreactor can be located in a same modular cleanroom as the first bioreactor. In one or more illustrative examples, at least one of the one or more ultrafiltration operations or the one or more diafiltration operations can be performed related to effluent from the first bioreactor while an amount of an additional virally inactivated pool is purified by one or more chromatography systems, where the additional virally inactivated pool is produced from effluent of the second bioreactor. In various examples, the ultrafiltration and/or diafiltration can take place in one modular cleanroom while the purification of the virally inactivated pool takes place in another modular cleanroom. Further, at least one of one or more ultrafiltration operations or one or more diafiltration operations can take place in relation to effluent produced by the first bioreactor while a viral filtration device processes an amount of an additional purified product pool that is produced from effluent of the second bioreactor. In these scenarios, the ultrafiltration and/or diafiltration can take place in one modular cleanroom while viral filtration takes place in another modular cleanroom. Still further, chromatography operations being performed in relation to effluent from a first bioreactor by one or more chromatography systems located in one modular cleanroom can take place while additional chromatography operations are performed in relation to effluent from a second bioreactor by one or more chromatography systems located in another modular cleanroom.

The subject matter described above is provided by way of illustration only and should not be construed as limiting. Furthermore, the claimed subject matter is not limited to implementations that solve any or all disadvantages noted in any part of this disclosure. Various modifications and changes can be made to the subject matter described herein without following the example configurations and applications illustrated and described, and without departing from the true spirit and scope of the present invention, which is set forth in the following claims.

EXAMPLE IMPLEMENTATIONS

1. A method comprising: obtaining a first set of data indicating a first plurality of conditions of a bioreactor system, the first set of data being obtained via at least one of a plurality of sensors of the bioreactor system or one or more external assays that measure conditions at different points in time during operation of the bioreactor system; analyzing the first set of data utilizing one or more inferential modeling techniques to determine one or more process variables that have at least a threshold impact on a productivity metric related to an effluent produced using the bioreactor system, wherein the one or more process variables correspond to at least a media component utilized in the bioreactor system to produce the effluent; analyzing the first set of data utilizing the one or more inferential modeling techniques to determine one or more control variables that have at least an additional threshold impact on the one or more process variables; generating a model that includes variables corresponding to the one or more process variables and the one or more control variables, wherein the model predicts the productivity metric; obtaining a second set of data indicating a second plurality of conditions of the bioreactor system, the second set of data being obtained via the at least one of the plurality of sensors of the bioreactor system or the one or more external assays and being obtained subsequent to the first set of data; analyzing the second set of data in accordance with the model to determine a modification to at least one of the one or more control variables to modify the productivity metric; and causing the at least one control variable to be modified according to the modification.

2. The method of 1, wherein: the bioreactor system is included in a first production facility and an additional bioreactor system is included in a second production facility; the first set of data includes an additional plurality of conditions of the additional bioreactor system, the first set of data also being obtained via at least one of a plurality of additional sensors of the additional bioreactor system or one or more external assays that measure conditions at different points in time during operation of the additional bioreactor system.

3. The method of 2, wherein: the bioreactor system is included in a modular cleanroom of a first plurality of modular cleanrooms included in the first production facility; and the additional bioreactor system is included in an additional modular cleanroom of a second plurality of modular cleanrooms included in the second production facility.

4. The method of 2 or 3, wherein: a first volume of the bioreactor system and a second volume of the additional bioreactor system are substantially the same; first cell media fed into the bioreactor system and second cell media of the additional bioreactor system include a same cell line; and a first biotherapeutic produced by the bioreactor system and a second biotherapeutic produced by the additional bioreactor system are the same.

5. The method of any one of 1-4, wherein the one or more inferential modeling techniques include a partial least squares technique.

6. The method of any one of 1-5, further comprising: obtaining a third set of data indicating a third plurality of conditions of a plurality of pieces of equipment included in a production line to produce a biotherapeutic, the production line including the bioreactor system and a chromatography system, the third set of data being obtained via at least one of a plurality of sensors of the plurality of pieces of equipment or one or more external assays that measure conditions at different points in time during operation of the plurality of pieces of equipment; analyzing the third set of data utilizing one or more inferential modeling techniques to determine one or more additional process variables that have at least a threshold impact on an additional productivity metric related to the biotherapeutic produced using the production line; analyzing the third set of data utilizing the one or more inferential modeling techniques to determine one or more additional control variables that have at least an additional threshold impact on the one or more additional process variables; and generating an additional model that includes additional variables corresponding to the one or more additional process variables and the one or more additional control variables, wherein the model predicts the additional productivity metric.

7. The method of any one of 1-6, wherein the productivity metric includes viable cell density and the one or more process variables include at least one of flow rate of material through a piece of equipment, temperature of a material included in a piece of equipment, or rate of agitation of material included in a piece of equipment.

8. The method of any one of 1-7, wherein the bioreactor system is coupled to a perfusion system.

9. The method of any one of 1-7, wherein the bioreactor system is part of a production line that utilizes batch techniques to produce a recombinant therapeutic protein.

10. A production facility to produce a biotherapeutic, the production facility comprising: a first modular cleanroom comprising a first plurality of pieces of equipment to produce an effluent that includes the biotherapeutic, the first plurality of pieces of equipment including a bioreactor; a second modular cleanroom comprising a second plurality of pieces of equipment to purify the end product, the second plurality of pieces of equipment including at least a filter system; and a staging area including a plurality of storage containers, a first portion of the plurality of storage containers storing cell media for the bioreactor system and a second portion of the plurality of storage containers storing buffer solution for at least one piece of equipment included in the first plurality of pieces of equipment and for at least one piece of equipment included in the second plurality of pieces of equipment.

11. The production facility of 10, wherein: the first plurality of pieces of equipment include a chromatography system coupled to the bioreactor system and the chromatography system purifies the effluent produced by the bioreactor system to produce a purified end product; and the first plurality of pieces of equipment include a storage container that captures the purified end product, and buffer solution is added to the storage container to produce a viral inactivated pool.

12. The production facility of 11, wherein: the bioreactor system is disposed on a first skid, the first skid including a first plurality of communication interfaces; and the chromatography system is disposed on a second skid, the second skid including a second plurality of communication interfaces with the storage container being coupled to a communication interface of the plurality of communication interfaces.

13. The production facility of 12, wherein a dongle is coupled to the storage container, the dongle storing an identifier and a function that corresponds to the storage container.

14. The production facility of 13, further comprising a local control system, the local control system to send first signals to at least a portion of the first plurality of pieces of equipment to control operations of the at least a portion of the first plurality of pieces of equipment and to send second signals to at least a portion of the second plurality of pieces of equipment to control operation of the at least a portion of the second plurality of pieces of equipment, and wherein the local control system receives the identifier and the function from the dongle.

15. The production facility of 14 or 15, wherein the local control system identifies, based at least partly on the identifier and the function, one or more control modules that are executable to control operation of the storage container according to the function.

16. The production facility of 14, wherein: the local control system is in electronic communication with a global control system; the global control system analyzes data obtained from the local control system and an additional local control system to generate a model to predict a metric corresponding to productivity of a production line included in the facility, the additional local control system being located in an additional facility that produces an additional biotherapeutic.

17. The production facility of any one of 10-15, further comprising a third modular cleanroom that includes at least one additional chromatography system, the additional chromatography system performing viral filtration of a viral inactivated pool obtained from the first modular cleanroom.

18. The production facility of 17, wherein the filter system performs ultrafiltration/diafiltration operations with respect to effluent obtained from the additional chromatography system.

19. A system to produce one or more biotherapeutics, the system comprising: a production facility that includes: a first modular cleanroom comprising a first plurality of pieces of equipment to produce an effluent that includes a biotherapeutic, the first plurality of pieces of equipment including a bioreactor; a second modular cleanroom comprising a second plurality of pieces of equipment to purify the effluent produced by the first plurality of pieces of equipment, the second plurality of pieces of equipment including at least a filter system; and a staging area including a plurality of storage containers, a first portion of the plurality of storage containers storing cell media for the bioreactor and a second portion of the plurality of storage containers storing buffer solution for at least one piece of equipment included in the first plurality of pieces of equipment and for at least one piece of equipment included in the second plurality of pieces of equipment.

20. The system of 19, wherein: the first plurality of pieces of equipment include a chromatography system coupled to the bioreactor and the chromatography system purifies a bioreactor effluent produced by the bioreactor to produce a protein isolate fraction; and the first plurality of pieces of equipment include a storage container that captures the purified bioreactor effluent, and a solution including at least one of an acid or a detergent is added to the purified bioreactor effluent to produce a virally inactivated pool.

21. The system of 20, wherein the second plurality of pieces of equipment include at least one additional chromatography system, the at least one additional chromatography system to perform one or more additional purification operations in relation to the virally inactivated pool to produce a purified product pool.

22. The system of 21, further comprising a viral filtration device filter system to perform one or more viral filtration operations with respect to the purified product pool to produce a virus-free filtrate.

23. The system of 20, wherein: the chromatography system includes a continuous chromatography system having 3 to 9 columns with each of the columns having a diameter from about 40 cm to about 100 cm, and a height from about 10 cm to about 40 cm; and the chromatography system produces an amount of the protein isolate fraction from about 80 g/L of resin to about 140 g/L of resin within 4 to 15 cycles of the chromatography system, each cycle having a duration from about 3 hours to about 12 hours.

24. The system of any one of 20-23, wherein: the modular cleanroom has an area from about 15,000 ft$^2$ to about 50,000 ft$^2$; and the bioreactor includes at least one vessel to produce the bioreactor effluent that includes a recombinant therapeutic protein, the at least one vessel having a capacity from about 250 L to about 2000 L.

25. The system of any one of 20-24, further comprising a perfusion system that transfers feed material into the bioreactor and that removes effluent from the bioreactor, the perfusion system being coupled to the bioreactor.

26. The system of any one of 19-25, comprising: one or more processors; and one or more computer-readable storage media storing computer-readable instructions that, when executed by the one or more processors, cause the one or more processors to perform operations comprising: obtaining a first set of data indicating a first plurality of conditions of the bioreactor, the first set of data being obtained via at least one sensor of a plurality of sensors of the bioreactor or one or more external assays that measure conditions at different points in time during operation of the bioreactor; analyzing the first set of data utilizing one or more inferential modeling techniques to determine one or more process variables that have at least a first threshold impact on a productivity metric related to the bioreactor effluent; analyzing the first set of data utilizing the one or more inferential modeling techniques to determine one or more control variables that have at least a second threshold impact on the one or more process variables; generating a model that includes variables corresponding to the one or more process variables and the one or more control variables, wherein the model predicts the productivity metric; obtaining a second set of data indicating a second plurality of conditions of the bioreactor, the second set of data being obtained via the at least one of the plurality of sensors of the bioreactor or the one or more external assays and being obtained subsequent to the first set of data; analyzing the second set of data in accordance with the model to determine a modification to at least one control variable of the one or more control variables to modify the productivity metric; and causing the at least one control variable to be modified according to the modification.

27. The system of 26, wherein: the production facility is a first production facility and the bioreactor is a first bioreactor; a second bioreactor is included in a second production facility; and the first set of data includes an additional plurality of conditions of the second bioreactor, a portion of the first set of data being obtained via at least one of a plurality of additional sensors of the second bioreactor or one or more external assays that measure conditions at different points in time during operation of the second bioreactor.

28. The system of one of 26 or 27, comprising: one or more additional computer-readable storage media storing computer-readable instructions that, when executed by the one or more processors, cause the one or more processors to perform additional operations comprising: obtaining a third set of data indicating a third plurality of conditions of a production line that produces a purified therapeutic protein drug substance, the production line including the first plurality of pieces of equipment and the second plurality of pieces of equipment, the third set of data being obtained via at least one of a plurality of additional sensors of the production line or one or more additional external assays that measure conditions at different points in time during operation of the production line; analyzing the third set of data utilizing the one or more inferential modeling techniques to determine one or more additional process variables that have at least a first additional threshold impact on an additional productivity metric related to the purified therapeutic protein drug substance produced using the production line; analyzing the third set of data utilizing the one or more inferential modeling techniques to determine one or more additional control variables that have at least a second additional threshold impact on the one or more additional process variables; and generating an additional model that includes additional variables corresponding to the one or more additional process variables and the one or more additional control variables, wherein the model predicts the additional productivity metric, the productivity metric includes viable cell density, and the additional productivity metric includes yield of the purified therapeutic protein drug substance.

29. The system of 19, wherein: the first modular cleanroom includes: a perfusion system coupled to the bioreactor; a first storage container to store a cell free permeate that includes a recombinant therapeutic protein produced by the bioreactor; a first, continuous chromatography system coupled to the first storage container, the first continuous chromatography system to produce a protein isolate fraction; a second storage container coupled to the first, continuous chromatography system to store a first amount of the protein isolate fraction; a third storage container coupled to the first, continuous chromatography system to store a second amount of the protein isolate fraction; a first pump device to transfer a virally inactivated pool to a fourth storage container, the virally inactivated pool being produced by adding at least one of an acid or a detergent to the protein isolate fraction; and a second pump device to transfer the virally inactivated pool to a sixth storage container located outside of the first modular cleanroom in the staging area via at least one filter device; the second modular cleanroom includes: a temperature control unit to transfer the virally inactivated pool from a seventh storage container located outside of the second modular cleanroom into a second chromatography system and to transfer an amount of a buffer solution into the second chromatography system from an eighth storage container located outside of the second modular container in the staging area, the second chromatography system to purify the virally inactivated pool; a ninth storage container to store effluent from the second chromatography system; a third chromatography system to purify the effluent from the second chromatography system to produce a purified product pool, the third chromatography system coupled to a tenth storage container for storing a buffer solution, the tenth storage container located outside of the second modular cleanroom in the staging area; and a third pump device to feed the purified product pool to a viral filtration device located in the second modular cleanroom, the viral filtration device to produce a virus-free filtrate; and a third modular cleanroom includes: an eleventh storage container to store the virus-free filtrate; a filter device to perform at least one of one or more ultrafiltration operations or one or more diafiltration operations with respect to the virus-free filtrate to produce a purified therapeutic protein drug substance; and at least one vial filling device to fill a plurality of vials with the purified therapeutic protein drug substance.

30. A method to produce one or more biotherapeutics, the method comprising: obtaining, by a bioreactor located in a first modular cleanroom, cell culture media, a cell growth material, and a buffer solution from at least one storage container; producing a cell-free permeate that includes a recombinant therapeutic protein, wherein the recombinant therapeutic protein is produced in at least one vessel of the bioreactor; transferring an amount of the cell-free permeate to a chromatography system; performing a viral inactivation process with respect to effluent of the chromatography system to produce a virally inactivated pool that includes the recombinant therapeutic protein; transferring an amount of the virally inactivated pool to a second modular cleanroom; and performing one or more operations to purify the virally inactivated pool using one or more pieces of equipment in the second modular cleanroom.

31. The method of 30, comprising: transferring effluent from the bioreactor to a perfusion system, the bioreactor producing an amount of the recombinant therapeutic protein at a rate from about 0.5 g of the recombinant therapeutic protein per liter of cell culture media per day to about 10 g of the recombinant therapeutic protein per liter of cell culture media per day; transferring effluent from the perfusion system to at least one storage container, the effluent from the perfusion system including the cell-free permeate; and transferring the amount of the cell free-permeate to a temperature control system before transferring the amount of the cell-free permeate to the chromatography system.

32. The method of 30 or 31, comprising: transferring a first amount of effluent from the chromatography system to a first storage container for a first period of time; determining that a second amount of the effluent from the chromatography system is to be transferred to a second storage container based on the first period of time corresponding to a threshold period of time or based on a volume of the first amount of the effluent in the first storage container corresponding to a threshold volume; causing the effluent from the chromatography system to stop flowing to the first storage container; and causing the effluent from the chromatography system to flow to the second storage container.

33. The method of any one of 30-32, wherein: the one or more operations to purify the virally inactivated pool are performed by an additional chromatography system located in the second modular cleanroom; first columns of the chromatography system include a first resin and second columns of the additional chromatography system include a second resin that is different from the first resin; the one or more operations to purify the virally inactivated pool produce a purified product pool; and the method comprises transferring the purified product pool to a viral filtration device located in the second modular cleanroom to produce a virus-free filtrate.

34. The method of 33, wherein transferring the amount of the virally inactivated pool to the second modular cleanroom includes: transferring the amount of the virally inactivated pool to a one or more first storage containers located outside of the first modular cleanroom and coupled to one or more first ports of the first modular cleanroom; and transferring the amount of the virally inactivated pool from the one or more first storage containers to one or more second storage containers, the one or more second storage containers being located outside of the second modular cleanroom and coupled to one or more second ports of the second modular cleanroom, the one or more second ports being coupled to the additional chromatography system located in the second modular cleanroom.

35. The method of 33, comprising: transferring an amount of the virus-free filtrate to a filter device included in a third modular cleanroom; performing, by the filter device, at least one of one or more ultrafiltration operations or one or more diafiltration operations to produce a purified therapeutic protein drug substance; and transferring an amount of the purified therapeutic protein drug substance to a number of vials at a rate of 5 vials to 100 vials per minute, the number of vials individually having a volume from about 2 mL to about 40 mL.

36. The method of 35, wherein the bioreactor is included in a production facility having an additional bioreactor, and the method comprises: performing the at least one of the one or more ultrafiltration operations or the one or more diafiltration operations while an amount of an additional virally inactivated pool is processed by the additional chromatography system, the additional virally inactivated pool being produced from effluent of the additional bioreactor.

37. The method of 35, wherein the bioreactor is included in a production facility having an additional bioreactor, and the method comprises: performing the at least one of the one or more ultrafiltration operations or the one or more diafiltration operations while the viral filtration device processes an amount of an additional purified product pool that is produced from effluent of the additional bioreactor.

38. The method of 35, wherein: the bioreactor is included in a production facility having an additional bioreactor; one or more first operations are performed by one or more first pieces of equipment located in the first modular cleanroom with respect to a first amount of effluent produced by the additional bioreactor while one or more second operations are performed by one or more second pieces of equipment located in the second modular cleanroom with respect to a second amount of the effluent produced by the bioreactor; and the one or more first operations being performed by the chromatography system and the one or more second operations being performed by at least one of the additional chromatography system or the viral filtration device.

39. The method of any one of 35-38, wherein the additional bioreactor is located in the first modular cleanroom.

40. The method of any one of 35-39 comprising: after an amount of the purified therapeutic protein drug substance is produced, removing one or more first single-use components from at least one of the bioreactor, the chromatography system, or the additional chromatography system; replacing the one or more first single-use components with one or more second single-use components; obtaining, by the bioreactor, additional cell culture media, additional cell growth material, and additional buffer solution from one or more storage containers; and producing an additional cell-free permeate that includes an additional recombinant therapeutic protein that is different from the recombinant therapeutic protein.

41. The method of any one of 35-39, wherein the purified therapeutic protein drug substance is produced by a first production line having a first arrangement of a first plurality of pieces of equipment located in the first modular cleanroom, the second modular cleanroom, and the third modular cleanroom and the method comprises: modifying the first arrangement of the first plurality of pieces of equipment to produce a second production line having a second arrangement of a second plurality of pieces of equipment located in the first modular cleanroom, the second modular cleanroom, and the third modular cleanroom, the second arrangement of the second plurality of pieces of equipment being produced by at least one of: removing a piece of equipment included in the first plurality of pieces of equipment from the first modular cleanroom, the second modular cleanroom, or the third modular cleanroom; adding a first additional piece of equipment to the first plurality of pieces of equipment in the first modular cleanroom, the second modular cleanroom, or the third modular cleanroom; or changing a location of a second additional piece of equipment included in the first plurality of pieces of equipment.

What is claimed is:

1. A system to produce one or more biotherapeutics, the system comprising:
 a production facility that includes:
  a first modular cleanroom comprising a first plurality of pieces of equipment to produce an effluent that includes a biotherapeutic, the first plurality of pieces of equipment including a bioreactor;
  a second modular cleanroom comprising a second plurality of pieces of equipment to purify the effluent produced by the first plurality of pieces of equipment, the second plurality of pieces of equipment including at least a filter system;
a staging area including a plurality of storage containers, a first portion of the plurality of storage containers storing cell culture media and cell growth material for the bioreactor and a second portion of the plurality of storage containers storing buffer solution for at least one piece of equipment included in the first plurality of pieces of equipment and for at least one piece of equipment included in the second plurality of pieces of equipment;
one or more processors; and
one or more computer-readable storage media storing computer-readable instructions that, when executed by the one or more processors, cause the one or more processors to perform operations comprising:
obtaining a first set of data indicating a first plurality of conditions of the bioreactor, the first set of data being obtained via at least one sensor of a plurality of sensors of the bioreactor or one or more external assays that measure conditions at different points in time during operation of the bioreactor;
analyzing the first set of data utilizing one or more inferential modeling techniques to determine one or more process variables that have at least a first threshold impact on a productivity metric related to a bioreactor effluent;
analyzing the first set of data utilizing the one or more inferential modeling techniques to determine one or more control variables that have at least a second threshold impact on the one or more process variables;
generating a model that includes variables corresponding to the one or more process variables and the one or more control variables, wherein the model predicts the productivity metric;
obtaining process data from at least one of one or more first pieces of equipment of the first plurality of pieces of equipment or one or more second pieces of equipment of the second plurality of pieces of equipment;
applying the process data to the model to determine values of the productivity metric;
responsive to determining that at least a portion of the values of the productivity metric are outside of a threshold range of values, determining, by applying one or more machine learning techniques to the process data, at least one process variable to modify to change the productivity metric;
determining at least one control variable to modify to cause additional values of the at least one process variable to change;
sending control signals to one or more pieces of equipment, the control signals indicating control settings of the one or more pieces of equipment to modify the at least one control variable in a manner that modifies the productivity metric; and
causing operation of the one or more pieces of equipment to change based on the control signals.

2. The system of claim 1, wherein:
the first plurality of pieces of equipment include a chromatography system coupled to the bioreactor and the chromatography system purifies the bioreactor effluent produced by the bioreactor to produce a protein isolate fraction; and
the first plurality of pieces of equipment include a storage container that captures purified bioreactor effluent, and a solution including at least one of an acid or a detergent is added to the purified bioreactor effluent to produce a virally inactivated pool.

3. The system of claim 2, wherein the second plurality of pieces of equipment include at least one additional chromatography system, the at least one additional chromatography system to perform one or more additional purification operations in relation to the virally inactivated pool to produce a purified product pool; and
the system further comprises a viral filtration device filter system to perform one or more viral filtration operations with respect to the purified product pool to produce a virus-free filtrate.

4. The system of claim 2, wherein:
the chromatography system includes a continuous chromatography system having 3 to 9 columns with each of the columns having a diameter from about 40 cm to about 100 cm, and a height from about 10 cm to about 40 cm; and
the chromatography system produces an amount of the protein isolate fraction from about 80 g/L of resin to about 140 g/L of resin within 4 to 15 cycles of the chromatography system, each cycle having a duration from about 3 hours to about 12 hours.

5. The system of claim 2, wherein:
at least one of the first modular cleanroom or the second modular cleanroom has an area from about 15,000 ft$^2$ to about 50,000 ft$^2$, and
the bioreactor includes at least one vessel to produce the bioreactor effluent that includes a recombinant therapeutic protein, the at least one vessel having a capacity from about 250 L to about 2000 L; and
the system further comprises a perfusion system that transfers feed material into the bioreactor and that removes the effluent from the bioreactor, the perfusion system being coupled to the bioreactor.

6. The system of claim 1,
wherein the one or more computer-readable storage media store additional computer-readable instructions that, when executed by the one or more processors, cause the one or more processors to perform additional operations comprising:
obtaining a second set of data indicating a second plurality of conditions of the bioreactor, the second set of data being obtained via the at least one of the plurality of sensors of the bioreactor or the one or more external assays and being obtained subsequent to the first set of data;
analyzing the second set of data in accordance with the model to determine a modification to at least one control variable of the one or more control variables to modify the productivity metric; and
causing the at least one control variable to be modified according to the modification.

7. The system of claim 6, wherein:
the production facility is a first production facility and the bioreactor is a first bioreactor;
a second bioreactor is included in a second production facility; and
the first set of data includes an additional plurality of conditions of the second bioreactor, a portion of the first set of data being obtained via at least one of a plurality of additional sensors of the second bioreactor or one or more external assays that measure conditions at different points in time during operation of the second bioreactor.

8. The system of claim 6, comprising:
one or more additional computer-readable storage media storing computer-readable instructions that, when executed by the one or more processors, cause the one or more processors to perform additional operations comprising:
obtaining a third set of data indicating a third plurality of conditions of a production line that produces a purified therapeutic protein drug substance, the production line including the first plurality of pieces of equipment and the second plurality of pieces of equipment, the third set of data being obtained via at least one of a plurality of additional sensors of the production line or one or more additional external assays that measure conditions at different points in time during operation of the production line;
analyzing the third set of data utilizing the one or more inferential modeling techniques to determine one or more additional process variables that have at least a first additional threshold impact on an additional productivity metric related to the purified therapeutic protein drug substance produced using the production line;
analyzing the third set of data utilizing the one or more inferential modeling techniques to determine one or more additional control variables that have at least a second additional threshold impact on the one or more additional process variables; and
generating an additional model that includes additional variables corresponding to the one or more additional process variables and the one or more additional control variables, wherein the model predicts the additional productivity metric, the productivity metric includes viable cell density, and the additional productivity metric includes yield of the purified therapeutic protein drug substance.

9. The system of claim 1, wherein:
the first modular cleanroom includes:
a perfusion system coupled to the bioreactor;
a first storage container to store a cell free permeate that includes a recombinant therapeutic protein produced by the bioreactor;
a first, continuous chromatography system coupled to the first storage container, the first continuous chromatography system to produce a protein isolate fraction;
a second storage container coupled to the first, continuous chromatography system to store a first amount of the protein isolate fraction;
a third storage container coupled to the first, continuous chromatography system to store a second amount of the protein isolate fraction;
a first pump device to transfer a virally inactivated pool to a fourth storage container, the virally inactivated pool being produced by adding at least one of an acid or a detergent to the protein isolate fraction; and
a second pump device to transfer the virally inactivated pool to a sixth storage container located outside of the first modular cleanroom in the staging area via at least one filter device;
the second modular cleanroom includes:
a temperature control unit to transfer the virally inactivated pool from a seventh storage container located outside of the second modular cleanroom into a second chromatography system and to transfer an amount of a buffer solution into the second chromatography system from an eighth storage container located outside of the second modular cleanroom in the staging area, the second chromatography system to purify the virally inactivated pool;
a ninth storage container to store effluent from the second chromatography system;
a third chromatography system to purify the effluent from the second chromatography system to produce a purified product pool, the third chromatography system coupled to a tenth storage container for storing a buffer solution, the tenth storage container located outside of the second modular cleanroom in the staging area; and
a third pump device to feed the purified product pool to a viral filtration device located in the second modular cleanroom, the viral filtration device to produce a virus-free filtrate; and
a third modular cleanroom includes:
an eleventh storage container to store the virus-free filtrate;
a filter device to perform at least one of one or more ultrafiltration operations or one or more diafiltration operations with respect to the virus-free filtrate to produce a purified therapeutic protein drug substance; and
at least one vial filling device to fill a plurality of vials with the purified therapeutic protein drug substance.

10. A method to produce one or more biotherapeutics, the method comprising:
obtaining, by a bioreactor located in a first modular cleanroom of a production facility, cell culture media, a cell growth material, and a buffer solution from a plurality of storage containers located in a staging area of the production facility, wherein the first modular cleanroom includes a first plurality of pieces of equipment and a first portion of the plurality of storage containers supply the cell culture media and the cell growth material and a second portion of the plurality of storage containers supply the buffer solution:
purifying, by a second plurality of pieces of equipment located in a second modular cleanroom of the production facility, an effluent produced by the first plurality of pieces of equipment, wherein the second plurality of pieces of equipment include at least a filter system and the buffer solution is supplied from the second portion of the plurality of storage containers to at least one piece of equipment included in the second plurality of pieces of equipment:
obtaining, by a computing system of the production facility, a first set of data indicating a first plurality of conditions of the bioreactor, the first set of data being obtained via at least one sensor of a plurality of sensors of the bioreactor or one or more external assays that measure conditions at different points in time during operation of the bioreactor;
analyzing, by the computing system, the first set of data utilizing one or more inferential modeling techniques to determine one or more process variables that have at least a first threshold impact on a productivity metric related to a bioreactor effluent;
analyzing, by the computing system, the first set of data utilizing the one or more inferential modeling techniques to determine one or more control variables that have at least a second threshold impact on the one or more process variables;
generating, by the computing system, a model that includes variables corresponding to the one or more process variables and the one or more control variables, wherein the model predicts the productivity metric;

obtaining, by the computing system, process data from at least one of one or more first pieces of equipment of the first plurality of pieces of equipment or one or more second pieces of equipment of the second plurality of pieces of equipment;

applying, by the computing system, the process data to the model to determine values of the productivity metric;

responsive to determining that at least a portion of the values of the productivity metric are outside of a threshold range of values, determining, by the computing system applying one or more machine learning techniques to the process data, at least one process variable to modify to change the productivity metric;

determining, by the computing system, at least one control variable to modify to cause additional values of the at least one process variable to change;

sending, by the computing system, control signals to one or more pieces of equipment, the control signals indicating control settings of the one or more pieces of equipment to modify the at least one control variable in a manner that modifies the productivity metric; and causing, by the computing system, operation of the one or more pieces of equipment to change based on the control signals.

11. The method of claim 10, comprising:

producing a cell-free permeate that includes a recombinant therapeutic protein, wherein the recombinant therapeutic protein is produced in at least one vessel of the bioreactor;

transferring an amount of the cell-free permeate to a chromatography system;

performing a viral inactivation process with respect to effluent of the chromatography system to produce a virally inactivated pool that includes the recombinant therapeutic protein;

transferring an amount of the virally inactivated pool to a second modular cleanroom;

performing one or more operations to purify the virally inactivated pool using one or more pieces of second plurality of pieces of equipment in the second modular cleanroom;

transferring the effluent from the bioreactor to a perfusion system, the bioreactor producing an amount of the recombinant therapeutic protein at a rate from about 0.5 g of the recombinant therapeutic protein per liter of cell culture media per day to about 10 g of the recombinant therapeutic protein per liter of cell culture media per day;

transferring effluent from the perfusion system to at least one storage container, the effluent from the perfusion system including the cell-free permeate; and transferring the amount of the cell-free permeate to a temperature control system before transferring the amount of the cell-free permeate to the chromatography system.

12. The method of claim 11, comprising:

transferring a first amount of effluent from the chromatography system to a first storage container for a first period of time;

determining that a second amount of the effluent from the chromatography system is to be transferred to a second storage container based on the first period of time corresponding to a threshold period of time or based on a volume of the first amount of the effluent from the chromatography system in the first storage container corresponding to a threshold volume;

causing the effluent from the chromatography system to stop flowing to the first storage container; and causing the effluent from the chromatography system to flow to the second storage container.

13. The method of claim 11, wherein:

the one or more operations to purify the virally inactivated pool are performed by an additional chromatography system located in the second modular cleanroom;

first columns of the chromatography system include a first resin and second columns of the additional chromatography system include a second resin that is different from the first resin;

the one or more operations to purify the virally inactivated pool produce a purified product pool; and the method comprises transferring the purified product pool to a viral filtration device located in the second modular cleanroom to produce a virus-free filtrate.

14. The method of claim 13, wherein transferring the amount of the virally inactivated pool to the second modular cleanroom includes:

transferring the amount of the virally inactivated pool to a one or more first storage containers located outside of the first modular cleanroom and coupled to one or more first ports of the first modular cleanroom; and transferring the amount of the virally inactivated pool from the one or more first storage containers to one or more second storage containers, the one or more second storage containers being located outside of the second modular cleanroom and coupled to one or more second ports of the second modular cleanroom, the one or more second ports being coupled to the additional chromatography system located in the second modular cleanroom.

15. The method of claim 13, comprising:

transferring an amount of the virus-free filtrate to a filter device included in a third modular cleanroom;

performing, by the filter device, at least one of one or more ultrafiltration operations or one or more diafiltration operations to produce a purified therapeutic protein drug substance; and transferring an amount of the purified therapeutic protein drug substance to a number of vials at a rate of 5 vials to 100 vials per minute, the number of vials individually having a volume from about 2 mL to about 40 mL.

16. The method of claim 15, wherein the bioreactor is included in a production facility having an additional bioreactor, and the method comprises:

performing the at least one of the one or more ultrafiltration operations or the one or more diafiltration operations while an amount of an additional virally inactivated pool is processed by the additional chromatography system, the additional virally inactivated pool being produced from effluent of the additional bioreactor.

17. The method of claim 15, wherein the bioreactor is included in a production facility having an additional bioreactor, and the method comprises:

performing the at least one of the one or more ultrafiltration operations or the one or more diafiltration operations while the viral filtration device processes an amount of an additional purified product pool that is produced from the effluent of the additional bioreactor.

18. The method of claim 15, wherein:

the bioreactor is included in a production facility having an additional bioreactor;

one or more first operations are performed by one or more first pieces of equipment located in the first modular cleanroom with respect to a first amount of the effluent produced by the additional bioreactor while one or more second operations are performed by one or more second pieces of equipment located in the second modular cleanroom with respect to a second amount of the effluent produced by the bioreactor; and the one or more first operations being performed by the chromatography system and the one or more second operations being performed by at least one of the additional chromatography system or the viral filtration device.

19. The method of claim 15, comprising:

after an amount of the purified therapeutic protein drug substance is produced, removing one or more first single-use components from at least one of the bioreactor, the chromatography system, or the additional chromatography system;

replacing the one or more first single-use components with one or more second single-use components;

obtaining, by the bioreactor, additional cell culture media, additional cell growth material, and additional buffer solution from one or more storage containers; and producing an additional cell-free permeate that includes an additional recombinant therapeutic protein that is different from the recombinant therapeutic protein.

20. The method of claim 15, wherein the purified therapeutic protein drug substance is produced by a first production line having a first arrangement of a first plurality of pieces of equipment located in the first modular cleanroom, the second modular cleanroom, and the third modular cleanroom and the method comprises:

modifying the first arrangement of the first plurality of pieces of equipment to produce a second production line having a second arrangement of a second plurality of pieces of equipment located in the first modular cleanroom, the second modular cleanroom, and the third modular cleanroom, the second arrangement of the second plurality of pieces of equipment being produced by at least one of:

removing a piece of equipment included in the first plurality of pieces of equipment from the first modular cleanroom, the second modular cleanroom, or the third modular cleanroom;

adding a first additional piece of equipment to the first plurality of pieces of equipment in the first modular cleanroom, the second modular cleanroom, or the third modular cleanroom; or changing a location of a second additional piece of equipment included in the first plurality of pieces of equipment.

\* \* \* \* \*